(12) United States Patent
Lanari et al.

(10) Patent No.: US 10,039,806 B2
(45) Date of Patent: Aug. 7, 2018

(54) METHODS AND COMPOSITIONS FOR TREATING ANTIPROGESTIN-RESISTANT CANCERS

(71) Applicants: Fundación Sales, Capital Federal (AR); Consejo Nacional de Investigaciones Científicas y Técnicas, Capital Federal (AR)

(72) Inventors: Claudia L. Lanari, Buenos Aires (AR); Victoria Wargon, Capital Federal (AR); Paola Rojas, Capital Federal (AR); Maria May, Capital Federal (AR); Gonzalo Sequeira, Capital Federal (AR)

(73) Assignee: FUNDACION SALES, Capital Federal (AR)

( * ) Notice: Subject to any disclaimer, the term of this patent is extended or adjusted under 35 U.S.C. 154(b) by 0 days.

(21) Appl. No.: 14/363,551

(22) PCT Filed: Dec. 7, 2012

(86) PCT No.: PCT/US2012/068525
§ 371 (c)(1),
(2) Date: Jun. 6, 2014

(87) PCT Pub. No.: WO2013/086379
PCT Pub. Date: Jun. 13, 2013

(65) Prior Publication Data
US 2015/0202261 A1     Jul. 23, 2015

Related U.S. Application Data

(60) Provisional application No. 61/568,384, filed on Dec. 8, 2011.

(51) Int. Cl.
*A61K 31/165* (2006.01)
*A61K 31/567* (2006.01)
*A61K 31/706* (2006.01)
*A61K 38/17* (2006.01)
*A61K 45/06* (2006.01)
*A61K 31/575* (2006.01)
*A61K 31/7068* (2006.01)
*A61K 48/00* (2006.01)

(52) U.S. Cl.
CPC ........ *A61K 38/1783* (2013.01); *A61K 31/165* (2013.01); *A61K 31/567* (2013.01); *A61K 31/575* (2013.01); *A61K 31/706* (2013.01); *A61K 31/7068* (2013.01); *A61K 45/06* (2013.01); *A61K 48/005* (2013.01)

(58) Field of Classification Search
CPC . A61K 31/575; A61K 31/7068; A61K 31/165
See application file for complete search history.

(56) References Cited

U.S. PATENT DOCUMENTS

2007/0287676 A1   12/2007   Guo et al.
2010/0129320 A1   5/2010    Phiasivongsa et al.

OTHER PUBLICATIONS

Wargon et al. Breast Cancer Res. Treat., 2009, vol. 116, pp. 449-460.*
Fan et al. J. Cancer Res. Clin. Oncol., 2008, vol. 134, pp. 883-890.*
Bamberger et al. Hormone Research, 2000, vol. 54, pp. 32-37 (Abstract attached).*
El Etreby et al. Breast Cancer Research and Treatment, 1998, vol. 49, pp. 109-117.*
International Search Report and Written Opinion for PCT/US2012/068525 dated May 31, 2013.
Wargon et al; "Hypermethylation of the progeserone receptor A in constitutive antiprogestin-resistant mouse mammary carcinomas"; Breast Cancer Research and Treatment, May 4, 2010 (E-pub.), vol. 126, pp. 319-332.

* cited by examiner

*Primary Examiner* — James D. Anderson
(74) *Attorney, Agent, or Firm* — Lewis Brisbois Bisgaard & Lewis LLP; Howard M. Gitten

(57) ABSTRACT

The present invention provides methods and compositions for treating cancer patients, and in particular, breast cancer patients, who are responsive to antiprogestin therapy, or who may be induced to be responsive to an antiprogestin therapy through the administration of a demethylation agent, optionally together with an HDAC inhibitor. Further, the present invention relates to a method of screening cancer patients using BCL-XL as a marker protein.

16 Claims, 25 Drawing Sheets

| sample | ER-PR | HER-2 | PR ratio | Inhibitory index | age | Tumor size | TNM | Lymph nodes | histology |
|---|---|---|---|---|---|---|---|---|---|
| 65 | RP+ RE+ | - | PR-A>PR-B | 2.5 | 35 | 3 cm | nd | neg | Invasive carcinoma (lobular + ductal carcinoma) with areas of mucin secretion |
| 126 | RE+ RP+ | - | PR-A>PR-B | 2.5 (ns) | 57 | 1.5 cm (left breast) 0.4 cm (right breast) | Tis N0M0 (r) T1N1M0 (l) | neg (left and right breast) | Invasive ductal carcinoma left breast and right breast |
| 137 | RP+ RE+ | - | PR-A>PR-B | 1.6 | 78 | 3 cm | T2N0M0 | neg | Mucinous carcinoma with areas of invasive ductal carcinoma |
| 139 | RP+ RE+ | nd | PR-A>PR-B | 1.3 | 44 | 7.5 cm | T3N0M0 | neg | Phyllodes tumor borderline |
| 140 | RE+ RP+ | - | PR-A>PR-B | 1.6 (ns) | 75 | 2 cm | T1N1M0 | positive | Invasive ductal carcinoma |
| 150 | RE- RP- | - | PR negative | 1.08 No resp | 51 | 4 cm | T1N1M0 | neg | Indifferentiated carcinoma with areas of metaplastic differentiation |
| 64 | RE+ RP- | nd | PR negative | 1.06 No resp | 47 | 2.2 cm | T1N1M0 | 30/30 | Invasive ductal carcinoma |
| 171 | RE- RP- | - | PR negative | 1 No resp | 55 | 3.5 cm | nd | nd | Invasive ductal carcinoma |

FIG. 2C

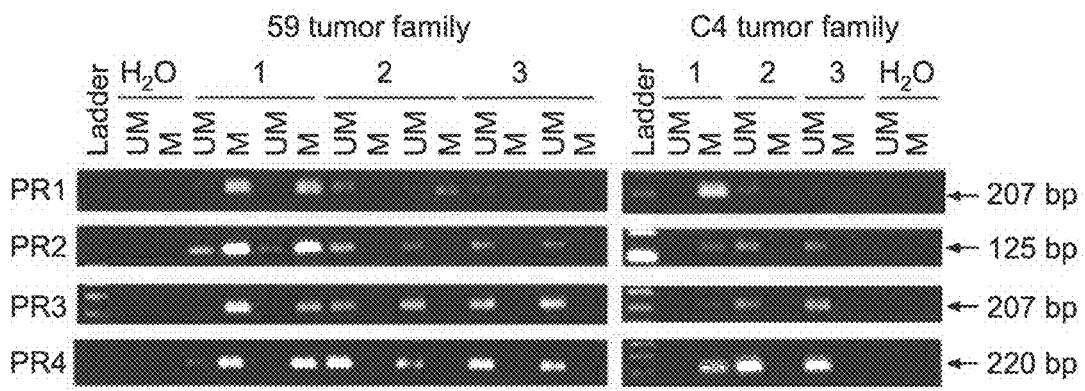
FIG. 9B
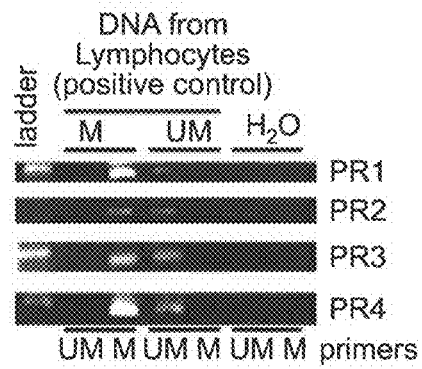
FIG. 9C
FIG. 9D

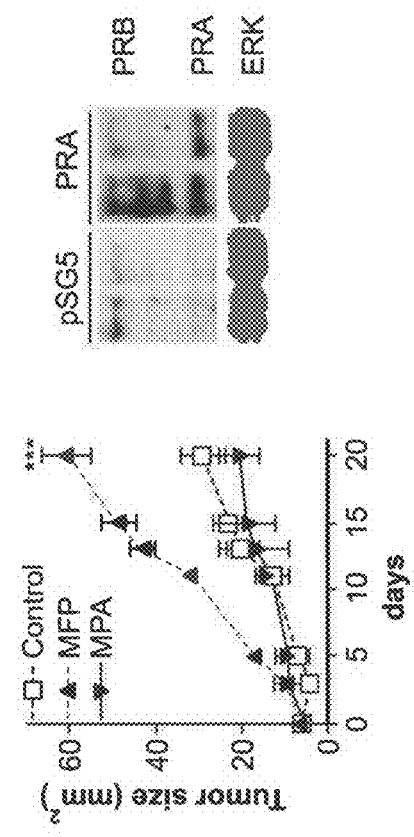
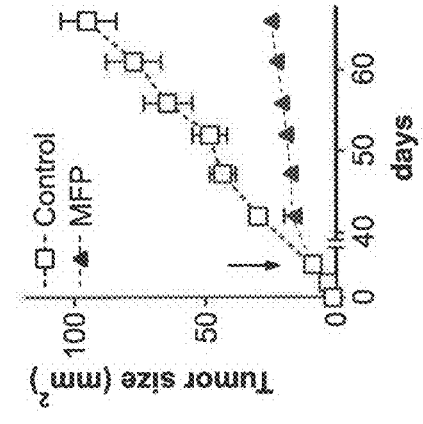
FIG. 22A
FIG. 22B

METHODS AND COMPOSITIONS FOR TREATING ANTIPROGESTIN-RESISTANT CANCERS

RELATED APPLICATION DATA

This application is the U.S. National Stage, pursuant to 35 U.S.C. § 371, of U.S. International Application No. PCT/US2012/068525, filed Dec. 7, 2012, designating the United States and published on Jun. 13, 2013 as Publication WO 2013/086379, which claims priority to U.S. provisional patent application Ser. No. 61/568,384, filed Dec. 8, 2011, the entire contents of which are hereby incorporated herein by reference.

SEQUENCE LISTING

The instant application contains a Sequence Listing which has been submitted electronically in ASCII format and is hereby incorporated by reference in its entirety. Said ASCII copy, created on Apr. 2, 2015, is named 89708(302400) SL.txt and is 15,179 in size.

INCORPORATION BY REFERENCE

Any and all references cited in the text of this patent application, including any U.S. or foreign patents or published patent applications, International patent applications, as well as, any non-patent literature references, including any manufacturer's instructions, are hereby expressly incorporated by reference.

BACKGROUND OF THE INVENTION

1. Field of the Invention

This invention relates generally to the field of cancer therapy and treatment. Further, the invention relates to novel endocrine therapies for treating cancers, and in particular, cancers that express different ratios of progesterone receptor isoforms. Depending on the prevailing isoform expressed, such cancers may become sensitive or resistant to an antiprogestin therapy. The invention particularly provides methods and compositions for overcoming resistance to these progesterone receptor-related endocrine therapies in cancers, and especially in breast cancers. Moreover, the invention relates to screening methods for detecting tumors that express certain progesterone receptor isoforms.

2. Background

Breast cancer is the most frequently diagnosed malignant neoplasia and is a leading cause of cancer death in females worldwide. Breast cancer ranks second overall in cancer mortality (10.9%) and accounts for 23% (1.38 million) of new cancer diagnoses and 14% (458,400) of total cancer deaths (Jemal, et al. 2011). Breast cancer is not a single disease but instead constitutes a spectrum of lesions with distinct cellular origins, somatic changes, and etiologies.

Gene expression studies have divided breast cancer into several categories, including, but not limited to, basal-like, ErbB2-enriched, normal breast-like (adipose tissue gene signature), luminal subtype A, luminal subtype B and claudin-low (Prat, et al. 2010). More than 66% of breast carcinomas express estrogen receptor alpha (ERα) and respond to anti-estrogen therapies.

These carcinomas may also express progesterone receptors (PRs), which are a reliable marker of functional ERs (Kastner, et al. 1990; Petz and Nardulli 2000). Estrogen and progesterone and their respective receptors are widely regarded as playing important roles in the etiology of breast cancers.

Endocrine therapies seeking to block or inhibit the action of estrogen have been known for some time now but the emergence of resistance to such therapies remains a limitation. For example, antiestrogen treatment, such as tamoxifen therapy, remains a central and successful approach in the treatment of this disease but resistance remains a major setback. Most tumors initially respond to antiestrogen therapy, but many will eventually develop resistance (acquired hormone resistance). Moreover, some tumors fail to respond to endocrine treatment from the beginning (constitutive resistance) despite expressing hormone receptors. Much less is known about the role of the progesterone receptor (PR) in cancer etiology, or its role as a viable target for antiprogestin-based therapies in the treatment of cancer.

The PR is a member of the steroid-thyroid hormone-retinoid receptor superfamily of ligand-activated nuclear transcription factors (Evans 1988; Kastner et al. 1990). Upon progesterone binding, which has been shown to be required for the proliferation of mammary glands and mammary carcinomas, the receptor undergoes a series of conformational changes, dimerizes and translocates to the nucleus, where it interacts with specific DNA sequences (Progesterone Response Elements, PREs) in the promoter regions of target genes (Edwards, et al. 1995; Lange et al. 2008). These transcriptional effects may also be mediated by PRE independent actions through protein-protein interactions between the PR and other sequence specific transcription factors (Leonhardt, et al. 2003). The PR, like all transcription factors, localizes to the nuclear compartment. It has also been described to be located in the cytoplasm and at the cell membrane (Bottino, et al. 2011), where it triggers non-genomic or membrane initiated signaling pathways.

Accordingly, progesterone receptors are members of the steroid hormone receptor family which are ligand-activated nuclear transcription factors, which when bound by progesterone, dissociate from chaperone proteins, dimerize, and bind to specific DNA sequences, enhancing transcription of target genes. PR target genes encode a wide range of proteins that control or modulate crucial cellular functions, such as cell growth, apoptosis, transcription, steroid and lipid metabolism (Li and O'Malley 2003).

Two PR isoforms have been described: isoform B (PR-B), which is 933 amino acids long in humans with a molecular weight of 116 kDa, and isoform A (PR-A), which lacks 164 amino acids at the N-terminus but is otherwise identical to isoform B (MW: 94 kDa; see FIG. 1). They are transcribed from two different promoters of the same gene on human chromosome 11 q22-q23 (Kastner et al. 1990) or on chromosome 9 in mice (band 9A1). In mice, the isoforms have a molecular weight of 115 and 83 kDa, respectively (Schneider, et al. 1991).

When PR-A and PR-B are present in equimolar amounts in wild-type PR-positive cells or are transiently co-expressed in PR-negative cells, they dimerize and bind to DNA as three species: A/A and B/B homodimers and A/B heterodimers. Post-transcriptional modifications of the PR include acetylation, sumoylation and ubiquitination (Dressing and Lange 2009; Hagan, et al. 2009), and especially including phosphorylation. Phosphorylation affects the ability of the PRs to interact with the promoters of their target genes and the subsequent transcriptional activation of these genes (Clemm, et al. 2000). Additionally, phosphorylation affects PR subcellular localization and stability and its ability to interact with other proteins (Clemm et al. 2000).

There is also increasing evidence that isoforms PR-A and PR-B have different functions in vitro and in vivo. It has been speculated that differential expression of PR-A and PR-B is critical for an appropriate mammary gland response to progesterone. Indeed, in transgenic mice carrying an excess of PR-A, mammary gland development is characterized by disproportionate lateral ductal branching, whereas transgenic mice overexpressing PR-B show alterations in lobulo-alveolar growth. PR-A null mice, which only express PR-B, exhibit normal mammary gland development, although they show severe reproductive defects, while PR-B null mice show impaired branching morphogenesis. Taken together, this suggests that PR-A and PR-B have different functions in different tissues and that the described alterations are related to their relative expression ratios.

It has been further observed that PR-A is often over expressed as compared to PR-B (Graham, et al. 2005; Graham, et al. 1995) in breast tissue. In addition, higher molar amounts of PR-A to PR-B have been associated with poorer outcome in patients undergoing hormonal therapy (Hopp, et al. 2004) and even resistance to hormone treatments. Therefore, the PR isoform ratio may be important in breast cancer prognosis and therapeutic decisions, and a clear understanding of the role the different isoforms play in cancer development and hormone resistance will be crucial in the development of hormone anticancer therapies, and in particular, in the use of antiprogestins in treating cancer.

Methods and compositions which would enable the improved use of hormone anticancer therapies, and in particular, the use of antiprogestins for the treatment of cancers, and in particular, breast cancers, which are or may become resistant to such therapies, would be an important advance in the art.

SUMMARY OF THE INVENTION

Many carcinomas, and especially breast carcinomas, that are estrogen receptor (ER) and progesterone receptor (PR) positive respond initially to an endocrine therapy, but over time, develop resistance (acquired hormone resistance). Others, however, fail to respond from the beginning (constitutive resistance). Overcoming hormone resistance is one of the major desirable aims in breast cancer treatment. The present invention overcomes these hurdles based, at least in part, on the surprising discovery that carcinomas, in particular, breast carcinomas, which are PR-positive and which express a higher molar amount of PR-A relative to or compared with the molar amount of PR-B (i.e., a higher PR-A/PR-B ratio) are responsive to antiprogestins. It has further been surprisingly discovered that different genetic mechanisms are responsible for resistance to antiprogestins in those tumors which show constitutive resistance (fail to respond from the beginning of treatment) to antiprogestins as compared to the tumors that acquire resistance (resistance develops after treatment begins) to antiprogestins. In particular, the inventors surprisingly discovered that constitutive resistance to antiprogestins is attributable to DNA methylation events of the gene and promoter encoding the PR-A (i.e., the PRA gene). In addition, the inventors have discovered that constitutive resistant mammary carcinomas showed high levels of HDAC1 (histone deacetylase), which without being limited to theory, may be responsible for histone acetylation within the methylated PRA promoter. Accordingly, in a first aspect, the inventors defined a new endocrine-based treatment for use in treating cancers with constitutive resistance to antiprogestins that involves the co-administration of both a demethylating agent and an antiprogestin. In a second aspect, the inventors have discovered that by also co administering an HDAC inhibitor, such as TSA, together with a demethylating agent, a cancer which insensitive to antiprogestin treatment may be resensitived to a greater degree than with the demethylating agent alone. Thus, in this second aspect, the invention relates to a therapy involving the co-administration of an antiprogestin together with both a demethylating agent and a HDAC inhibitor. Accordingly, treatment may optionally include a HDAC inhibitor.

Accordingly, in one aspect, the present invention relates to the identification of a cancer patient, and in particular, a breast cancer patient, who is responsive to an antiprogestin therapy, including the steps of (a) obtaining a sample of the cancer to be treated; and (b) determining the molar amount of PR-A to PR-B of the cancer sample, wherein the patient is a viable candidate for antiprogestin therapy if the molar amount of PR-A is greater than that of PR-B. Such antiprogestin therapy may be conducted in combination with standard endocrine treatment aimed to block ER.

In another aspect of the present invention, the invention provides a method of treating a cancer, preferably a breast cancer, which is responsive to an antiprogestin therapy comprising the steps of (a) identifying a patient responsive to an antiprogestin therapy as have a greater molar amount of PR-A as compared to PR-B, and (b) administering a therapeutically effective amount of an antiprogestin therapy to the responsive patient.

In still another aspect, the present invention relates to a method of treating a patient having cancer, e.g., breast cancer, which is constitutively resistant to an antiprogestin therapy comprising, increasing the molar ratio of PR-A to PR-B such that the molar amount of PR-A is greater than the molar amount of PR-B and administering a therapeutically effective amount of an antiprogestin therapy thereby treating the patient.

In still another aspect, the present invention relates to a method of treating a patient having cancer, e.g., breast cancer, which is constitutively resistant to an antiprogestin therapy comprising, demethylating the PRA gene to increase the molar ratio of PR-A to PR-B such that the molar amount of PR-A is greater than the molar amount of PR-B and administering a therapeutically effective amount of an antiprogestin therapy thereby treating the patient.

In yet another aspect, the present invention relates to a method of treating an antiprogestin resistant cancer, e.g., breast cancer, by increasing the ratio of PR-A to PR-B in the cancer by inhibiting DNA methyltransferases and optionally, additionally inhibiting histone deacetylase (HDAC), and administering a therapeutically effective amount of an antiprogestin, thereby treating the cancer.

In another aspect, the invention relates to a method of treating an antiprogestin-resistant breast cancer comprising co-administering therapeutically effective amounts of an antiprogestin and a demethylating agent, thereby treating the carcinoma.

In still another aspect, the invention relates to a method of treating an antiprogestin resistant breast cancer comprising co-administering therapeutically effective amounts of an antiprogestin, a demethylating agent, and a HDAC inhibitor, thereby treating the carcinoma.

In still another aspect, the present invention provides a therapeutic or pharmaceutical composition comprising a demethylation agent and optionally an HDAC inhibitor and an antiprogestin for use in treating a patient having a constitutive antiprogestin-resistant cancer.

In various embodiments, the cancer is breast cancer.

In certain embodiments, the cancer is characterized as having a higher molar amount of PR-A as compared to PR-B and is responsive to treatment with an antiprogestin.

In various other embodiments, prior to any treatment with an antiprogestin, the molar amount of PR-A is less than the molar amount of PR-B in the cancer to be treated. In certain embodiments, the ratio of PR-A to PR-B will be increased in such cancers to restore responsiveness of the cancer to treatment with an antiprogestin.

In still other embodiments, the molar amount of PR-A is greater than the molar amount of PR-B in the cancer to be treated. Such cancers will be responsive to treatment with an antiprogestin.

In certain embodiments, the antiprogestin is a Type I, Type II, or Type III antiprogestin.

In certain other embodiments, the antiprogestin is onapristone, mifepristone (RU-486), lonaprisan, aglepristone (Ru-534), Org31710, Org31806, CDB-2914, or CDB-4124.

In other embodiments, the demethylation agent is a nucleotide analog which blocks, prevents, or inhibits the functioning of DNA methyltransferase. In an embodiment, the demethylating agent is 5azadC. The demethylating agent can also be any other suitable demethylating agent, including, but not limited to azacytidine (aza) and zebularine.

In another embodiment, the HDAC inhibitor is TSA (trichostatin A).

In other embodiments, the HDAC inhibitor can be Vorinostat, Romidespin, Panobiostat (LBH589), Valproic acid, Belinostat (PXD101), Mocetinostat (MGCD0103), PCI-24781, Entinostat (MS-275), SB939, Resminostat (4SC-201), Givinostat (ITF2357), CUDC-101, AR-42, CHR-2845, CHR-3996, 4SC-202, sulforaphane, and Givinostat (ITF2357), many of which are currently in clinical trials for various cancer, psychiatry, and neurological uses.

In specific embodiments, the invention provides a method of treating a subject having a carcinoma that is resistant to an antiprogestin comprising increasing the molar amount of progesterone receptor isoform A (PR-A) so that it is greater than that of isoform B (PR-B) and administering a therapeutically effective amount of an antiprogestin, thereby treating the carcinoma. The step of increasing the molar amount of PR-A so that it is greater than that of PRB further can comprise administering a therapeutically effective amount of a nucleic acid molecule encoding PR-A. The step of increasing the molar ratio of PR-A so that is greater than that of PR-B further can also comprise administering a therapeutically effective amount of an inhibitor of PR-B expression. The method of increasing the molar ratio of PR-A so that is greater than that of PR-B further can also comprise administering a therapeutically effective amount of a demethylating agent, e.g., 5azadC, optionally together with a HDAC inhibitor, e.g., TSA.

In another specific embodiment, the invention provides a method of treating a constitutive antiprogestin-resistant breast cancer comprising increasing the molar amount of PRA to PR-B in the breast cancer and administering a therapeutically effective amount of an antiprogestin, thereby treating the cancer. The step of increasing the molar amount of PR-A so that it is greater than that of PR-B further can comprise administering a therapeutically effective amount of a nucleic acid molecule encoding PR-A. The step of increasing the molar ratio of PRA so that is greater than that of PR-B further can also comprise administering a therapeutically effective amount of an inhibitor of PR-B expression. The method of increasing the molar ratio of PR-A so that is greater than that of PR-B further can also comprise administering a therapeutically effective amount of a demethylating agent, e.g., 5azadC, optionally together with a HDAC inhibitor, e.g., TSA.

In still another specific embodiment, the invention provides a method of treating an antiprogestin-resistant breast cancer comprising increasing the amount of PR-A to PR-B in the carcinoma by administering a demethylating agent together with an HDAC inhibitor prior to or incident with administering a therapeutically effective amount of an antiprogestin, thereby treating the carcinoma. The step of increasing the molar amount of PR-A so that it is greater than that of PR-B further can comprise administering a therapeutically effective amount of a nucleic acid molecule encoding PR-A. The step of increasing the molar ratio of PR-A so that is greater than that of PR-B further can also comprise administering a therapeutically effective amount of an inhibitor of PR-B expression. The method of increasing the molar ratio of PR-A so that is greater than that of PR-B further can also comprise administering a therapeutically effective amount of a demethylating agent, e.g., 5azadC, optionally together with a HDAC inhibitor, e.g., TSA.

The antiprogestin can be a Type I, Type II, or Type II antiprogestin. Specific antiprogestins can include, but are not limited to, onapristone, mifepristone (RU-486), lonaprisan, aglepristone (Ru-534), Org31710, Org31806, CDB-2914, or CDB-4124.

In other embodiments, the methods of the invention can further comprise co-administering a second anticancer agent.

The subject of the invention can be a human. In other embodiments, the subject can be an animal, including, a mouse, rat, cow, pig, horse, cat, or dog.

In other embodiments, the invention provides a pharmaceutical composition having an antiprogestin (e.g., onapristone, mifepristone (RU-486), lonaprisan, aglepristone (Ru-534), Org31710, Org31806, CDB-2914, or CDB-4124), a demethylating agent, such as, but not limited to 5azadC and optionally a HDAC inhibitor such as, but not limited to, TSA.

The invention also provides in other embodiments a kit comprising an antiprogestin and a demethylating agent alone or together with an HDAC inhibitor for treating a breast cancer which is resistant to the antiprogestin and instructions for use.

Any compositions or methods provided herein can be combined with one or more of any of the other compositions and methods provided herein.

In yet another embodiment of the invention, screening methods for detecting tumors that express certain progesterone receptor isoforms are provided.

BRIEF DESCRIPTION OF THE DRAWINGS

The following Detailed Description, given by way of example, but not intended to limit the invention to specific embodiments described, may be understood in conjunction with the accompanying drawings, in which.

(A) Shows images of tumor #137 treated or not (control) with 10-8 M RU-486 or 10-8 M TAM (tamoxifen). Magnification 400×. Bars represent the number of cells after treatment.

(B) Shows Ki67 and Cytokeratin coimmunostaining in tumor #171. Magnification 400×. Bars represent the percentage of Ki67 stained cells in control and 10-8 M RU-486 treated cells.

(C) Table summarizing data of breast tumor samples treated with RU-486. inhibitory index: samples #150, #64, and #171 did not show any response when were treated with RU-486 in primary cultures (as shown in B). The rest of the samples (#137, #139, #140, #65, and #126) responded to RU-486 treatment, #140 and #126 were not significant. (nd) non-determined, (ns) not significant, (r) right, (l) left.

Figure 3A:
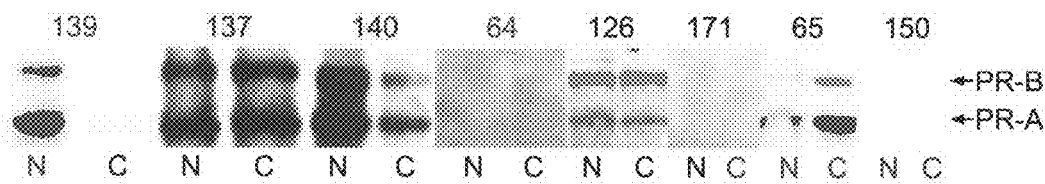
Figure 3B:
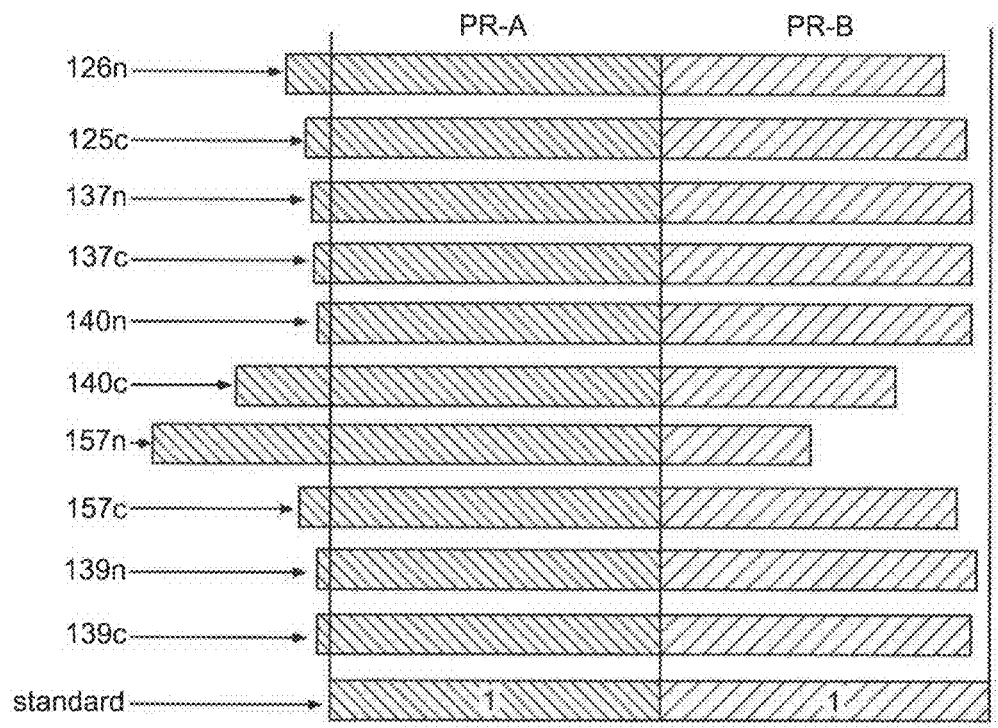

FIG. 3 relates to an embodiment of the invention, as described in Example 1, which demonstrates that tumor breast samples expressing an increased PR-A/PR-B ratio respond to RU-486 treatment. (A) Shows the evaluation of PR-A and PR-B expression in tumor samples which were used in primary cultures and treated with RU-486. Representative WV of the PR (PgR 1294 antibody) using nuclear [N] and cytoplasmic [C] protein extracts. Samples #137, #139, #140, #65, and #126 showed higher levels of PR-A (83 kDa) than PR-B (115 kDa). (B) PR-A and PR-B bands were quantified and the PR-A/PR-B ratio was calculated and is displayed visually in the bar graph. The "standard" shows equivalent amounts of PR-A and PR-B having a ratio of 1:1.

Figure 4:
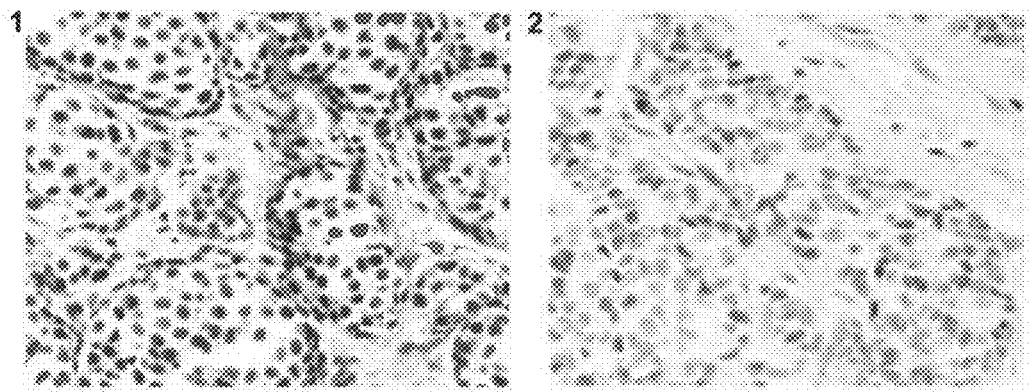

FIG. 4 relates to an embodiment of the invention, as described in Example 1, which shows the results of PR (PgR 1294 antibody) immunostaining in tumors #140 (a) and #137 (2). Magnification 400×.

Figure 5:
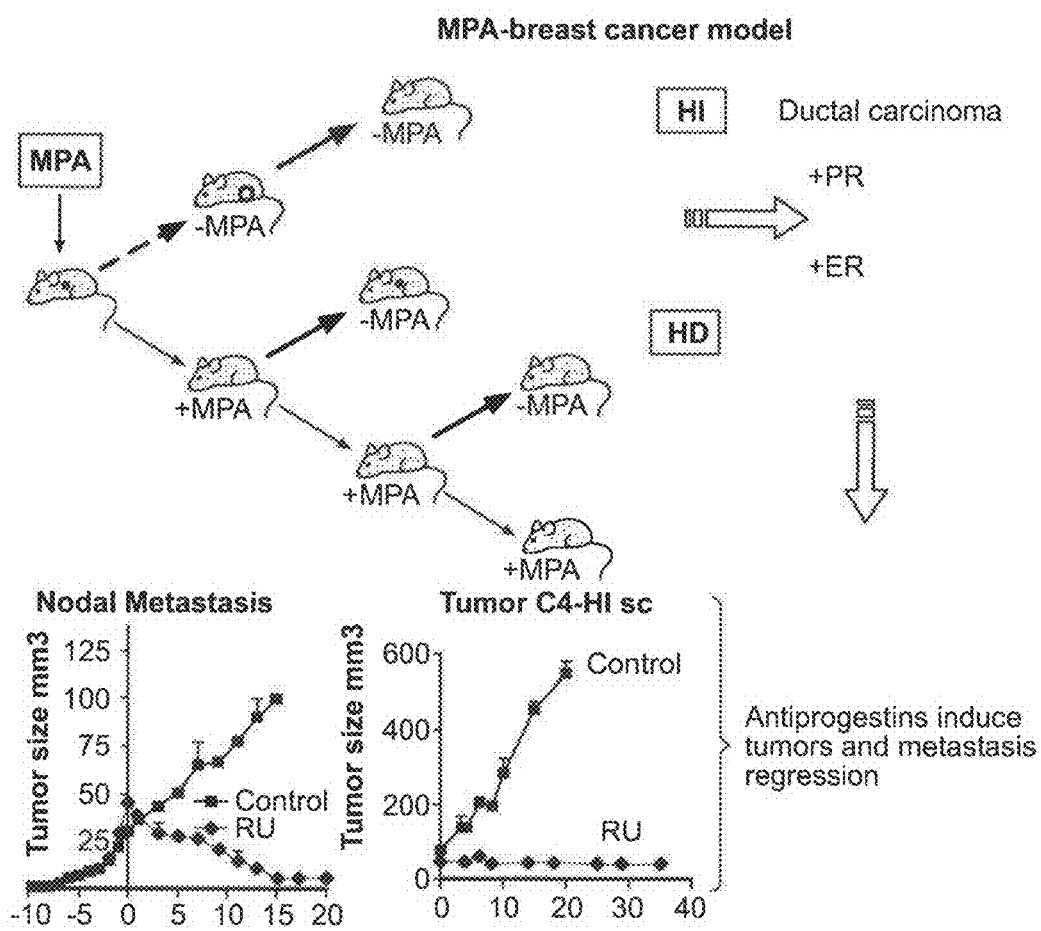

FIG. 5 displays the MPA-breast cancer model employed in Example 1. In this model of breast cancer, the administration of medroxyprogesterone acetate (MPA) to BALB/c female mice induces mammary ductal carcinomas. These tumors are metastatic and express both ER (estrogen receptor) and PR (progesterone receptor), transit through different stages of hormone responsiveness and respond and even regress completely after antiprogestin treatment.

Figure 6:
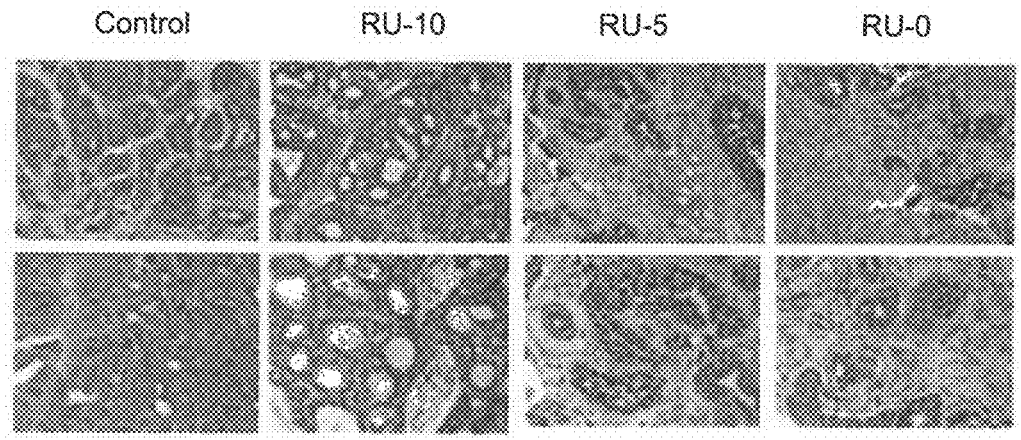

FIG. 6 shows sections stained with hematoxilyn-eosin of C4HI tumors growing in mice treated or not treated (control) with RU-486 during 10 days ("RU-10"), 15 days ("RU-15"), and 20 days ("RU-0"). Magnification 1-4 200×, 5-8 400×.

Figure 7:
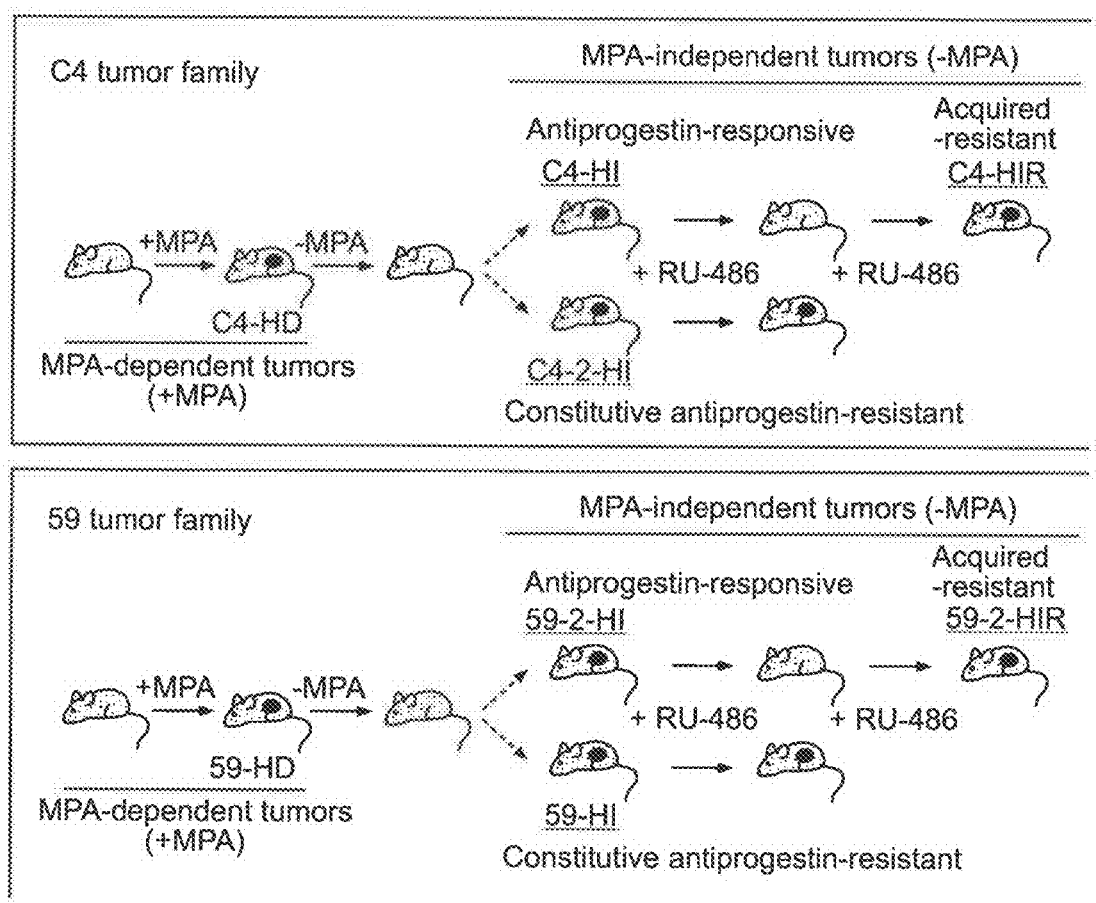

FIG. 7 provides a schematic depicting the origin of the tumors of the MPA breast cancer model used in Example 2. MPA-induced ductal hormone-dependent mammary carcinomas are maintained by syngeneic transplantation in progestin-treated BALB/c mice (C4-HD and 59-HD). Occasionally, some tumors started to grow in untreated mice giving rise to MPA-independent variants. These variants were named chronologically prior to testing their hormone responsiveness. While most of the MPA-independent tumors regressed in response to RU-486 (C4-HI and 59-2-HI), some constitutive-resistant variants were obtained (C4-2-HI and 59-HI). In addition, MPA-independent responsive tumors treated with RU-486 gave rise, by selective pressure, to acquired antiprogestin-resistant variants (C4-HIR and 59-2-HIR). Tumors used in this study are underlined.

Figure 8A:
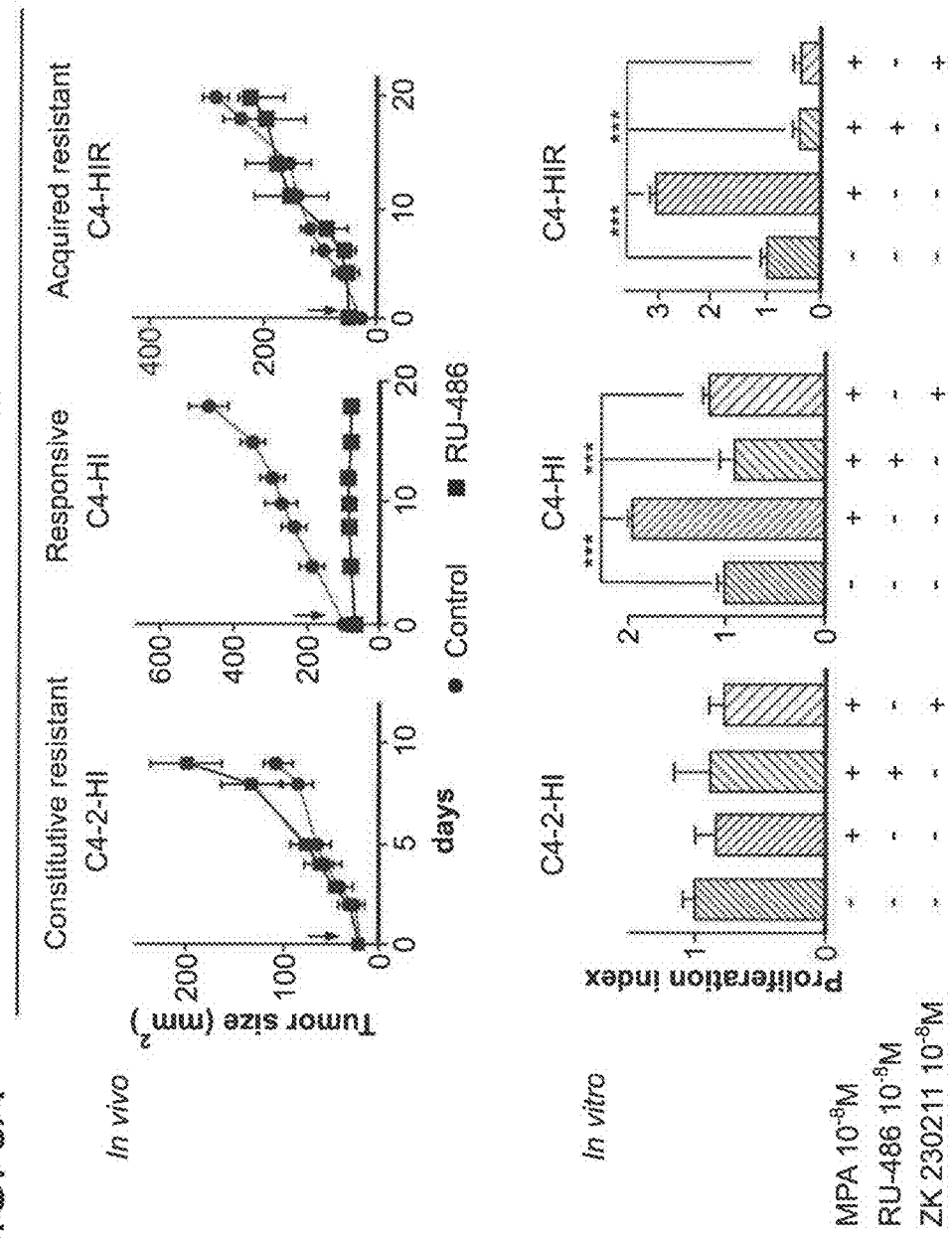
Figure 8B:
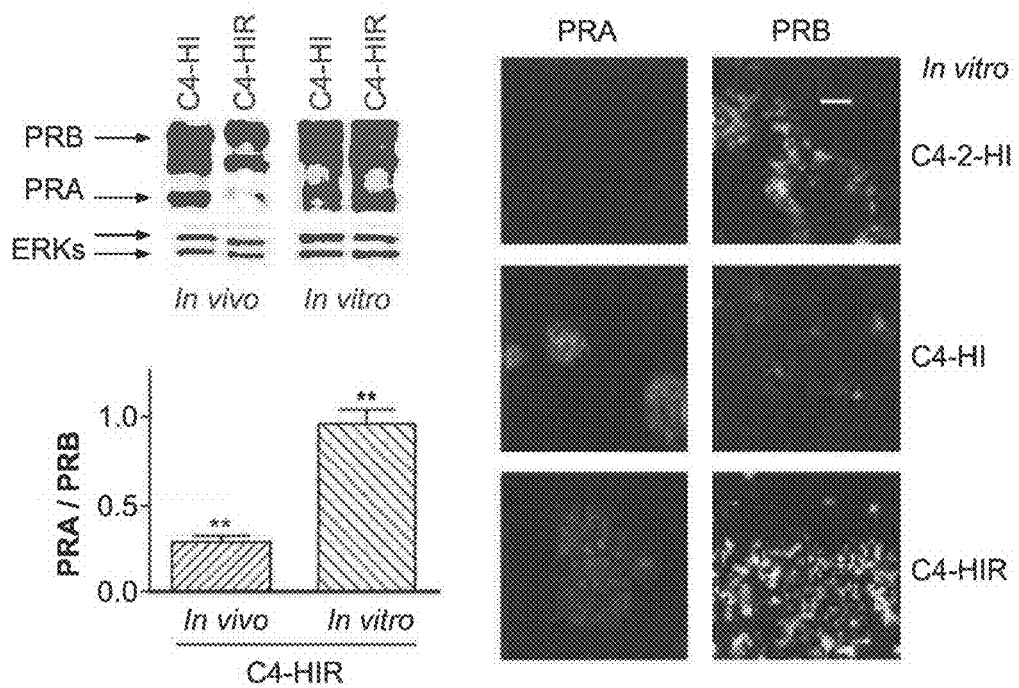

FIG. 8 demonstrates that acquired antiprogestin-resistant tumors revert their antiprogestin resistance and the PR-A/PR-B ratio in culture. (a) Hormone responsiveness. Top Growth curves from tumors of the C4 family illustrating their hormone responsiveness (already published); bottom Primary cultures of purified epithelial cells from the same tumors were subcultured in 96-well microplates. After attachment, the medium was replaced by 1% chFCS. The cells were then treated for 48 h with MPA with or without RU-486 or ZK 230211. Proliferation index was calculated as experimental cpm/control cpm (mean±SEM), and a representative experiment from the three, using octuplicates in each experiment, is shown. C4-HIR tumors acquired MPA and antiprogestin responsiveness when cultured in vitro; ***P<0.001. (b) Western blots. Representative blots for PR-A (83 kDa) and PR-B (115 kDa) using nuclear extracts from the tumors or cultures. The polyclonal rabbit C-19 antibody was used. ERKs were used as loading controls. The ratio of PR-A/PR-B in three different blots using different samples was quantified. C4-HIR tumors cultured on plastic reverted the PRA/PRB ratio (P<0.01; bottom). (c) Immunofluorescence for PR-A (Ab-7) and PR-B (Ab-6) in cells growing on plastic. Cells were seeded in chambers slides, starved for 24 h, then fixed, and incubated with Ab-7 or Ab-6 antibodies as described in "Materials and methods" section in Example 2. FITC-conjugated mouse secondary antibodies were used. No staining was observed in the absence of the primary antibodies (not shown). Cells with acquired resistance re-expressed PR-A: bar: 100 μm.

Figure 9A:
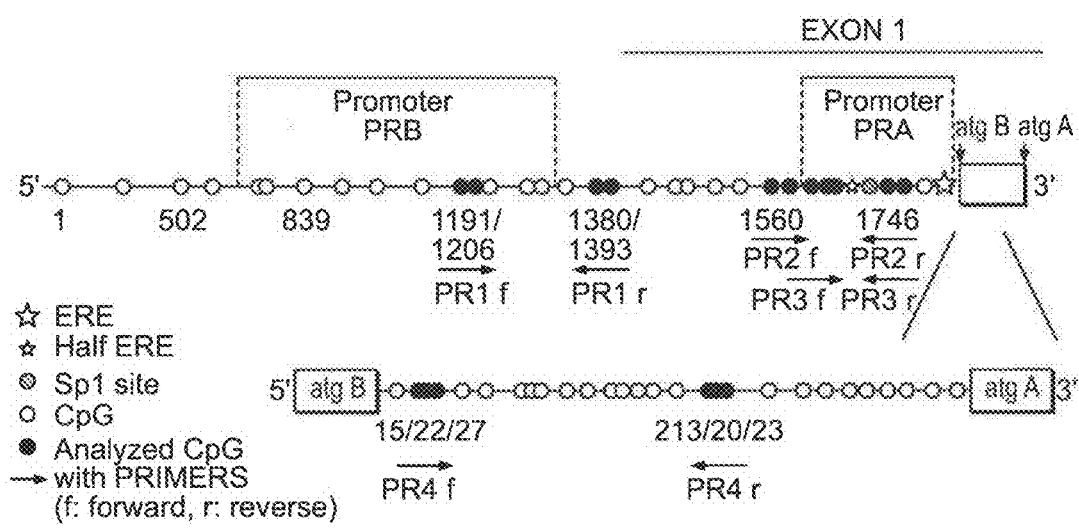

FIG. 9 demonstrates the results of methylation studies of Example 2. (a) Provides a diagram showing the PR promoters and the primers used. The sequences of the primers are provided in Table 1 herein. ERE: estrogen response element; Sp1: stimulatory protein one. (b) DNA methylation of the PR promoter detected using (MSP). Bisulfite-treated DNA samples from responsive tumors (C4-HI and 59-2-HI), tumors with acquired resistance (C4-HIR and 59-2-HER) and constitutive-resistant tumors (C4-2-HI and 59-HI) were used for amplification using the specific primers shown in Table 1 and FIG. 9a. Controls without DNA (H2O) were included. Only tumor samples from constitutive-resistant tumors showed bands using the methylated (M) primers. (c) Normal lymphocytes DNA was used as unmethylated (UM) control, and treated with SssI methyltransferase as M control. (d) The PCR products amplified with PR4 primers (M and UM) from three samples of each responsive (C4-HI, 59-2-HI), three constitutive (C4-2-HI, 59-HI) and three acquired resistant (C4-HIR, 59-2-HIR) tumors were cloned in competent E. coli TOP-10 and five colonies from each sample were sequenced by Macrogen Inc. (Korea). A diagram illustrating the CpG sites that were methylated in one representative sample is also shown.

Figure 10A:
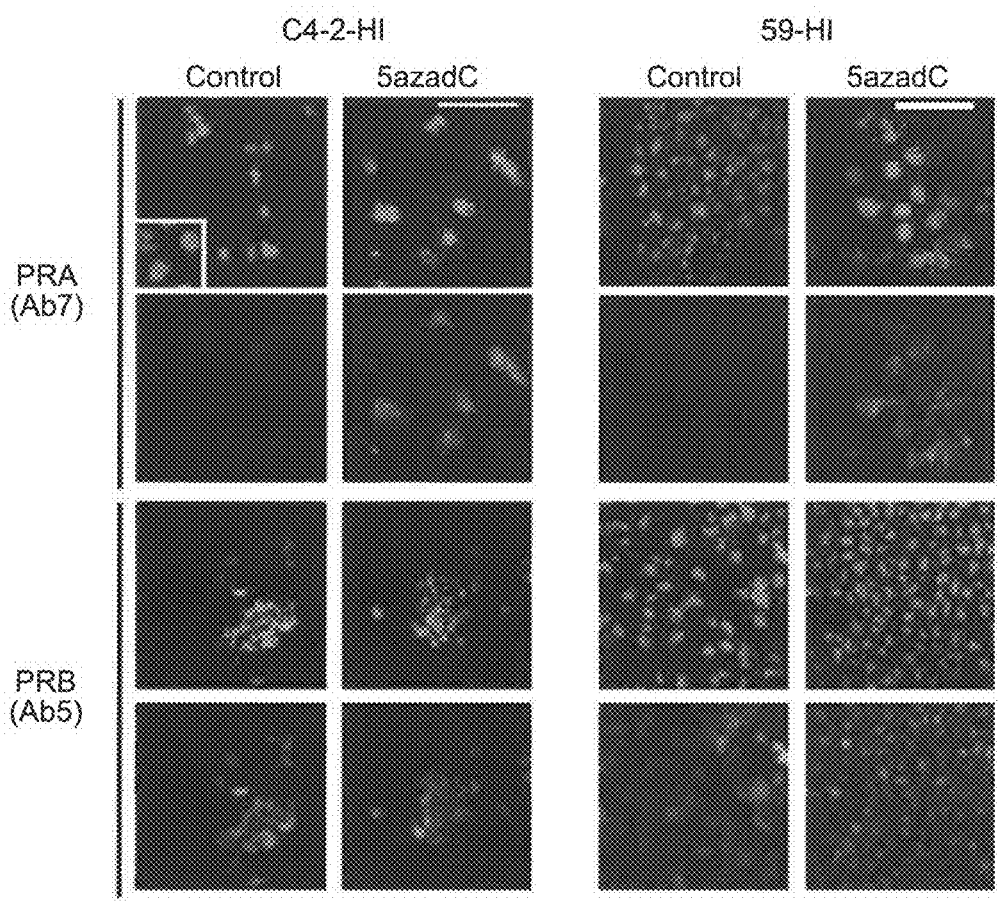
Figure 10B:
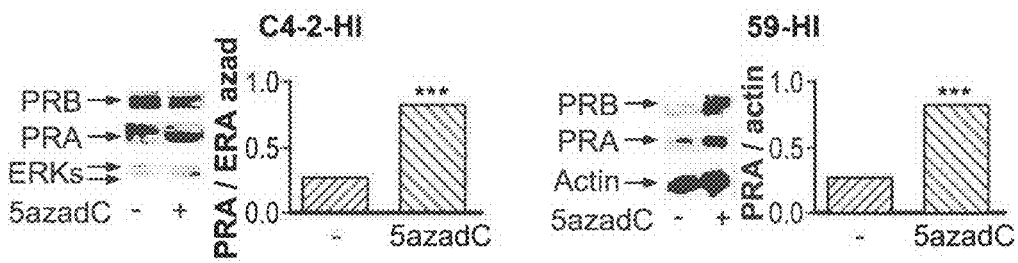
Figure 10C:
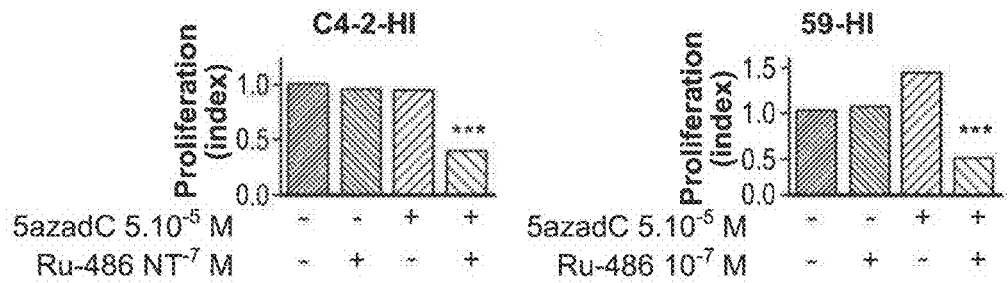

FIG. 10 demonstrates the treatment of primary cultures of constitutive-resistant tumors with 5azadC and RU-486. a PRA (Ab-7) and PRB (Ab-6) expression in control or 5azadC treated cells. Cells growing in chamber slides in the presence of 10% FCS were treated for 96 h with or without 5azadC (C4-2-HI: 5×10-7 M; 59-HI: 5×10-6 M) and processed for immunofluorescence. FITC-conjugated secondary anti-mouse antibodies were used. PI was used for nuclear counterstaining. b PRA and PRB expression was studied by western blot using Ab-7 and Ab-6 antibodies in whole cell extracts of primary cultures of constitutive-resistant tumors treated with or without 5azadC as described in a. PRA expression was quantified in three different blots using different extracts, and an increase in PRA expression was observed in treated cells. *P<0.001. c Effects of 5azadC and RU-486 on (3H)-thymidine uptake. Cells were seeded in 96 microplates and were treated with vehicle, 5azadC, RU-486, or both in the presence of 10% FCS for 48 h. Only 5azadC plus RU-486 inhibited cell proliferation. *P<0.001 experimental versus control. Proliferation index was calculated as experimental cpm/control cpm (mean±SEM), and a representative experiment from three using octuplicates in each experiment, is shown.

FIG. 11 demonstrates treatment of constitutive-resistant tumors is vivo with 5azadC and RU-486. (a) Growth curves. C4-2-HI and 59-HI tumors were transplanted sc into BALB/c female mice. When tumors were palpable, animals (five per group) were treated with vehicle, RU-486 (12 mg/kg/day, s.c.) and or 5azadC (0.75 mg/kg every other day for C4-2-HI tumors and 1 mg/kg every other day for 59-HI; i.p.). Tumor size was measured every other day (length and width) with a Vernier Caliper, and the mean±SEM of a representative experiment of the other two is plotted. Inhibition of tumor growth was observed only with combined treatments. (b) Morphological studies. Representative images of H&E-stained slides showing an increase in stromal tissue intermingled with the epithelial nests were observed only in RU-486- and 5azadC treated tumors. (c) Immunohistochemistry for PRA. Formalin-fixed tumors were processed for immunhistochemistry as described in "Materials and methods" for immunohistochemistry as described in "Material and methods" section. The polyclonal rabbit C-19 antibody was used. 5azadC-treated tumors re-expressed PRA. Nuclear and cytosolic straining was observed for C4-2-HI tumors with cytosolic and perinuclear staining was observed for 59-HI tumors (insets). (d) Western blots for PRA. Treated and untreated tumors were processed for western blotting as described in "Materials and methods" section. A representative blot of the other three is shown. ERK was used as loading control. An increase in PRA expression was observed in both cytosolic ($P<0.01$) and nuclear ($P<0.005$) extracts of 5azadC-treated C4-2-HI tumors, and only in the cytosolic fraction of 5azadC-treated 59-HI tumors ($P<0.01$).

Figure 12:
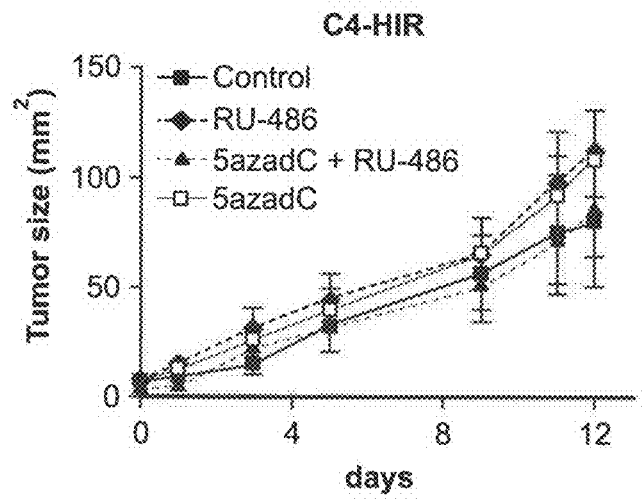

FIG. 12 demonstrates acquired resistant tumors do not reverse the resistant phenotype when treated with a demethylating agent. C4-HIR tumors were transplanted s.c. into BALB/c female mice. When tumors were palpable, animals (five per group) were treated with vehicle, RU-486 (12 mg/kg/day, s.c.) and/or 5azadC (0.75 mg/kg every other day; i.p.). Tumor size was measured every other day (length and width) with a Vernier Caliper, and the mean±SEM of a representative experiment of the other two is plotted. No inhibition in tumor growth was observed in 5azadC- and RU-486-treated mice.

FIG. 13 demonstrates expression of Dnmts in constitutive-resistant tumors compared with the responsive tumors and expression of proteins regulated by methylation. (a) Top: Immunofluorescence in primary cultures. Cells growing in chamber slides with 10% FCS were fixed and immunostained with Dnmt3a-, Dnmt3b-, and Dnmt1-specific antibodies and FITC labeled secondary antibodies. PI was used for nuclear staining. Staining was quantified as explained in "Materials and methods" section. C4-2-HI cells express a higher level of Dnmt3a and 3b ($P<0.05$) and Dnmt1 ($P<0.001$) than C4-HI and only a higher level of Dnmt3b ($P<0.001$) was observed in 59-HI compared with 59-2-HI. Bottom: Immunofluorescence in frozen tumor sections. Frozen sections from the same tumors samples which were analyzed by MSP were immunostained for Dnmt3a, Dnmt3b, and Dnmt1 using the same antibodies described above. C4-2-HI expressed higher levels of Dnmt3a, Dnmt3b, and Dnmt1 ($P<0.001$) than C4-HI, and 59-HI expressed higher levels of Dnmt3b and Dnmt1 ($P<0.001$) than 59-2-HI. (b)

Representative western blots for Dnmts using nuclear protein extracts. Samples processed for western blots from the same tumors that were used to show PR isoform ratio in FIG. 2 were used to evaluate Dnmts' expression. ERKs were used as loading controls. The band intensities of two different western blots of the different Dnmts were quantified in relation to the loading control. C4-2-HI expressed higher levels of Dnmt3a ($P<0.001$), Dnmt3b, and Dnmt1 (both $P<0.01$) than 59-HI expressed higher levels of Dnmt1 ($P<0.01$) and Dnmt3b ($P<0.001$) than 59-2-HI. (c) Expression of other methylation-regulated proteins. The same tumor extracts described above were also probed with antibodies to E-cadherin, Rb, PTEN, p16, and RARβ. The expression pattern of these proteins was different from the PRA expression pattern shown in FIG. 7.

FIG. 14 shows glucocorticoid receptor (GR) expression in 5azadC-treated and -untreated constitutive-resistant tumors. (a) Left Cells growing with 10% FCS were treated for 96 h with or without 5azadC ($5\times10^{-7}$ M) and processed for immunofluorescence using the GR antibody as described in "Materials and methods" section. FITC-conjugated secondary antibodies were used. PI was used for nuclear counter-staining. Right GR staining was quantified using the Image Quant software as described in "Materials and methods" section in Example 2. 5azadC induced a down regulation in GR expression in vitro; ***$P<0.001$. (b) GR expression was analyzed in the nuclear and the cytosolic extracts from control or 5azadC-treated C4-2-HI samples by western blot. ERKs were used as a loading control.

Figure 15:
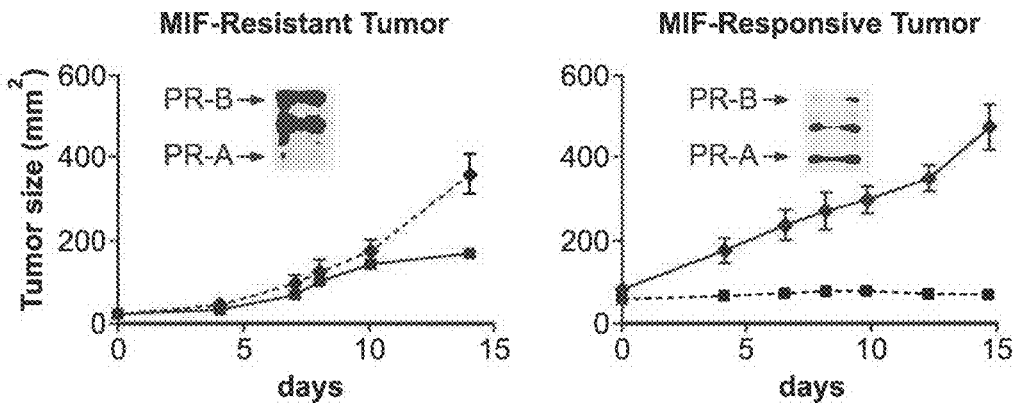

FIG. 15 shows the response to RU-486 or MIF, of two representative tumors of this experimental model: left, C4-2-HI which shows high levels of PR-B and the tumor is stimulated by MIF; right: C4-HI which shows high levels of PR-A and the tumor is inhibited by MIF.

Figure 16:
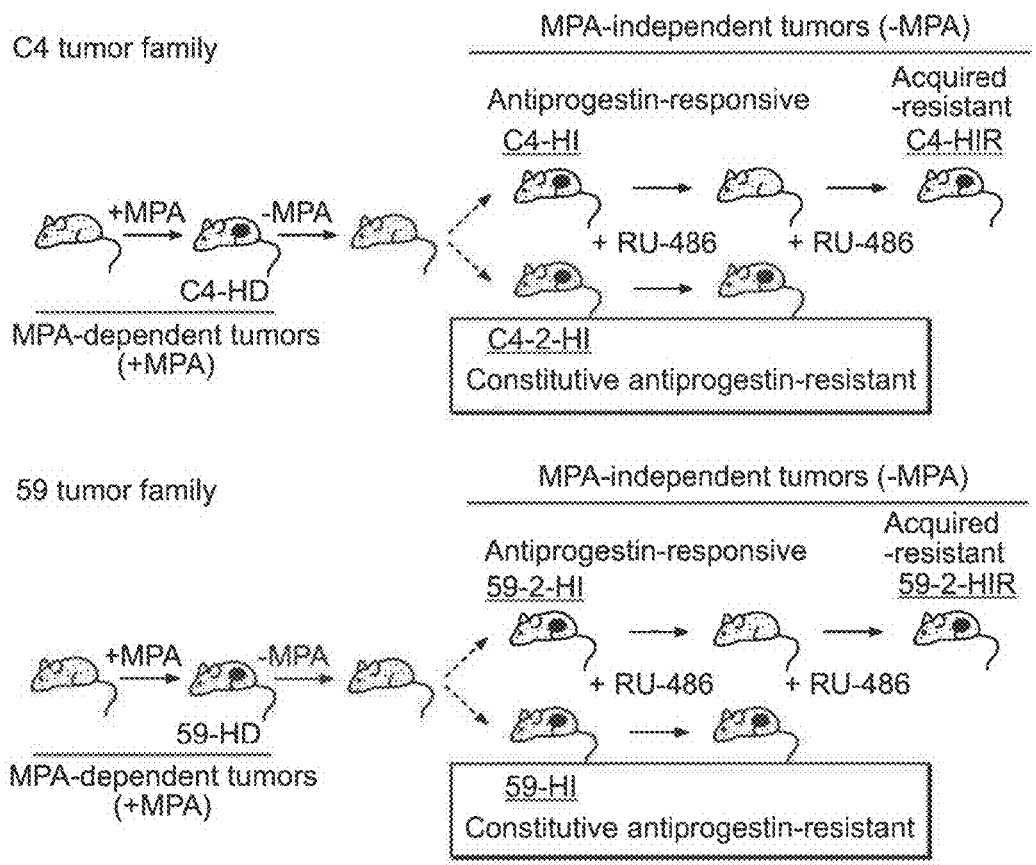

FIG. 16 provides a schematic of the C4 and 59 tumor family from the MPA breast cancer model used in Example 3.

Figure 17:
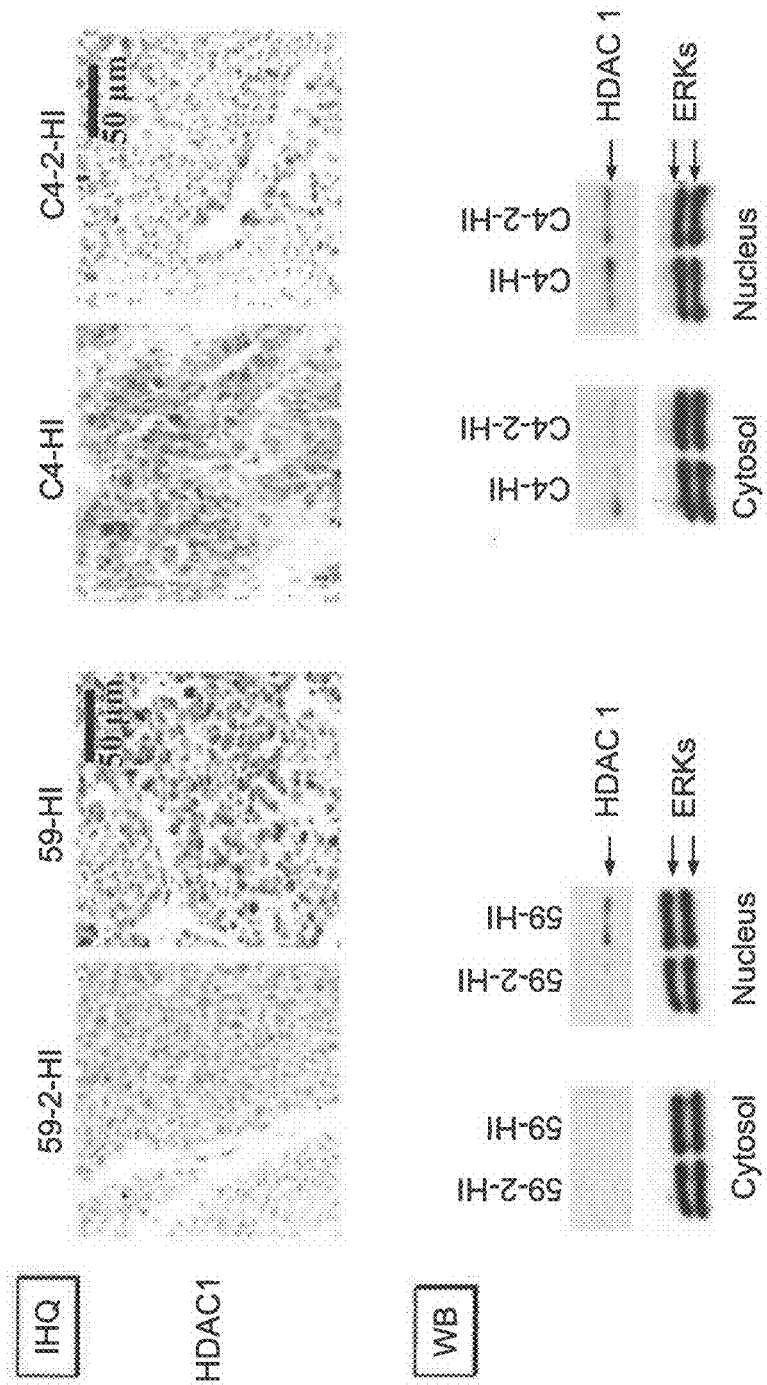

FIG. 17 shows the expression of HDAC1 in constitutive resistant tumors as measured in Example 3. The constitutive resistant tumor 59-HI showed a higher expression of HDAC-1 as compared to the antiprogestin sensitive tumor 59-2-HI ($p<0.001$).

Figure 18:
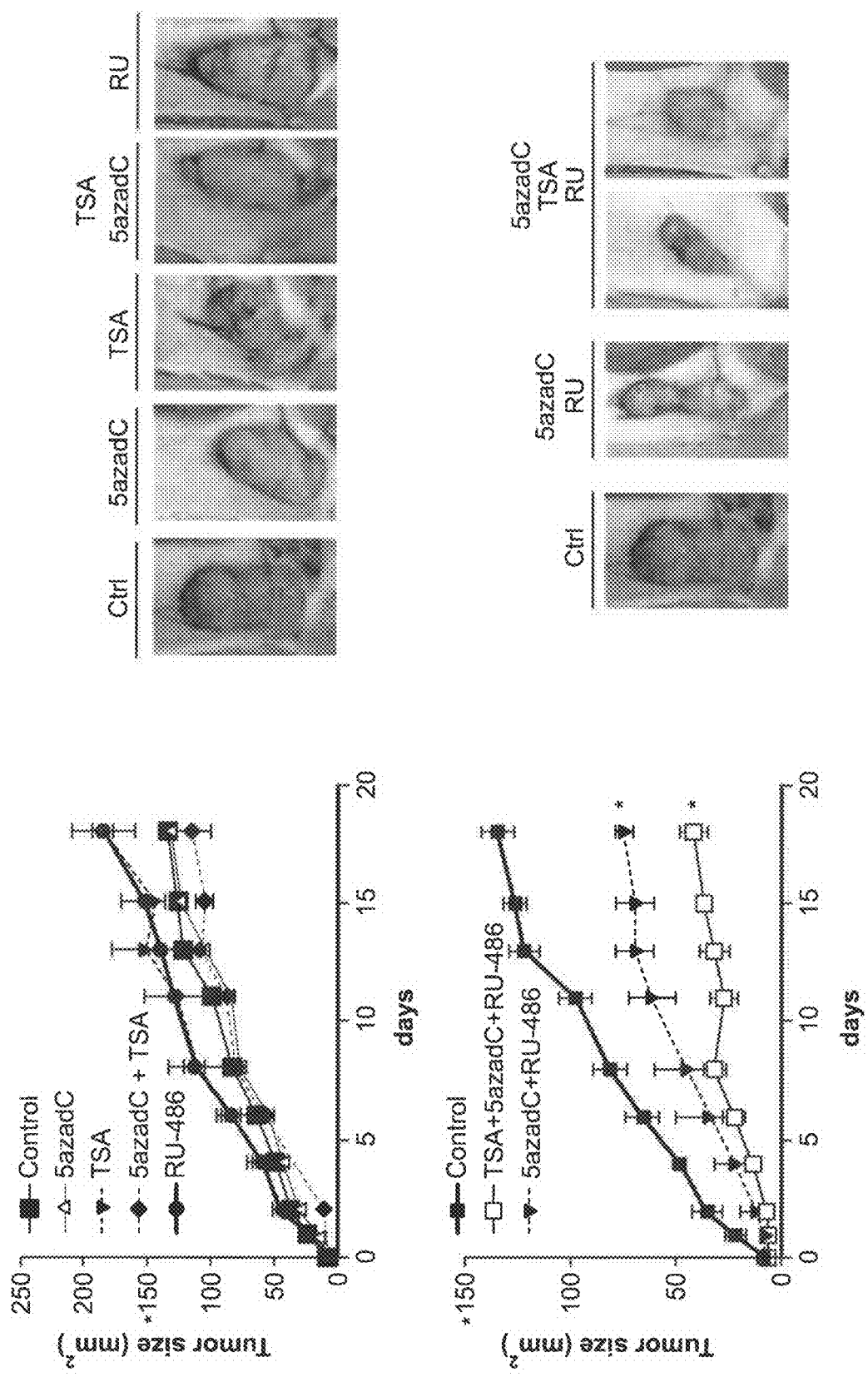

FIG. 18 shows the results of co-treatment of 5azadC (demethylating agent), TSA (HDAC inhibitor) and MIF (antiprogestin). The co-therapy induced a significant inhibitory effect that was even greater than the one induced by 5azadC plus MIF in 59-HI tumors ($p<0.01$). 5azadC: 1 mg/kg/day; TSA: 1 mg/kg/day; MIF (Ru-486): 12 mg/kg/day.

Figure 19:
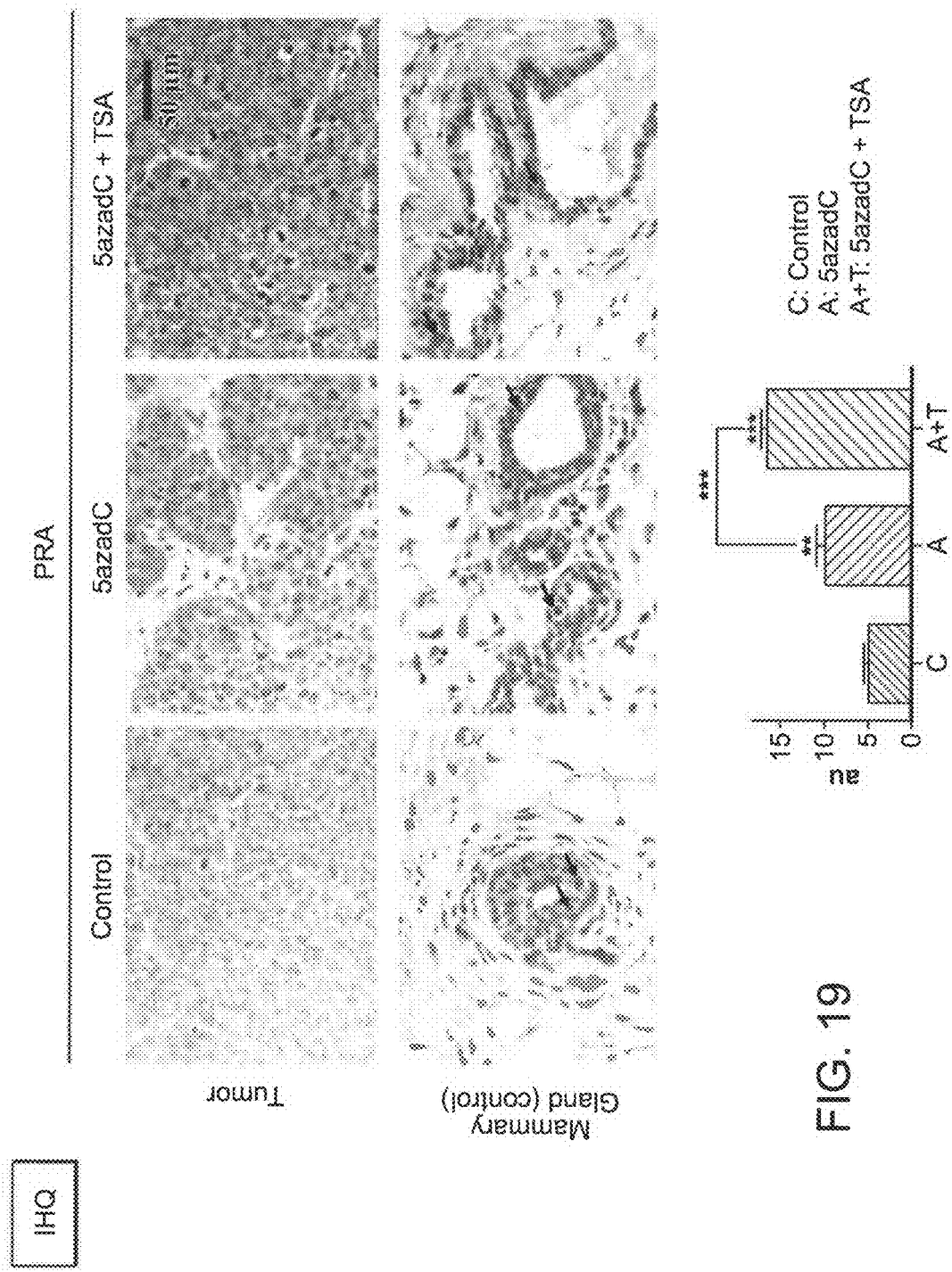

FIG. 19 provides micrographs of mammary 59-HI tumor and control cells treated with 5azadC alone, and 5azadC in combination with TSA. The data show that the increase in PRA was higher with TSA plus 5azadC than with 5azadC alone in 59-HI tumors cells ($p<0.001$).

Figure 20:
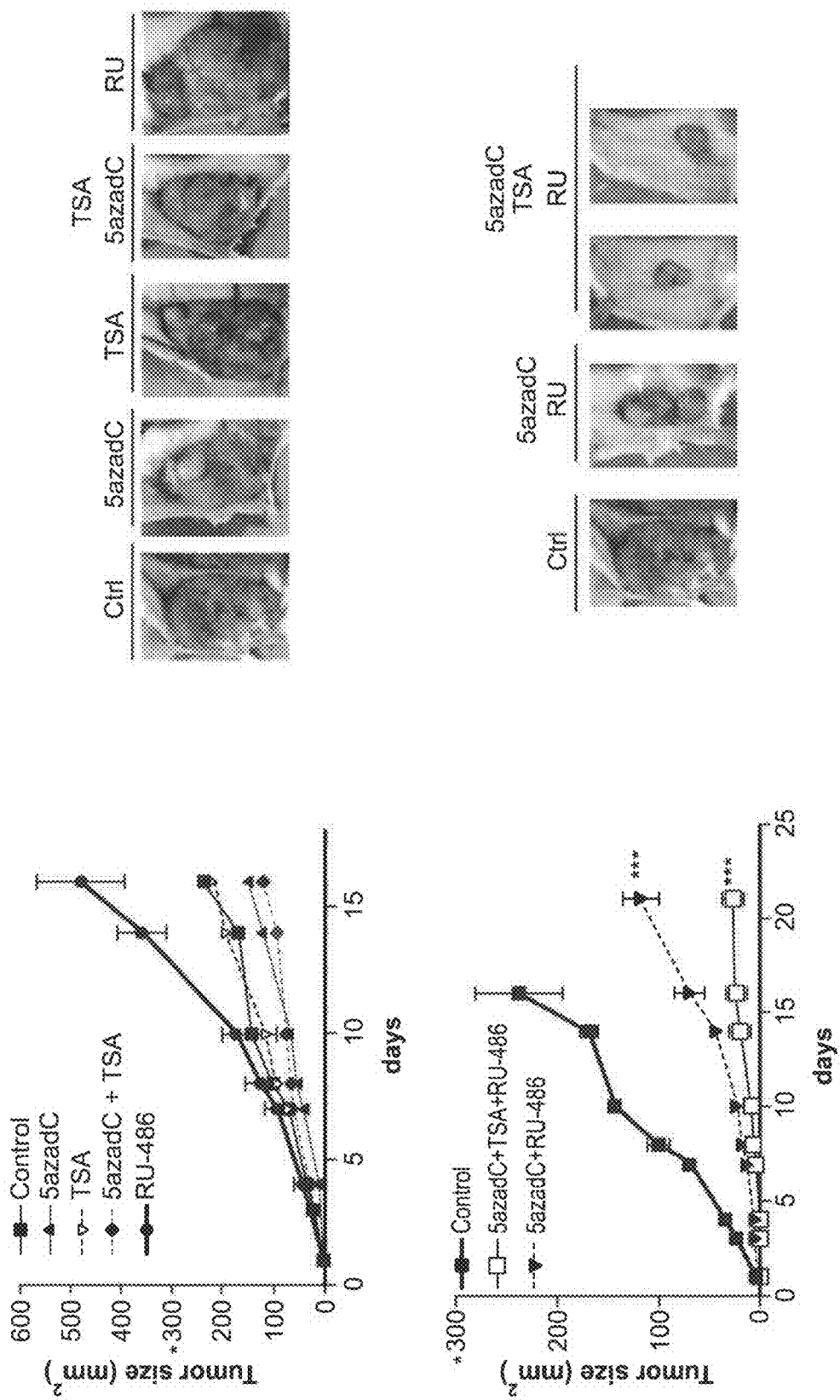

FIG. 20 shows the results of co-treatment with 5azadC, TSA and RU-486. The co-treatment of the three agents induced a significant inhibitory effect that was even greater than the one induced by 5azadC plus RU-486 in C4-2-HI tumors ($p<0.001$). 5azadC: 1 mg/kg/day; TSA: 1 mg/kg/day; MIF (Ru-486): 12 mg/kg/day.

Figure 21:
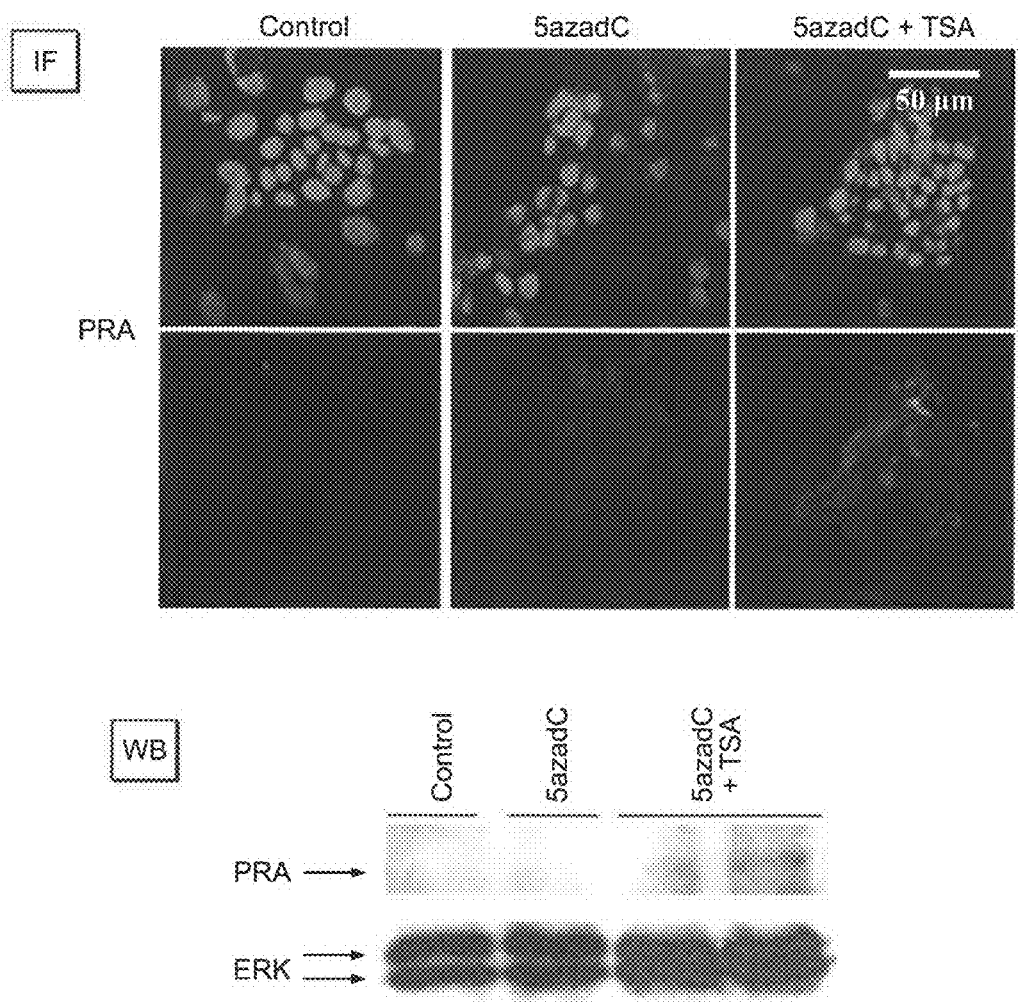
Figure 23A:
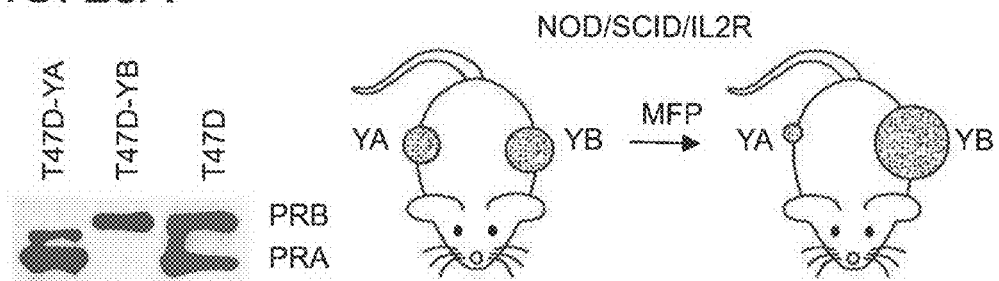
Figure 23B:
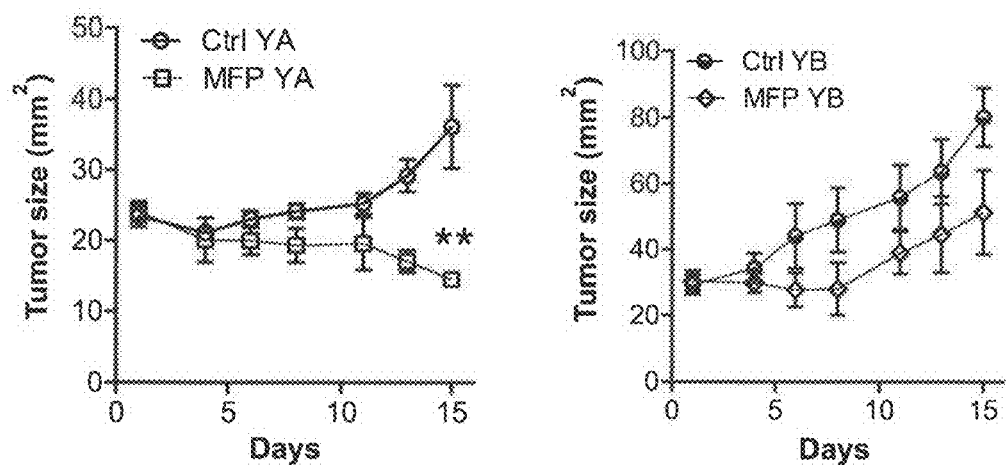
Figure 23C:
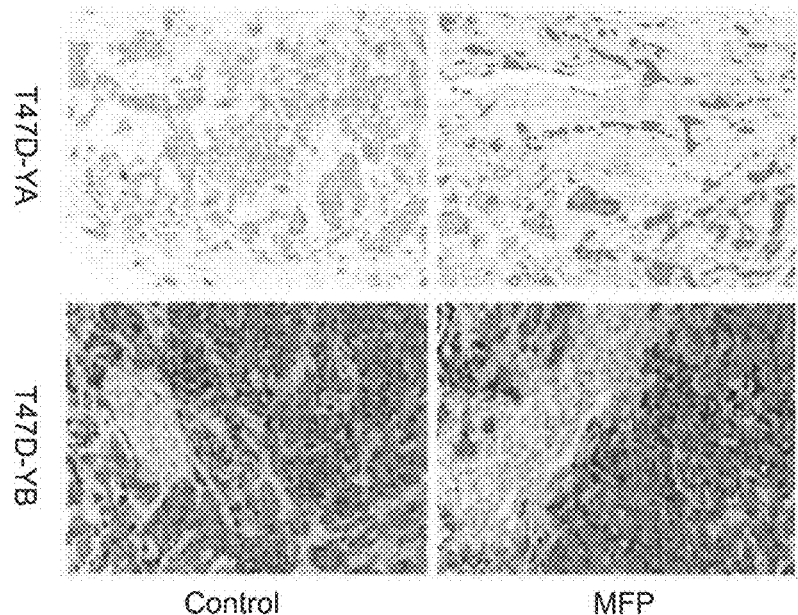
Figure 23D:
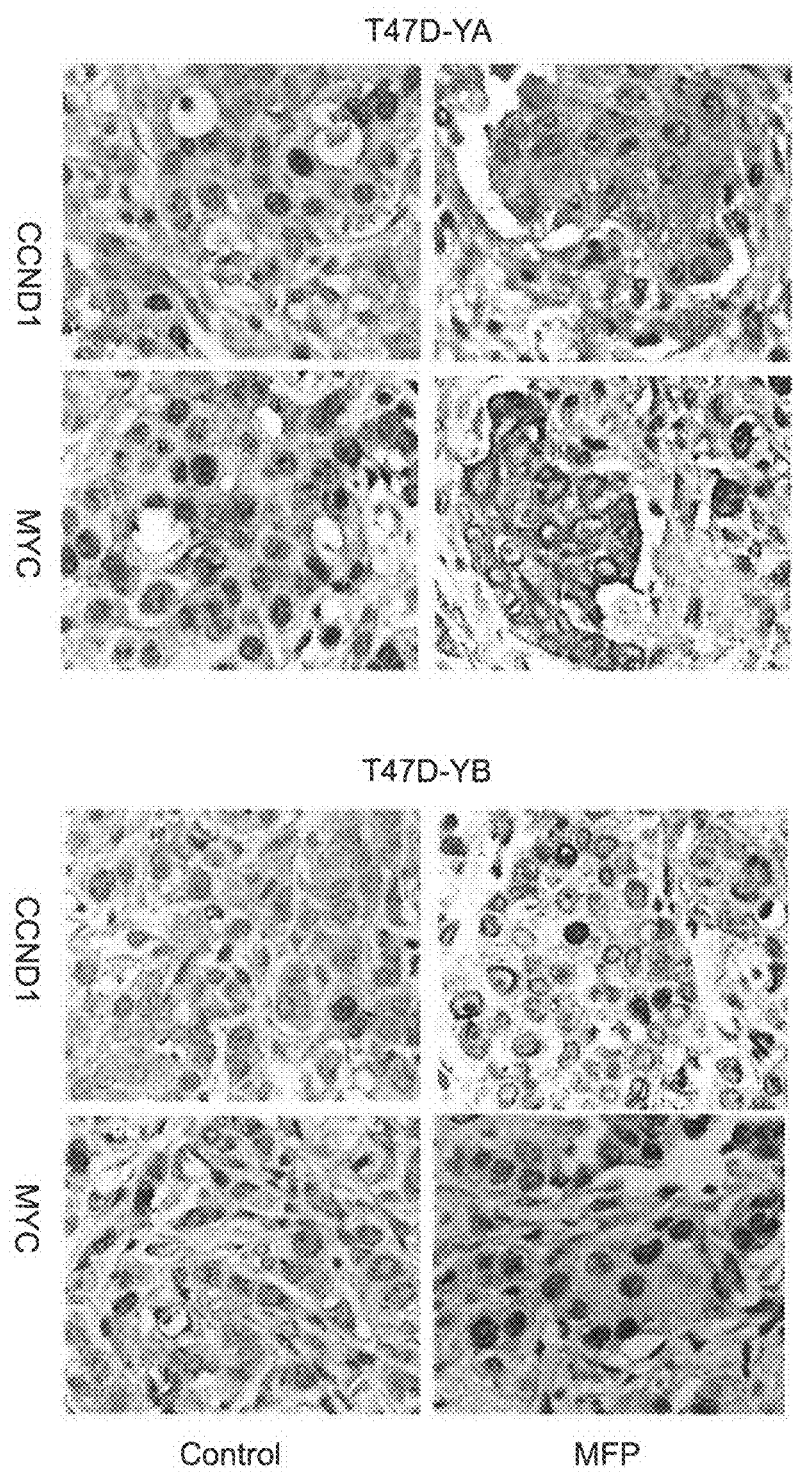

FIG. 21 provides micrographs of C4-2-HI tumor cells stained to show PRA expression. The increase of PRA expression was higher with TSA plus 5azadC than with 5azadC alone in C4-2-HI tumors.

FIG. 22 describes how antiprogestins inhibit the growth of human IBH-6 tumors overexpressing PRA.

FIG. 23 describes the effect of MFP on xenografts of T47D cells over expressing PRA or PRB.

Figure 24:
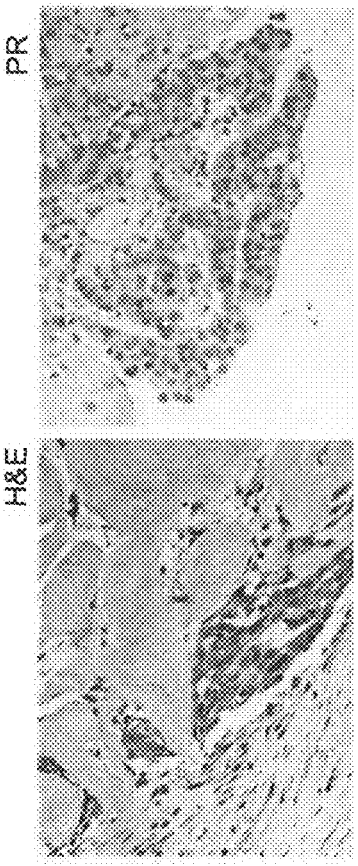
Figure 24:
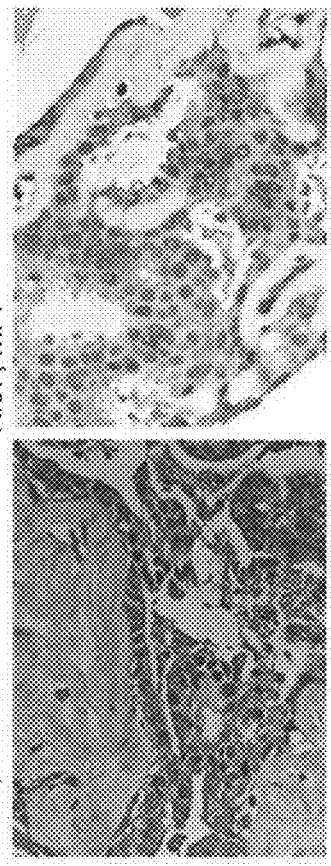
Figure 24:
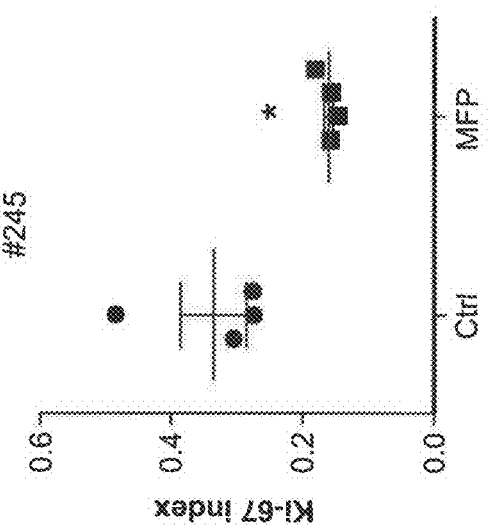

FIG. 24 describes MFP induces an inhibition of cell proliferation (evaluated as Ki67 staining) in a breast cancer sample with a PRA/PRB ratio lower than 1.

Figure 25:
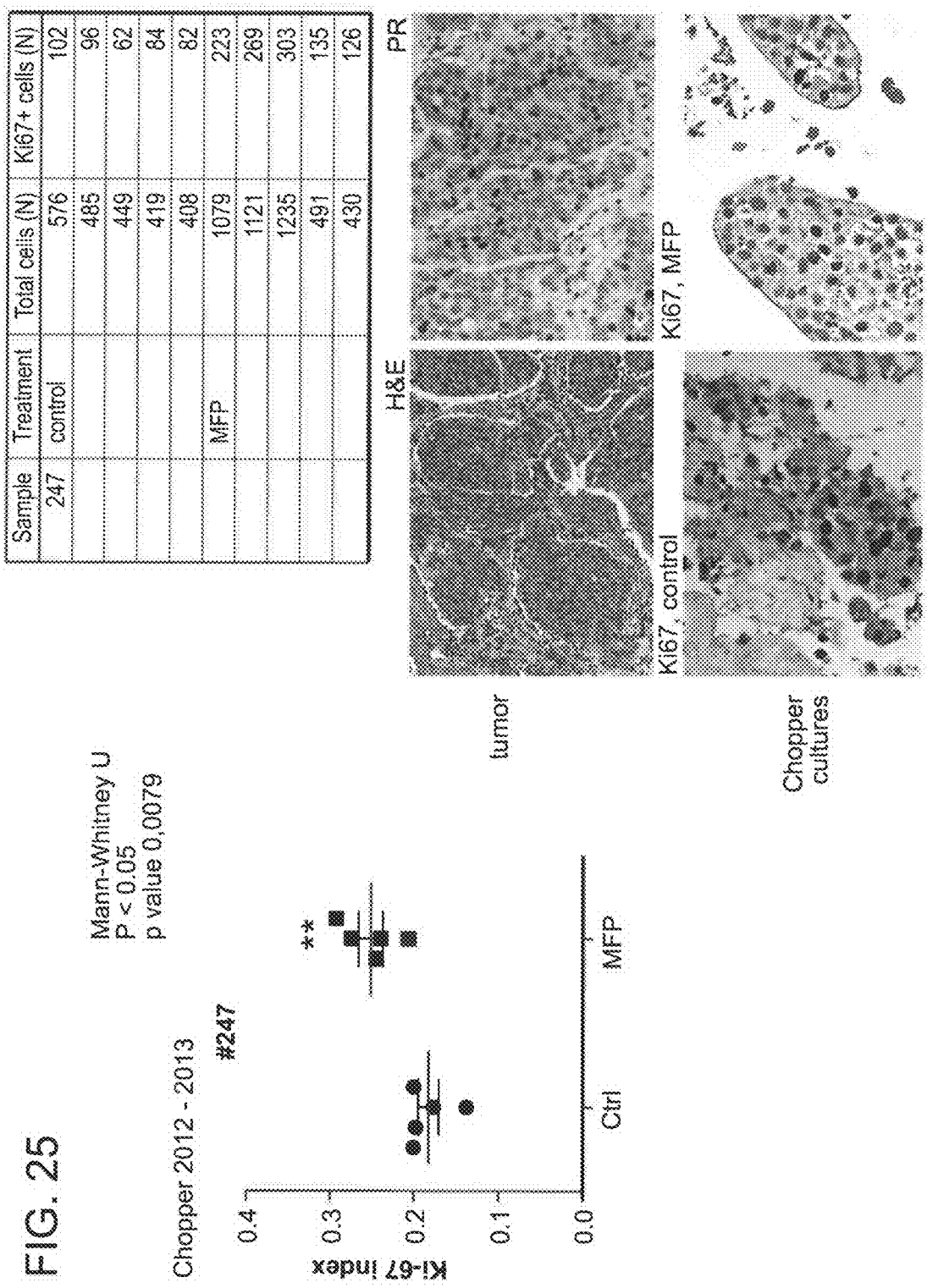

FIG. 25 describes MFP stimulated cell proliferation (evaluated as Ki67 staining) in a breast cancer sample with a PRA/PRB ratio lower than 1. The graph design is similar to FIG. 24.

Figure 26:
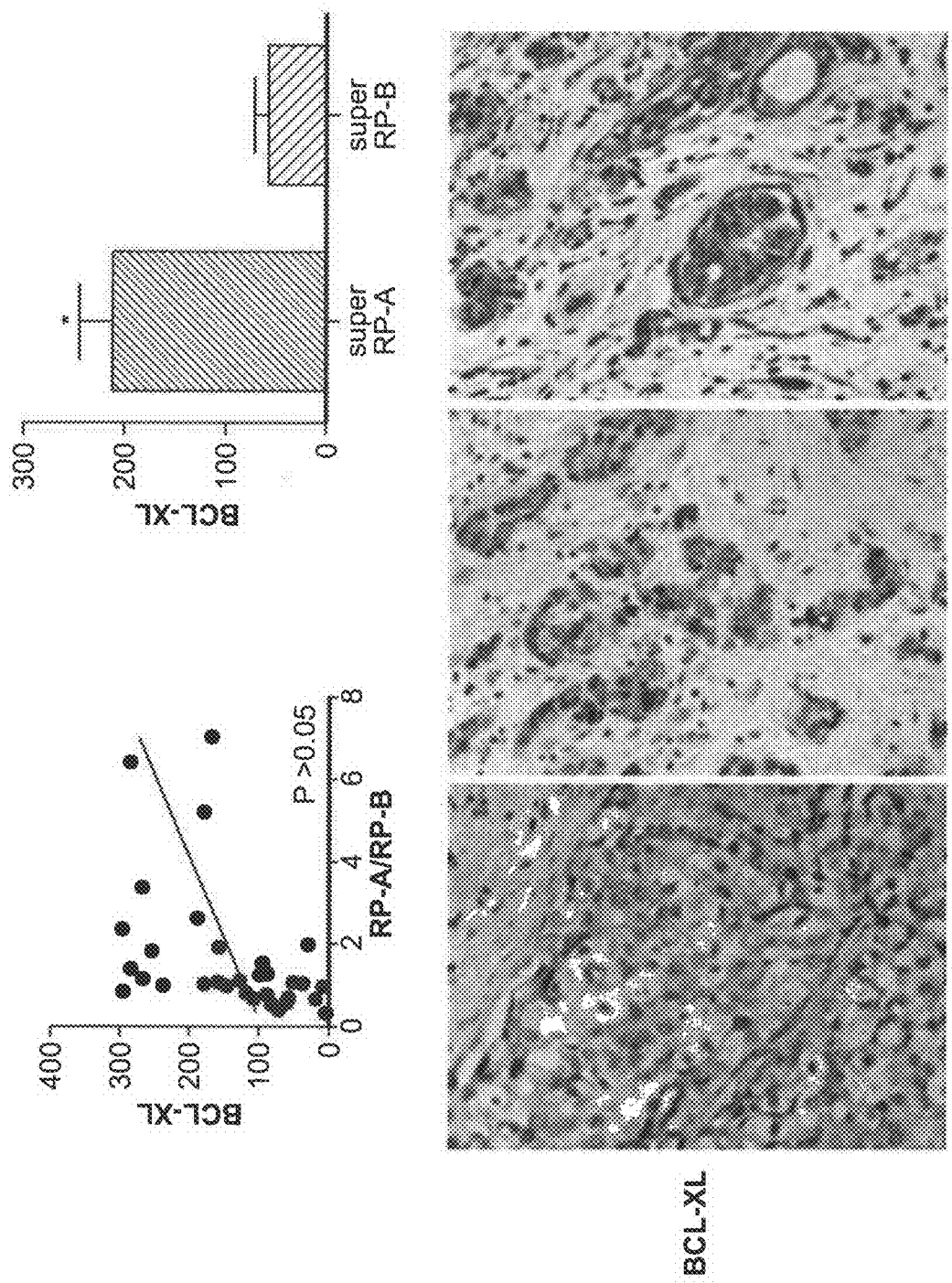

FIG. 26 describes the correlation of BCL-XL expression and PR-A expression.

DETAILED DESCRIPTION OF THE INVENTION

The present invention is based, at least in part, on the surprising discovery that carcinomas, in particular, breast carcinomas, which are PR-positive and which express a higher molar amount of PR-A relative to or compared with the molar amount of PR-B (i.e., a higher PRA/PR-B ratio) are inhibited by or are sensitive to antiprogestins, such as, RU-486 (mifepristone), whereas, in contrast, tumors which are resistant to such antiprogestins (either constitutive resistance or acquired resistance) show a higher PR-B/PR-A molar ratio. That is, cancer cells, e.g., breast cancer cells, will be resistant to antiprogestins when the molar amount of PR-B is greater than PR-A. Thus, patients with high molar amounts of PR-A (as compared to PR-B) should be those that respond to an antiprogestin treatment.

It has further been surprisingly discovered that different genetic mechanisms are responsible for resistance to antiprogestins in those tumors which show constitutive resistance (fail to respond from the beginning of treatment) to antiprogestins as compared to the tumors that acquire resistance (resistance develops after treatment begins) to antiprogestins. In particular, the inventors surprisingly discovered that constitutive resistance to antiprogestins is attributable to DNA methylation events of the gene and promoter encoding the PR-A (i.e., the PRA gene), but such is not true for acquired resistance. Accordingly, the inventors have surprisingly identified a new endocrine therapeutic strategy for using antiprogestin therapy against constitutively resistant tumors that involves blocking and/or reversing the DNA methylation events of the PRA gene, thereby restoring the increased molar ratio of PR-A to PR-B, which in turn increases the responsiveness of the constitutively resistant tumor to antiprogestins.

As demonstrated herein and in Example 2, the CpG islands located in the PRA promoter and the first exon were studied by methylation-specific PCR (MSP) in six different tumors: two antiprogestin-responsive, two constitutive-resistant, and two with acquired resistance. Only in constitutive-resistant tumors, PRA expression was silenced by DNA methylation. Next, the effect of a demethylating agent, 5-aza-2'-deoxycytidine ("5azadC") on PRA expression and antiprogestin responsiveness was evaluated. In constitutive-resistant tumors, 5azadC treatment in vitro and in vivo restored PRA expression and antiprogestin RU-486 responsiveness. Furthermore, high levels of DNA methyltransferase (Dnmts) 1 and 3b were detected in these tumors.

Moreover, as demonstrated in Example 3, the reversal effects of the demethylating agent may be further enhanced by administering in combination an HDAC inhibitor together with the demethylating agent, to improve the anti-cancer effects of antiprogestins and reverse antiprogestin-resistance.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof, and may include the compounds of the invention which are effective to increase the molar ratio of PR-A to PR-B.

By "ameliorate" is meant decrease, suppress, attenuate, diminish, arrest, or stabilize the development or progression of a disease, e.g., the size or extent of a breast carcinoma.

As used herein, the term "demethylating agent" refers any compound, antibody (or fragment thereof), drug, enzyme, nucleic acid molecule (e.g., siRNA) which effectively reverses, inhibits, blocks, or otherwise removes or leads to the removal of methyl groups from DNA, e.g., from the CpG regions of the promoter of the PRA gene. A demethylating agent can include an inhibitor of a DNA methyltransferase.

By "alteration" is meant a change (increase or decrease) in the expression levels or activity of a gene or polypeptide, e.g., PR-A or PR-B, as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that is infectious or non-infectious, and can include any type of cancer, including breast cancer.

By "effective amount" or equivalently, "therapeutically effective amount," is meant the amount of a required agent to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen of the agent. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence. Nucleic acid molecules of the invention include, but are not limited to, those encoding PR-A, PR-B, or inhibitors of PR-A or PR-B expression, or interfering RNA molecules which are inhibitory against mRNA encoding PR-A or PR-B.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, e.g., PR-A or PR-B, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Reference to "PR-A" is an acronym for progesterone receptor isoform type A.

Reference to "PR-B" is an acronym for progesterone receptor isoform type B.

As used herein, the phrase "increasing the molar ratio" refers to, as for example in "increasing the molar ratio of PR-A to PR-B," means causing there to be more moles of a first substance (e.g. PR-A) relative to the moles of a second substance (e.g., PR-B). The invention contemplates any means sufficient to cause to result in higher moles of PR-A to PR-B, including increasing the transcription level or protein expression level of PR-A (e.g., via gene therapy means to provide additional gene copies of PR-A, or via epigenetic modulations (e.g., inhibiting DNA methyltransferase)), or decreasing or inhibiting the transcription level or protein expression level of PR-B (e.g., antibody that blocks PR-B, RNA interference to block or destroy mRNA encoding PR-B).

As used herein, the term "antiprogestin" refers to a type of selective modulator of PRs (progesterone receptors), and which are classified into three groups: Type 1, Type II, and Type III. In a general sense, an antiprogestin is a substance that prevents cells from making or using progesterone (a hormone that plays a role in the menstrual cycle and pregnancy). An antiprogestin is a type of hormone antagonist.

As used herein, reference to a cancer, e.g., a breast cancer, that is "resistant" to a hormone anticancer therapy, such as an antiprogestin therapy, is in which the cells or some of the cells of the cancer are insensitive to the anticancer effects of the antiprogestin.

As used herein, reference to the term "cancer" may be interchangeable with the terms "tumor" or "carcinoma" for the purposes of this invention.

As used herein, reference to "constitutive-resistant tumors" refers to those tumors which are initially and at the outset resistant to treatment with an antiprogestin.

As used herein, reference to "acquired-resistant tumors" refers to those tumors which are initially and at the outset not resistant to treatment with an antiprogestin, but which acquire or develop resistance to the antiprogestin with time via selective pressure.

As used herein, the following terms and definitions may apply:
5azadC 5-Aza-2'-deoxycytidine
Dnmts DNA methyltransferases
E2 17-β-Estradiol
ER Estrogen receptor
ERx ER alpha
FCS Fetal calf serum
GR Glucocorticoid receptor
H&E Hematoxylin and eosin
HPF High power field
i.p. Intraperitoneal
M Methylated
MPA Medroxyprogesterone acetate
MSP Methylation-specific PCR
PI Propidium iodide
PR Progesterone receptor
PRA PR isoform A
PRB PR isoform B
RU-486 Mifepristone
s.c. Subcutaneous
UM Unmethylated
HDAC histone deacetylase As used here, reference to a cancer which is "responsive to treatment with an antiprogestin," refers to a cancer which is not resistant to an antiprogestin and can thereby be treated by the administration of a therapeutically effective amount of an antiprogestin. A cancer is "responsive" to treatment with an antiprogestin if the cancer is mitigated or reduced by some metric or measurable characteristic or phenotype, such as tumor size, metastatic properties, cancer marker expression, etc. In the case of tumor size as a metric for cancer responsiveness, the cancer is responsive to a treatment if the tumor size decrease by at least 1%, 2%, 3%, 4%, or 5%, or more preferably by at least 5%, 10%, 15%, 20%, 25%, 30%, 35%, 40%, 45%, or 50%, or still more preferably by at least 25%, 50%, 75%, 90%, 95%, or even 99%. Tumors may also be fully responsive by 100% reduction in tumor size.

Use of Antiprogestins in Breast Cancer Treatment

Breast Cancer and Hormones.

It will be appreciated that the bulk of the evidence concerning breast cancer etiology points to estrogens as the major etiological factors (Santen, et al. 2009). Available experimental and epidemiological evidence, as reviewed in recent papers (Aupperlee, et al. 2005; Horwitz 2008; Lange, et al. 2008), have also implicated the PR in breast carcinogenesis. Furthermore, the Women Health Initiative study WHI (Women's Health 2002) and the Million Women Study (Beral 2003) reported an increase in breast cancer risk in women undergoing therapy with estrogen plus a progestin, such as medroxyprogesterone acetate (MPA). These results were later confirmed in other studies (Chlebowski, et al. 2010; Chlebowski, et al. 2003).

More than 70% of breast cancers express ERs and PRs; thus, they are susceptible to adjuvant endocrine therapy. This adjuvant therapy is designed to target the ERs using antiestrogens (Jordan 2008), such as tamoxifen (TAM; Jordan 1990) or Fulvestrant [Faslodex™, ICI 182.780; (Dauvois, et al. 1993)], or by inhibiting the endogenous synthesis of 17-β-estradiol (E2) using aromatase inhibitors (Brodie, et al. 1986). Nevertheless, some of these tumors fail to respond from the very beginning (constitutive-resistant tumors), while others may acquire hormone resistance (Jordan 2008; McGuire 1975).

Because E2 regulates the expression of the PR (Kastner et al. 1990; Petz and Nardulli 2000; Petz, et al. 2002; Schultz, et al. 2003) and because there is ample evidence linking progestin to breast cancer pathogenesis, it is reasonable to utilize inhibition of the PRs as a rational target for the management of breast cancer (Moore 2004).

Progesterone Receptor.

Figure 1:
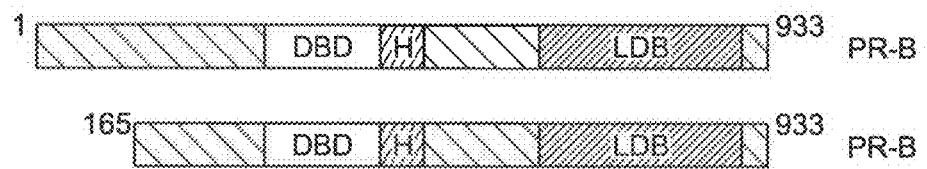
FIG. 1 is a schematic of the two isoforms of progesterone receptor (PR): isoform type A ("PR-A") and isoform type B ("PR-B").

The PR is a member of the steroid-thyroid hormone-retinoid receptor superfamily of ligand-activated nuclear transcription factors (Evans 1988; Kastner et al. 1990). Upon progesterone binding, the receptor undergoes a series of conformational changes, dimerizes and translocates to the nucleus, where it interacts with specific DNA sequences (Progesterone Response Elements, PREs) in the promoter regions of target genes (Edwards, et al. 1995; Lange et al. 2008). These transcriptional effects may also be mediated by PRE independent actions through protein-protein interactions between the PR and other sequence specific transcription factors (Leonhardt, et al. 2003). The PR, like all transcription factors, localizes to the nuclear compartment. It has also been described to be located in the cytoplasm and at the cell membrane (Bottino, et al. 2011), where it triggers non-genomic or membrane initiated signaling pathways. PR target genes encode for a wide range of proteins that control or modulate crucial cellular functions, such as cell growth, apoptosis, transcription, steroid and lipid metabolism (Li and O'Malley 2003). Two PR isoforms have been described: isoform B (PR-B), which is 933 amino acids long in humans with a molecular weight of 116 kDa, and isoform A (PR-A), which lacks 164 amino acids at the N-terminus but is otherwise identical to isoform B (MW: 94 kDa; FIG. 1 A). They are transcribed from two different promoters of the same gene on human chromosome 11 q22-q23 (Kastner et al. 1990) or on chromosome 9 in mice (band 9A1).

The presence of CpG islands in both PR promoters indicate that both isoforms may be silenced by CpG island methylation (Vasilatos, et al. 2009). In mice, the isoforms have a molecular weight of 115 and 83 kDa, respectively (Schneider, et al. 1991). When PR-A and PR-B are present in equimolar amounts in wild-type PR-positive cells or are transiently co-expressed in PR-negative cells, they dimerize and bind to DNA as three species: A/A and B/B homodimers and A/B heterodimers. Post-transcriptional modifications of the PR include phosphorylation, acetylation, sumoylation and ubiquitination (Dressing and Lange 2009; Hagan, et al. 2009). Although some sites might be basally phosphorylated, most are phosphorylated by ligand dependent or ligand-independent mechanisms. Phosphorylation affects the ability of the PRs to interact with the promoters of their target genes and the subsequent transcriptional activation of these genes (Clemm, et al. 2000). Additionally, phosphorylation affects PR subcellular localization and stability and its ability to interact with other proteins (Clemm et al. 2000).

The PR is an estrogen-regulated gene (Horwitz, et al. 1978; Kastner et al. 1990); however, consensus sequences related to the estrogen-responsive element have not been found, except for a half-site at the PR-A promoter (Kastner et al. 1990). Many of the studies on PRs, including the cloning of the human PR, were performed in T47D cells, a human breast cancer cell line overexpressing both PR isoforms (Keydar, et al. 1979). Other important information comes from genetically modified mice overexpressing either PR-A (Shyamala, et al. 1998) or PR-B and from mice lacking one or both of the isoforms (Conneely and Lydon 2000; Lydon, et al. 1995). In these knock-out (KO) models, it has been shown that these isoforms have different roles in vivo. PR-B mediates the proliferative effects of progesterone in the mammary gland (Conneely, et al. 2003; Mulac-Jericevic, et al. 2003), whereas PR-A is more important in maintaining ovarian and uterine functions.

PR-B has been considered to be a much stronger transcriptional activator than PR-A. The latter can act as a ligand repressor of other steroid receptors, including PR-B, ER, androgen receptors, glucocorticoid receptors or mineralocorticoid receptors, in a cell- and promoter dependent manner (Boonyaratanakornkit and Edwards 2007).

In T47D cells engineered to express only PR-A (T47D-YA) or PR-B (T47D-YB) (Sartorius, et al. 1994), PR-B controls the majority of the progesterone-regulated genes (~65% of the genes); 4% are regulated by PR-A, and 25% are regulated by both (Richert, et al. 2000). However, when the PR is activated in the absence of ligand, PR-A is the more active isoform (Jacobsen, et al. 2002).

Over expression of PR-A compared to PR-B is common in breast cancer (Graham, et al. 2005; Graham, et al. 1995). Furthermore, it has been associated with poorer outcome in patients undergoing hormonal therapy (Hopp, et al. 2004). Therefore, evaluation of the PR isoform ratio may be important in breast cancer prognosis and therapeutic decisions.

Antiprogestins.

The present invention contemplates any suitable antiprogestin. Selective modulators of PRs (SPRM) are classified into three groups. With Type I SPRMs, such as onapristone [ONA; ZK 98299; (Leonhardt et al. 2003)], an antagonist-bound PR does not bind to DNA. With type II SPRMs, such as mifepristone (MIF; RU-486), the complex does bind to DNA. Interestingly, type II SPRMs act as agonists if the cells are stimulated with activators of the cAMP/PKA pathway; however, this effect occurs in a PR-B tissue- and species-specific manner. PRs bound to type III modulators bind DNA and have a purely antagonistic effect, even in the presence of activated PKA. This class of SPRMs includes lonaprisan [(ZK 230211; (Afhuppe, et al. 2009)].

MIF was the first PR antagonist developed for human use. At very low concentrations (Bottino et al. 2011), or when PR-B is activated by PKA (Beck, et al. 1993), MIF behaves as an agonist. This effect does not occur when it binds to PR-A (Meyer, et al. 1990). MIF induces PR dimerization and DNA binding with an affinity higher than that of progesterone, the natural ligand (DeMarzo, et al. 1991; Skafar 1991). The inhibitory effect of MIF is related to its ability to recruit co-repressors (Jackson, et al. 1997). Additionally, MIF has antiglucocorticoid effects, albeit at concentrations higher than those needed for its antiprogestin activity (Gaillard, et al. 1984). ONA, which also displays antiglucocorticoid effects at higher concentrations, was discontinued due to hepatotoxicity (Robertson, et al. 1999).

Lonaprisan, a last-generation antiprogestin (Afhuppe, et al. 2010; Afhuppe et al. 2009), has low antiglucocorticoid activity and no effect on PKA-activated PR-B (Afhuppe et al. 2010; Chwalisz, et al. 2000; Fuhrmann, et al. 2000). Breast cancer patients are now being recruited for a phase I/II clinical trial of this compound (http://clinicaltrials.gov/ct2/show/NCT00555919).

Aglepristone (RU534), an antiprogestin approved for veterinary use (Galac, et al. 2004), binds the PR with a high affinity and the GR with lower affinity (Polisca, et al. 2010). Clinically, aglepristone is indicated for pyometra, pregnancy control and vaginal fibromas in dogs, and for the treatment of fibroadenomatous mammary hyperplasias in cats (Muphung, et al. 2009).

Other antiprogestins under development are Org 31710 and Org 31806 from Organon, as well as CDB-2914 and CDB-4124 (CDB: Contraceptive Development Branch) from the National Institute of Child Health and Human Development. Like MIF, both CDBs have 11 alpha substitutions, but in contrast to MIF, they are derivates of 19-norprogesterone. Additionally, their antiglucocorticoid activity is less than that of MIF (Attardi, et al. 2004; Attardi, et al. 2002; Hild, et al. 2000).

Other SPRMs with mixed agonistic and antagonistic activity include asoprisnil (J867) and its derivatives. These compounds were developed to have ideal SPRM activity, such that they would act both as agonists in the ovaries and as antagonists in the mammary gland and uterus (Chwalisz, et al. 2005).

Antiprogestins in Mammary Glands.

Data on the effects of antiprogestins on the normal human mammary gland are sparse. Inhibition of cell proliferation was observed in aspirates of mammary glands from postmenopausal women with leiomyomas treated with MIF (50 mg/every other day) for three months (Engman, et al. 2008).

In experimental animals, antiprogestins may induce differentiation by increasing the levels of mammary-derived growth inhibitor (Li, et al. 1995). In mice, MIF [12 µM (5 mg/kg) body weight] induced activation of the PR in luminal cells to an even greater degree than did the pure agonist R5020 (Han, et al. 2007). In BALB/c female mice, daily doses of MIF (10 mg/kg) for one week reverted MPA-induced branching; however, it resulted in duct differentiation (Cerliani, et al. 2010) when administered alone. It has also been reported that MIF is unable to revert mammary hyperplasia in PR-A transgenic mice (Simian, et al. 2006) or in FGF2-treated mice (Cerliani et al. 2010).

Antiprogestins in Breast Cancer Models.

The present invention contemplates the use of any suitable breast cancer animal model to the extent such is necessary to fully make and use the present invention.

Rats:

In certain aspects, rat models can be used. In one embodiment, rats treated with 7, 12-dimethylbenz[α]anthracene (DMBA) or N-methyl nitrosourea (MNU) can be used. In DMBA-treated animals, MIF (10 mg/kg/day for 3 weeks) delayed tumor development (Bakker, et al. 1987) and inhibited tumor growth. Antiprogestin treatment increased the levels of luteinizing hormone (LH), E2, prolactin (PRL) and progesterone but did not alter the levels of follicle-stimulating hormone (FSH), adrenocorticotropic hormone (ACTH), or corticosterone.

MIF (10 mg/kg/day) and TAM (400 µg/kg/day), in combination, induced regression of DMBA-induced mammary tumors (Klijn, et al. 1989). Two explanations were put forward to explain the increased efficacy resulting from this combined therapy. First, this improved effect could be due to the increase in PR expression induced by TAM (Horwitz 1987) allowing for a better response to MIF. Alternatively, TAM may have negated the effects of high E2 levels induced by MIF. In this model, ONA was more efficacious than MIF at the same doses (Michna, et al. 1989), although both drugs increased differentiation. Ovariectomy induced complete regression but did not affect differentiation. The SPRMs Orgs 31710 and 31806 were more effective than MIF when administered p.o. (Bakker, et al. 1990); the responses were seen in combination with LHRH agonists, buserelin or goserelin (Bakker, et al. 1989). Similar results were obtained with Org 31710 in combination with Org 33628. This antiprogestin was given p.o. and was more effective than MIF (Kloosterboer, et al. 2000). Similar results were obtained when MNU was used as a chemical carcinogen, instead of DMBA, using s.c. antiprogestin doses of 10 mg/kg/day (Michna et al. 1989). In contrast to sc administration, there were no increases in ACTH levels or the weights of the uterus, adrenals and ovaries when MIF or both ORGs were administered p.o. (Klijn, et al. 1994). Treatment with TAM increased PR expression. In contrast, administration of MIF alone induced down regulation of the PR, and the combination of TAM and MIF inhibited the expression of both the ER and the PR. Additive effects of ONA and TAM were reported in DMBA and MNU rat models (Nishino, et al. 2009). TAM administered at a concentration of 6 mg/kg/day was more efficacious than when it was administered at a dose of 10 mg/kg/day. Earlier studies had demonstrated that the combination of TAM and ONA treatment at doses of 5 mg/kg/day was more effective than either monotherapy, an effect attributed to decreased circulating progesterone levels observed in animals in the combination treatment group (Nishino et al. 2009).

Mice:

In certain other embodiments, mouse models can be used. ONA or MIF treatment (1 or 10 mg/kg/day) initiated one day post-transplantation inhibited both tumor take and the stimulatory effects of E2 and MPA in the MXT mouse model of breast cancer (Michna et al. 1989). The effects of MPA occurred at equimolar concentrations, however the progestagenic effect was dominant at higher doses. ONA proved to be better than MIF at inhibiting cell proliferation at the 10 mg/kg/day dosage. Tumor regression was associated with necrosis, cytolysis and decreased PR expression. Ovariectomy completely inhibited PR expression (Bakker et al. 1989). No significant antiglucocorticoid effects were seen and no changes in adrenal gland weight were measured (Schneider et al. 1991). Dexamethasone failed to rescue the inhibitory effects of MIF (Bardon, et al. 1985). An increase in uterine, ovary and pituitary weight was observed in antiprogestin-treated mice. Histopathological analyses of the uterus and vagina indicated an estrogenic effect, probably due to low estrogen levels (Michna et al. 1989).

Similarly, we demonstrated that BALB/c mice, in continuous estrous cycles and treated with antisense PR oligos, demonstrated a transient estrogenic effect (Lamb, et al. 2005).

Genetically Modified Mice:

Nulliparous mice null for Brca1/p53 developed mammary hyperplasias and had a high incidence of mammary carcinomas that expressed high levels of PR. MIF (pellets of 35 mg) treatment prevented the induction of either hyperplasia or carcinoma. These authors proposed the use of MIF to prevent breast cancer in BRCA+ women (Poole, et al. 2006).

Studies on Breast Cancer Cell Lines.

MCF-7 and T47D are the most widely used cell lines to study the effects of hormones and hormone antagonists. In MCF-7 cells, MIF inhibited PR-mediated cell proliferation (Bardon et al. 1985). Similarly, TAM or MIF at a concentration of 10 nM inhibited E2-induced cell proliferation (Bakker et al. 1987). These experiments were performed using tissue culture media supplemented with 10% steroid-deficient (charcoal stripped, ch) human serum.

Different results have been reported by different laboratories using T47D cells. TAM or MIF specifically inhibit E2-induced cell proliferation in T47D cells, clone 11, which are ER- and PR-positive (Horwitz, et al. 1982). Other cell lines, similarly cultured, did not show this response (Bardon et al. 1985). It has been hypothesized that the inhibitory effect of MIF could be due to the fact that antagonist-bound receptors remain bound to DNA for longer periods of time, thus impeding PR recycling (Sheridan, et al. 1988). Alternatively, the inhibitory effect caused by MIF could result from its antiestrogenic effects (Vignon, et al. 1983) or because it may have a different affinity for the PR isoforms (Meyer et al. 1990). Furthermore, progestins inhibited cell proliferation, and it has been suggested that their antiestrogenic actions were responsible for this inhibition. In both cases, entry into S phase was inhibited, and the cells were arrested in G0/G1 (Michna, et al. 1990).

Other laboratories have reported different results on the inhibitory effects of MPA and MIF on E2-induced cell proliferation. R5020 (Hissom and Moore 1987) and MIF (Bowden, et al. 1989; Jeng, et al. 1993), with the latter at micromolar concentrations, can stimulate the proliferation of T47D and MCF-7 cells. The estrogenic effect of MIF at these high concentrations was probably due to the short length of the group associated with the aromatic nucleus at position 11 beta (Jeng et al. 1993). Progestins (MPA) and antiprogestins (MIF and ONA) can exert inhibitory effects on T47D cells, in the presence of 5% FCS (Murphy, et al. 1994; Murphy and Dotzlaw 1989).

Type II antiprogestins, such as MIF, had similar or greater PR affinity than the agonist itself; however, the agonistic effect was inhibited at equimolar concentrations, suggesting that there are different levels of regulation in addition to receptor binding. Mixed agonist-antagonist dimers of the PR did not bind to DNA (Edwards et al. 1995). MIF-bound PR was able to bind to DNA, however, and with a greater affinity than the agonist-bound PR. In contrast, type I antagonists permitted PR dimerization; however, they bound DNA with a very low affinity, which suggests different conformational changes are induced by different PR antagonists. T47D cells transfected with reporter genes (MMTV-CAT) clearly showed that when these cells are treated with analogs of cyclic AMP, MIF exerts an agonistic effect (Beck et al. 1993; Sartorius, et al. 1993). In this experimental setting, ONA still behaved as an antagonist (Edwards et al. 1995). These conflicting experiments may have contributed to the decreased clinical interest in these drugs.

El Eterby et al. demonstrated that MIF and TAM co-treatment increased apoptosis levels (increase in DNA laddering, decrease in Bcl-2, PKC translocation and increase of TGF-β1) (El Eterby, et al. 2000). The authors, however, used concentrations as high as 1 µM for TAM and 10 µM for MIF, making it impossible to distinguish between specific and non-specific PR-mediated effects.

Similarly, Hyder et al. demonstrated that progestins stimulate the synthesis of vascular endothelial growth factor (VEGF), which plays an important role in tumor angiogenesis (Hyder, et al. 1998). This effect was also blocked with micromolar concentrations of MIF in cells carrying p53 mutations, such as T47D and BT474 cells, but not in cells expressing wild-type p53, such as MCF-7 cells (Liang, et al. 2005). A similar regulatory mechanism was shown for thrombospondin-1 (TSP-1; Hyder, et al. 2009). Cytostasis and apoptosis (both the intrinsic and extrinsic pathways) were induced at micromolar MIF concentrations (Gaddy, et al. 2004). MIF has been shown to inhibit progesterone-induced cell proliferation in MCF-7 cells at nanomolar concentrations (Calaf 2006).

MIF treatment (100 nM) increased cell proliferation in T47D-YB cells and induced phosphorylation of ERK, which resulted in increased cyclin D1 expression via non-genomic mechanisms (Skildum, et al. 2005). Micromolar concentrations of MIF have also been shown to be associated with decreased Rb activity. Recently, it has been suggested that all of the effects of MIF at micromolar concentrations may be mediated through non-genomic mechanisms (Fjelldal, et al. 2010). A recent study demonstrated that lonaprisan (10 nM) induces apoptosis in T47D cells with a concomitant increase in p21 levels (Busia, et al. 2011). While it is known that both progestins and antiprogestins increase the expression of p21 (Bottino et al. 2011), the induction by progestins may be transient (Busia et al. 2011).

Xenotransplants of Human Cell Lines.

E2-induced proliferation of MCF-7 xenografts in athymic BALB/c mice was inhibited by MIF (50 mg/kg/day) or ONA (30 mg/kg/day) administered for 17 days (El Eterby, et al. 1998). Combination treatment with TAM (15 mg) increased this inhibitory effect. MIF (25 mg) can prevent the growth of BT-474 and T47D xenografts in nude mice that had been previously treated with E2 followed by MPA (Liang, et al. 2007). Additionally, previous studies have shown that E2 induces tumor regression, TAM inhibits tumor growth, ONA has no effect and ZK 112993 (a different antiprogestin) significantly inhibits the growth of T61 human tumors that are maintained by serial transplants in nude mice (Schneider, et al. 1990).

Antiprogestins in Different Experimental Neoplasias.

The variable inhibitory and stimulatory effects attributed to high concentrations of MIF in cells expressing the PR complicates the interpretation of the data from these different studies. Edwards et al. (Edwards et al. 1995) demonstrated that equimolar concentrations of agonists and antagonists exert inhibitory effects. It seems that MIF, at concentrations of 1 µM or higher, may also induce non-specific effects that may be masking PR-mediated actions. The same principle holds true in xenograft models. MIF (50 mg/kg/day) was shown to be inhibitory not only in MCF-7 cells but also in prostate (el Eterby et al. 2000) and ovarian cancer xenografts (Goyeneche, et al. 2007). Lower concentrations of antiprogestins should be used if more specific effects are desired, as reported in the rat and mouse models. It is possible that antiglucocorticoid/antiandrogenic effects may also participate in the non-specific growth inhibition described above. Furthermore, it is also possible that antiprogestins may be combined with chemotherapy due to their inhibition of the multidrug resistant proteins (Gruol, et al. 1994; Lecureur, et al. 1994).

MIF: Clinical Uses.

MIF has been used for different obstetric indications, such as uterine ripening and intrauterine fetal death, at doses of 200 mg/day prior to the vacuum aspirate or in doses of 850-600 mg for 48 h with very low side effects compared to prostaglandins (Ulmann and Dubois 1988). MIF at a dose of 200 mg/12 h increased the percentage of women with spontaneous delivery. The first trial using MIF for abortion purposes was launched in 1981 (Herrman, et al. 1982). Its use was advocated for different oncological applications, including breast cancer, prostate cancer, cervical cancer, meningiomas and leiomyosarcoma; Engman et al. 2008; Grunberg, et al. 2006; Grunberg, et al. 1991; Spitz, et al. 2005; Yoshida, et al. 2010). Additionally, it has potential use in different psychiatric disorders, including depression and Alzheimer's; however, in those diseases the antiglucocorticoid function seems to be more important (Benagiano, et al. 2008).

Antiprogestins in Breast Cancer Treatment.

Twelve years after the first description of the role of the PR in breast cancer (Horwitz and McGuire 1975), the first clinical trial to evaluate antiprogestin therapy in patients recruited 22 patients for a third-line study (Romieu, et al. 1987). Each patient had TAM-resistant metastases and had failed to respond to previous chemotherapy and hormone therapies. All study patients were either postmenopausal or had been oophorectomized, and they were treated with 200 mg/day of MIF for 1-3 months. Treatment efficacy was evaluated according to clinical parameters and follow-up levels of carcinoembryonic antigen (CEA). There was an 18% response rate following 3 months of therapy. The long-term tolerance was good, and there was an increase in cortisol coupled with a slight decrease in potassium levels. The results of a second trial were reported in 1989 (Klijn et al. 1989). Eleven patients with metastases who had received TAM as a first-line therapy were treated with daily doses of 200-400 mg MIF p.o., regardless of their response to TAM; some patients received progestins after MIF as a third-line therapy. There was an objective response in one patient, six patients showed temporal stabilization, and four patients had progressive disease. E2, ACTH, cortisol, and androstenedione serum levels were increased in all patients. The authors suggested that the increase in E2 may be due to aromatization of androstenedione, and therefore, they proposed a combinatorial treatment of MIF and TAM to counteract the effects of E2.

Results from a third study, in which 28 postmenopausal PR+ patients were recruited, were described in 1996 (Perrault, et al. 1996). These patients were given 200 mg/day of MIF for more than 8 weeks (median: 12.4 weeks). Low-grade side effects were reported in most patients: 68% lethargy, 39% anorexia, 29% vomiting, 50% hot flashes and 32% skin rash. Only 3 patients showed a partial response, which indicates a poor overall response rate to the therapy, especially considering that only PR+ patients were pre-selected. All patients were at advanced stages of their disease with metastases when the treatment was initiated.

A fourth clinical trial with ONA, initiated in 1995, accrued 30 breast cancer patients (Robertson et al. 1999). However, the trial had to be stopped while they were recruiting the 19$^{th}$ patient due to liver function test abnormalities. All 19 patients opted to continue with the trial. Two-thirds showed clinical signs of tumor regression: 56% showed partial response, and 11% had stable disease, percentages that are very similar to those obtained with TAM or progestin treatment. The authors emphasized that ONA, however, did not increase circulating E2 levels.

Klijn et al. reviewed these 4 studies together with unpublished results from a fifth study (Klijn, et al. 2000). There are no other published clinical results for breast cancer treatment using antiprogestins. However, two clinical trials are currently recruiting for preoperative evaluation of antiprogestins in early stage breast cancer (ClinicalTrials.gov Identifier: NCT01138553, testing MIF, and NCT00555919, Schering, testing lonaprisan).

MIF for the Treatment of Other Neoplasias.

MIF (200 mg/day for 2-31 months) has been used to treat meningiomas. Five out of thirteen tumors responded after one year, with some showing signs of regression within 2-3 months (Grunberg et al. 1991). A later study by the same authors showed less promising results; however, the lack of serious side effects still merited the use of MIF (Grunberg et al. 2006; Spitz et al. 2005). They proposed to combine MIF and dexamethasone treatment during the first 2 weeks to avoid the antiglucocorticoid effects of MIF.

In 2008, a clinical trial with MIF (50 mg/every other day) in leiomyomas showed low levels of E2 and progesterone and slightly higher concentrations of testosterone and androstenedione (Engman et al. 2008). Other SPRMs, such as asoprisnil and CDB-2914, were used for the treatment of non-surgical leiomyomas (Yoshida et al. 2010); their therapeutic effects may be attributed to their agonistic properties.

More recently, two papers have reported on the effects of MIF (200 mg/day) in patients with thymic epithelial cell carcinoma, transitional cell carcinoma of the renal pelvis, leiomyosarcoma, colon adenocarcinoma, pancreatic adenocarcinoma and malignant fibrous histiocytoma (Check et al. 2010). Improvements and pain relief were observed in all patients. The non-specific effects of MIF in these diseases may be related to progestin-mediated induction of apoptosis and an increased activation and recruitment of NK cells, which also express the PR (Arruvito et al. 2008).

Contributions of the MPA Murine Breast Cancer Model.

An experimental model of breast cancer was developed by the inventors with continuous administration of MPA to female BALB/c mice (Lanari, et al. 2009; Lanari, et al. 1986; Molinolo, et al. 1987). The main features of this tumor model were recently reviewed (Lanari et al. 2009). Briefly, most tumors that develop in the mice are luminal ductal mammary carcinomas that express high levels of both the ER and PR. The tumors metastasize to regional lymph nodes and the lungs and are maintained by serial syngeneic transplants (Lanari, et al. 1989). Initially, all behave in a progestin-dependent manner, but after a few passages, progestin-independent (HI) variants may emerge. These HI variants still retain high levels of the ER and PR (Molinolo et al. 1987), and they grow similarly in ovariectomized or non-ovariectomized mice (Kordon, et al. 1990; Lanari et al. 1989). Hormone-dependent tumors only grow in animals treated with MPA; however, FGF2 (Cerliani et al. 2010; Giulianelli, et al. 2008), TNFα (Rivas, et al. 2008) or 8-CI-cAMP (Actis, et al. 1995) may replace MPA to stimulate tumor growth in vivo.

HI-responsive tumors regress with MIF, ONA or lonaprisan treatment at daily doses of 10 mg/kg (Helguero, et al. 2003; Montecchia, et al. 1999; Wargon, et al. 2008) or with aglepristone treatment at a dose of 3 mg/week (unpublished data). The role of the PR in the antiprogestin induced effect was confirmed using antisense PR oligonucleotides to knockdown PR expression in vivo (Lamb et al. 2005). These tumors may also regress with E2 treatment (0.5-5 mg), almost as well as with antiprogestin treatment. Additionally, tumor growth was inhibited by TAM treatment. Some HI tumors are resistant to these treatments, but they still express hormone receptors. We have demonstrated that constitutively resistant tumors show PR-A silencing due to methylation of the PR-A promoter. Using selective pressure, we have been able to derive antiprogestin-resistant variants from antiprogestin-sensitive HI tumors. Interestingly, PR-A is down regulated in both constitutive (Helguero et al. 2003) and acquired antiprogestin-resistant carcinomas (Wargon et al. 2008). Upon estrogen or tamoxifen treatment, tumors with acquired resistance may revert to the antiprogestin responsive phenotype (131). In constitutive resistant tumors, however, co-treatment with demethylating agents to increase PR-A expression is necessary for reacquisition of antiprogestin responsiveness (Wargon, et al. 2010).

C4-HI is one of the HI-responsive variants and C4-2-HI is the constitutive resistant variant (Lanari et al. 2009). C4-HI is completely inhibited by MIF (FIG. 15), and these tumors have higher levels of PR-A than PR-B. Conversely, C4-2-HI only expresses PR-B and is stimulated by MIF; an effect exclusive to this tumor because in other constitutive variants, MIF treated tumors behaved in a manner similar to the controls. These results underscore the relevance of evaluating the PR isoform prior to administering an antiprogestin to breast cancer patients.

Although a dose of 10-12 mg/kg/day was used for all antiprogestins or a unique 6 mg pellet of MIF, inhibitory effects were also achieved using 1 mg/kg/day of MIF. All animals treated with MIF or as RP showed a continuous estrous cycle. The fact that the systemic actions of as PR were similar to those of antiprogestins clearly indicates that this is an indirect effect due to a pure antiprogestin effect. We have not yet evaluated whether circulating E2 levels are increased following MIF treatment.

In primary cultures of responsive tumors, we showed that 1-100 nM concentrations of MIF, ONA or lonaprisan inhibited MPA-induced or FGF2-induced cell proliferation (Dran, et al. 1995; Lamb, et al. 1999). As reported by others (Edwards et al. 1995), inhibitory effects were observed when using equimolar concentrations of agonists and antagonists.

Another interesting observation was that MIF inhibited cell proliferation, while it increased ERK phosphorylation. This led us to hypothesize that the non-genomic actions or membrane-initiated effects of progestin and antiprogestins may occur at lower concentrations than those needed to elicit genomic effects. Furthermore, if MIF stimulated ERK through nongenomic mechanisms, then the proliferative effects should be observed at low MIF concentrations. In fact, we demonstrated that very low concentrations of MIF (10-12 M) were able to stimulate cell proliferation. In vivo, concentrations 104-times lower than those that exerted growth inhibitory effects stimulated C4-HI growth (Bottino et al. 2011). These results indicate that concentrations high enough to elicit a genomic response could be used for therapeutic purposes.

Antiprogestin-Induced Tumor Regression.

Tumor regression induced by antiprogestins or E2 is a complex phenomenon involving stromal-parenchymal interactions. Increased cytostasis and apoptosis are the hallmarks of hormone-induced regression. The early events consist of increases in p21, p27 and p53 expression followed by a later decrease in hormone receptor expression (Vanzulli, et al. 2002; Vanzulli, et al. 2005). This suggests that the decrease in hormone receptor expression is not the primary event that triggers regression. Certain tumors also show an increase in differentiation (Wargon et al. 2008); in these cases, there is a less evident increase in apoptosis. The stromal tissue shows signs of activation, including the translocation of β-catenin to the nucleus in carcinoma-associated fibroblasts and an increase in laminin, collagen I and collagen IV deposited in the interstitial space between the tumor cells.

Figure 2A:
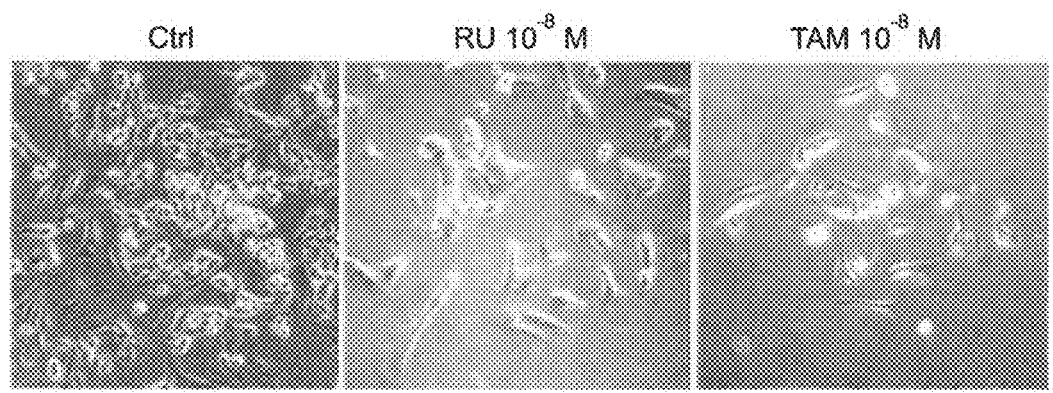
FIG. 2 relates to an embodiment of the invention, as described in Example 1, which shows that treatment with RU-486 induced a decrease in cell proliferation in tumor breast samples (tumor identified as tumor #137), or induced no change (tumor identified as tumor 171).
Figure 2A:
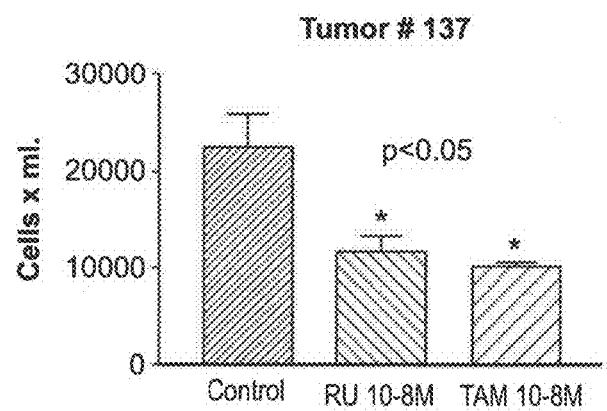

This is also associated with increases in metalloproteases 2 and 9 (Simian et al. 2006). In FIG. 2A (left), we show a representative image of a 59-2-HI tumor following MIF-treatment. This is a poorly differentiated adenocarcinoma with few connective tissue strands (control). After treatment, the tumor regresses, and the epithelial component is replaced by dense connective tissue with few remaining epithelial clusters. C4-HI is a moderately differentiated adenocarcinoma (left, upper picture). Following MIF treatment, an increase in differentiation with numerous glandular structures is observed. In FIG. 16B, we show growth curves of C4-HI treated with TAM, Fulvestrant, an FGFR inhibitor (PD 173074) or MIF. This experiment provides evidence that targeting the PR is an effective therapeutic approach in these tumors. It is possible that all other treatments, in combination with MIF, may delay the onset of hormone resistance.

The clinical and experimental data reviewed herein strongly suggest that antiprogestins may be more efficacious than tamoxifen in a subgroup of breast cancer patients. The challenge is to categorize all of the biomarkers that are necessary to identify these patients. Although there is not much information on potential biomarkers, high expression of PR-A, coupled with genes up regulated by progesterone treatment in T47D-YA cells, such as BCL-XL, ERRalpha1, HEF1 or DSIPI, may be excellent candidates.

Cancer Subjects Treatable by the Methods of the Invention

The present invention contemplates any suitable cancer subject that may be treated by the methods of the invention. In certain aspects, the subjects have breast cancer. In other aspects, the subjects can have a non-breast cancer. One aspect is that the cancer, tumor, or carcinoma is or can be altered to be responsive to an antiprogestin, such as, a Type I, Type II, or Type III antiprogestin. Such antiprogestins can include, for example, onapristone, mifepristone (RU-486), lonaprisan, aglepristone (Ru-534), Org31710, Org31806, CDB-2914, or CDB-4124.

In preferred embodiments, the methods and compositions of the invention are intended for subjects (men or women) having breast cancer, and wherein the breast cancer is or can be modified to be responsive to an antiprogestin.

Breast cancer can begin in different areas of the breast—the ducts, the lobules, or in some cases, the tissue in between.

Ductal carcinoma in situ (DCIS) is the most common type of non-invasive breast cancer. Ductal means that the cancer starts inside the milk ducts, carcinoma refers to any cancer that begins in the skin or other tissues (including breast tissue) that cover or line the internal organs, and in situ means "in its original place." DCIS is called "non-invasive" because it hasn't spread beyond the milk duct into any normal surrounding breast tissue. DCIS isn't life-threatening, but having DCIS can increase the risk of developing an invasive breast cancer later on.

When you have had DCIS, you are at higher risk for the cancer coming back or for developing a new breast cancer than a person who has never had breast cancer before. Most recurrences happen within the 5 to 10 years after initial diagnosis. The chances of a recurrence are under 30%.

According to the American Cancer Society, about 60,000 cases of DCIS are diagnosed in the United States each year, accounting for about 1 out of every 5 new breast cancer cases.

Invasive ductal carcinoma (IDC), sometimes called infiltrating ductal carcinoma, is the most common type of breast cancer. About 80% of all breast cancers are invasive ductal carcinomas. Invasive means that the cancer has "invaded" or spread to the surrounding breast tissues. Ductal means that the cancer began in the milk ducts, which are the "pipes" that carry milk from the milk-producing lobules to the nipple. Carcinoma refers to any cancer that begins in the skin or other tissues that cover internal organs—such as breast tissue. All together, "invasive ductal carcinoma" refers to cancer that has broken through the wall of the milk duct and begun to invade the tissues of the breast. Over time, invasive ductal carcinoma can spread to the lymph nodes and possibly to other areas of the body. According to the American Cancer Society, more than 180,000 women in the United States find out that they have invasive breast cancer each year. Most of them are diagnosed with invasive ductal carcinoma. Although invasive ductal carcinoma can affect women at any age, it is more common as women grow older. According to the American Cancer Society, about two-thirds of women are 55 or older when they are diagnosed with an invasive breast cancer. Invasive ductal carcinoma also affects men.

Treatable breast cancers can also include other types of invasive carcinomas which are less common, including tubular carcinoma of the breast, medullary carcinoma of the breast, mucinous carcinoma of the breast, papillary carcinoma of the breast, and cribriform carcinoma of the breast.

The present invention contemplates treating any type of cancer, and especially any type of breast cancer, in men or women, which express the progesterone receptor (PR) and which is responsive to an antiprogestin or which can be modified to be responsive to an antiprogestin. In a preferred embodiment, the invention relates to methods and compositions for treating breast cancers which are constitutively resistant to antiprogestin treatment, and which methods involve co-administering a demethylating agent to increase the molar ratio of PR-A to PR-B such that the molar amount of PR-A is greater than the molar amount of PR-B.

Pharmaceutical Therapeutics

The present disclosure provides pharmaceutical compositions that comprise an antiprogestin and in certain embodiments, also a demethylation agent, for treating cancers, especially breast cancers, which are constitutively resistant to antiprogestin therapies. For therapeutic uses, the compositions or agents identified using the methods disclosed herein may be administered systemically, for example, formulated in a pharmaceutically-acceptable carrier or delivery vehicle. Preferable routes of administration include, for example, subcutaneous, intravenous, intraperitoneally, intramuscular, or intradermal injections that provide continuous, sustained levels of the drug in the patient. Treatment of human patients or other animals can be carried out using a therapeutically effective amount of a cancer therapeutic in a physiologically acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and the clinical symptoms of cancer progression or metastasis. Generally, amounts can be in the range of those used for other agents used in the treatment of cancer progression or metastasis, although in certain instances lower amounts will be needed because of the increased specificity of the compound. A compound can be administered at a dosage that controls the clinical or physiological symptoms of cancer progression or metastasis as determined by a diagnostic method known to one skilled in the art, or using any that assay that measures the transcriptional activation of a gene associated with cancer progression or metastasis.

Formulation of Pharmaceutical Compositions

The administration of a pharmaceutical composition of the invention for the treatment of a cancer which is resistant to antiprogestin therapy may be by any suitable means that results in a concentration of the demethylating agent and antiprogestin that, when combined with other components, are effective in ameliorating, reducing, eradicating, or stabilizing resistant cancer. Preferably, the mode of delivery or administration tends to result in the entry of the pharmaceutical composition in the cancerous cells.

Methods of administering such compositions are known in the art. The disclosure provides for the therapeutic administration of the compositions of the invention by any means known in the art. The compositions may be contained in any appropriate amount in any suitable carrier substance, and is generally present in an amount of 1-95% by weight of the total weight of the composition. The compositions may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). Suitable formulations include forms for oral administration, depot formulations, formulations for delivery by a patch, and semi-solid dosage forms to be topically or transdermally delivered.

Pharmaceutical compositions according to the disclosure may be formulated to release the active agents (e.g., the demethylation agent and/or the antiprogestin) substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (saw-tooth kinetic pattern); (iv) formulations that localize action by, e.g., spatial placement of a controlled release composition adjacent to or in a breast cancer; (v) formulations that allow for convenient dosing, such that doses are administered, for example, once every one or two weeks; and (vi) formulations that target tumor cells by using carriers or chemical derivatives to deliver the therapeutic agent to a particular cell type whose function is perturbed in cancer. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The delivery vehicles contemplated by the invention that may carry the therapeutic antiprogestins and/or demethylation agents to the cells of the cancerous subject may also be targeted to particular cells by employment of any suitable targeting means. Such means may include incorporating a delivery moiety or targeting moiety into the delivery vehicle to enable the targeted delivery of the compositions of the invention to specified cells or tissues or area of the body, e.g., breast tumor.

As used herein, the term "delivery moiety" or "targeting moiety" is a moiety that is capable of enhancing the ability of an associated or attached delivery vehicle of the invention to associate with, bind, or enter a cell, cell of a tissue or subject, cell type, tissue or location within a subject, either in vitro or in vivo. In certain embodiments, delivery moieties are polypeptides, carbohydrates or lipids. Optionally, delivery moieties are antibodies, antibody fragments or nanobodies. Exemplary delivery moieties include tumor targeting moieties, such as somatostatin (sst2), bombesin/GRP, luteinizing hormone-releasing hormone (LHRH), neuropeptide Y (NPY/Y1), neurotensin (NT1), vasoactive intestinal polypeptide (VIP/VPAC1) and cholecystokinin (CCK/CCK2). In certain embodiments, a delivery moiety is non-covalently associated with a compound of the invention. In other embodiments, a delivery moiety is attached to a delivery vehicle of the invention, and is optionally covalently attached. In further embodiments, a delivery moiety is attached to a delivery vehicle of the invention, and is optionally covalently attached. In additional embodiments, a delivery moiety is attached directly to a "cargo" of the invention (e.g., an antiprogestin of the invention), optionally covalently. In certain instances, the formulations of the invention comprise a ligand, such as a targeting ligand that may interact with a specific receptor on a target cell type. Exemplary ligands include lipids, amphipathic lipids, carrier compounds, bioaffinity compounds, biomaterials, biopolymers, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In certain other embodiments, the delivery vehicles carrying the antiprogestins and/or demethylation agents to cancerous cells may include lipid-based carrier systems suitable for use in the present invention, including lipoplexes (see, e.g., U.S. Patent Publication No. 20030203865; and Zhang et al., *J. Control Release*, 100:165-180 (2004)), pH-sensitive lipoplexes (see, e.g., U.S. Patent Publication No. 2002/0192275), reversibly masked lipoplexes (see, e.g., U.S. Patent Publication Nos. 2003/0180950), cationic lipid-based compositions (see, e.g., U.S. Pat. No. 6,756,054; and U.S. Patent Publication No. 2005/0234232), cationic liposomes (see, e.g., U.S. Patent Publication Nos. 2003/0229040, 2002/0160038, and 2002/0012998; U.S. Pat. No. 5,908,635; and PCT Publication No. WO 01/72283), anionic liposomes (see, e.g., U.S. Patent Publication No. 2003/0026831), pH-sensitive liposomes (see, e.g., U.S. Patent Publication No. 2002/0192274; and AU 2003/210303), antibody-coated liposomes (see, e.g., U.S. Patent Publication No. 2003/0108597; and PCT Publication No. WO 00/50008), cell-type specific liposomes (see, e.g., U.S. Patent Publication No. 2003/0198664), liposomes containing nucleic acid and peptides (see, e.g., U.S. Pat. No. 6,207,456), liposomes containing lipids derivatized with releasable hydrophilic polymers (see, e.g., U.S. Patent Publication No. 2003/0031704), lipid-entrapped nucleic acid (see, e.g., PCT Publication Nos. WO 03/057190 and WO 03/059322), lipid-encapsulated nucleic acid (see, e.g., U.S. Patent Publication No. 2003/0129221; and U.S. Pat. No. 5,756,122), other liposomal compositions (see, e.g., U.S. Patent Publication Nos. 2003/0035829 and 2003/0072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 2005/0037086), the disclosures of which are each incorporated in their entireties by reference.

The delivery vehicles used to administer the compositions of the invention also may include polymer-based carrier systems which may include, but are not limited to, cationic polymer-nucleic acid complexes (i.e., polyplexes). To form a polyplex, cargo (e.g., a tswRNA of the invention) is typically complexed with a cationic polymer having a linear, branched, star, or dendritic polymeric structure that condenses the cargo into positively charged particles capable of interacting with anionic proteoglycans at the cell surface and entering cells by endocytosis. In some embodiments, the polyplex comprises nucleic acid (e.g., tswRNAs) complexed with a cationic polymer such as polyethylenimine (PEI) (see, e.g., U.S. Pat. No. 6,013,240; commercially available from Qbiogene, Inc. (Carlsbad, Calif.) as In vivo jetPEI®, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymernucleic acid complexes as described in U.S. Patent Publication Nos. 2006/0211643, 2005/0222064, 2003/0125281, and 2003/0185890, and PCT Publication No. WO 03/066069; biodegradable poly(β-amino ester) polymer-nucleic acid complexes as described in U.S. Patent Publication No. 2004/0071654; microparticles containing polymeric matrices as described in U.S. Patent Publication No. 2004/0142475; other microparticle compositions as described in U.S. Patent Publication No. 2003/0157030; condensed nucleic acid complexes as described in U.S. Patent Publication No. 2005/0123600; and nanocapsule and microcapsule compositions as described in AU 2002358514 and PCT Publication No. WO 02/096551. These disclosures are incorporated herein by reference.

In certain instances, the compositions of the invention may be complexed with cyclodextrin or a polymer thereof. Non-limiting examples of cyclodextrin-based carrier systems include the cyclodextrin-modified polymer-nucleic acid complexes described in U.S. Patent Publication No. 2004/0087024; the linear cyclodextrin copolymer-nucleic acid complexes described in U.S. Pat. Nos. 6,509,323, 6,884,789, and 7,091,192; and the cyclodextrin polymer complexing agent-nucleic acid complexes described in U.S. Pat. No. 7,018,609. In certain other instances, the cargo (e.g., a nucleic acid such as a DsiRNA for inhibiting gene expression, e.g., of PRB) may be complexed with a peptide or polypeptide. An example of a protein-based carrier system includes, but is not limited to, the cationic oligopeptide-nucleic acid complex described in PCT Publication No. WO95/21931. These disclosures are incorporated herein by reference.

Pharmaceutical Compositions

In certain embodiments, the present invention provides for a pharmaceutical composition comprising a composition of the present invention. Such compositions can be suitably formulated and introduced into the environment of the cell by any means that allows for a sufficient portion of the inventive compositions to enter the cell to deliver a cargo/payload. Many formulations are known in the art and can be used so long as the inventive formulation gains entry to the target cells so that it can act. See, e.g., U.S. published patent application Nos. 2004/0203145 A1 and 2005/0054598 A1. For example, the inventive formulation of the instant invention can be further formulated in buffer solutions such as phosphate buffered saline solutions and capsids. Cationic lipids, such as lipofectin (U.S. Pat. No. 5,705,188), cationic glycerol derivatives, and polycationic molecules, such as polylysine (published PCT International Application WO 97/30731), can be used within the formulations of the instant invention. Optionally, Oligofectamine, Lipofectamine (Life Technologies), NC388 (Ribozyme Pharmaceuticals, Inc., Boulder, Colo.), or FuGene 6 (Roche) may be employed, all of which can be used according to the manufacturer's instructions.

Such compositions can include the lipidic formulation and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular cargo delivery has also been discussed in Straubringer et al., *Methods Enzymol.*, 101: 512; Mannino et al, *Biotechniques*, 6:10 682; Nicolau et a/., Crit. Rev. Ther. Drug Carrier Syst., 6:239 (1989); and Behr, *Ace. Chem. Res.,* 26: 274. Still other methods of administering lipid-based therapeutics are described in, for example, U.S. Pat. Nos. 3,993,754; 4,145,410; 4,235,871; 4,224,179; 4,522,803; and 4,588,578. The lipid-cargo formulation particles can be administered by direct injection at the site of disease or by injection at a site distal from the site of disease (see, e.g., Culver, HUMAN GENE THERAPY, MaryAnn Liebert, Inc., Publishers, New York. pp. 70-71). The formulations of the present invention, either alone or in combination with other suitable components, can be made into aerosols (i.e., they can be "nebulized") to be administered via inhalation (e.g., intranasally or intratracheally; see, Brigham et al., *Am. J. Sci.,* 298: 278). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidylglycerol compounds (U.S. Pat. No. 5,725,871) is also well-known in the pharmaceutical arts. Similarly, transmucosal drug delivery in the form of a polytetrafluoroetheylene support matrix is described in U.S. Pat. No. 5,780,045.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, formulations can be administered, for example, by intravenous infusion, orally, topically, intraperitoneally, intravesically, or intrathecally.

Pharmaceutical compositions, suitable for injectable use, include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, optional methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the formulations are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active formulations are formulated into ointments, salves, gels, or creams as generally known in the art.

The formulations can also be prepared in the form of suppositories (e.g., with conventional suppository bases such as cocoa butter and other glycerides) or retention enemas for rectal delivery.

The formulations can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

In certain embodiments, the formulations can also be administered by any method suitable for administration of nucleic acid agents, such as a DNA vaccine. These methods include gene guns, bio injectors, and skin patches as well as needle-free methods such as micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In certain aspects, the formulations are prepared with carriers that will protect the formulations against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Formulations suitable for oral administration can consist of, e.g.: (a) liquid solutions, such as an effective amount of the packaged cargo (e.g., nucleic acid) suspended in diluents such as water, saline, or PEG 400; (b) capsules, sachets, or tablets, each containing a predetermined amount of the cargo, as liquids, solids, granules, or gelatin; (c) suspensions in an appropriate liquid; and (d) suitable emulsions. Tablet forms can include one or more of lactose, sucrose, manitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the cargo in a flavor, e.g., sucrose, as well as pastilles comprising the cargo in an inert base, such as gelatin and glycerin or sucrose and acacia emulsions, gels, and the like containing, in addition to the cargo, carriers known in the art.

The methods of the present invention may be practiced in a variety of hosts. Exemplary hosts include mammalian species, such as primates (e.g., humans and chimpanzees as well as other nonhuman primates), canines, felines, equines, bovines, ovines, caprines, rodents (e.g., rats and mice), lagomorphs, and swine.

Toxicity and therapeutic efficacy of such formulations can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Formulations which exhibit high therapeutic indices can be preferred. While formulations that exhibit toxic side effects may be used, care should be taken to design a delivery system that targets such formulations to the site of affected tissue in order to minimize potential damage to uninfected cells and, thereby, reduce side effects.

The data obtained from the cell culture assays and animal studies can be used in formulating a range of dosage for use in humans. The dosage of such formulations optionally lies within a range of circulating concentrations that include the ED50 with little or no toxicity. The dosage may vary within this range depending upon the dosage form employed and the route of administration utilized. For any formulation used in a method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of formulation (i.e., an effective dosage) depends on the formulation selected. For instance, if a antiprogestin formulation is selected, single dose amounts (of either the formulation as a whole or of a cargo component of such formulation) in the range of approximately 1 pg to 1000 mg may be administered; in some embodiments, 10, 30, 100, or 1000 pg, or 10, 30, 100, or 1000 ng, or 10, 30, 100, or 1000 μg, or 10, 30, 100, or 1000 mg may be administered. In some embodiments, 1-5 g of the formulations can be administered. The formulations can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, nucleic acid or antibody can include a single treatment or, optionally, can include a series of treatments.

It can be appreciated that the method of introducing formulations into the environment of the cell will depend on the type of cell and the makeup of its environment. For example, when the cells are found within a liquid, one optional formulation is with a lipid formulation such as in lipofectamine and the formulations can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering peptides, proteins and nucleic acids (e.g., oligonucleotides) are known and can be used. For suitable methods of introducing dsRNA (e.g., 15 tswRNA agents), see U.S. published patent application No. 2004/0203145 A1.

Suitable amounts of a formulation must be introduced and these amounts can be empirically determined using standard methods. Typically, effective concentrations of individual formulations, or of individual cargoes of a formulation, in the environment of a cell will be about 50 nanomolar or less, 10 nanomolar or less, or compositions in which concentrations of about 1 nanomolar or less can be used. In another embodiment, methods utilizing a concentration of about 200 picomolar or less, and even a concentration of about 50 picomolar or less, about 20 picomolar or less, about 10 picomolar or less, or about 5 picomolar or less can be used in many circumstances.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

Inhibitory Nucleic Acids

In embodiments involving the inhibition of gene expression, e.g., where the gene encoding PRB is inhibited in order to reduce the molar amount of PRB relative to PRA. Such inhibitory nucleic acids include single and double stranded nucleic acid molecules (e.g., DNA, 5 RNA, and analogs thereof) that bind a nucleic acid molecule that encodes target RNA (e.g., antisense oligonucleotide molecules, siRNA, shRNA) as well as nucleic acid molecules that bind directly to a target polypeptide to modulate its biological activity (e.g., aptamers). In view of these embodiments, the invention contemplates the delivery and/or administration of naked inhibitory nucleic acid molecules of the invention (e.g., inhibitory against PRB of the invention), or analogs thereof, which are capable of entering mammalian cells and inhibiting expression of a gene of interest, and in particular, where the mammalian cell is infected with a target RNA. Nonetheless, it may be desirable to utilize a formulation that aids in the delivery of the inhibitory RNAs of the invention, or any nucleic acids of the invention, to cells (see, e.g., U.S. Pat. Nos. 5,656,611, 5,753,613, 5,785,992, 6,120,798, 6,221,959, 6,346,613, and 6,353,055, each of which is hereby incorporated by reference).

In embodiments that utilize lipid-based delivery vehicles to administer any inhibitory RNAs of the invention, the cargo-lipid formulation particles can be detected in the subject at about 8, 12, 24, 48, 60, 72, or 96 hours, or 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles; detection of the modified cargo (e.g., nucleic acid); where the cargo is a nucleic acid, detection of a nucleic acid that silences expression of a target sequence; detection of the target and/or target sequence of interest (i.e., by detecting expression or reduced expression of the target and/or sequence of interest), or a combination thereof. A cargo-lipid formulation comprising a peptide-modified lipid of the invention, when compared to a control formulation, results in at least 5%, 10%, 20%, 30%, 40%, 50%, 60%, 70%, 80%, 90%, 95%, or even 100% increase in the detection of cargo-lipid formulation particles, as measured by a detection method, e.g., fluorescent tag or PCR.

Cargo-lipid formulation particles can be detected using any methods known in the art. For example, a label can be coupled directly or indirectly to a component of the carrier system using methods well-known in the art. A wide variety of labels can be used, with the choice of label depending on sensitivity required, ease of conjugation with the carrier system component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as 3H, 125I, 35S, 'C, 32P, 33P, etc.; enzymes such as horseradish peroxidase, alkaline phosphatase, etc.; spectral colorimetric labels such as colloidal gold or colored glass or plastic beads such as polystyrene, polypropylene, latex, etc. The label can be detected using any means known in the art.

Cargoes can be detected and quantified herein by any of a number of means well-known to those of skill in the art. The detection of nucleic acids proceeds by well-known methods such as Southern analysis, Northern analysis, gel electrophoresis, PCR, radio labeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyper diffusion chromatography may also be employed for a cargo of a formulation of the invention.

For nucleic acid cargoes, the selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

Sensitivity of a hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook et al, In Molecular Cloning: A Laboratory Manual, Cold Spring Harbor Laboratory Press (2000); and Ausubel et al, SHORT PROTOCOLS Ind. MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), C&EN 36; The Journal Of NIH Research, 3:81 (1991); Kwoh et al., Proc. Natl. Acad. ScL USA, 86:1173 (1989); Guatelli et al., Proc. Natl. Acad. Sci. USA, 87: 1874 (1990); Lomeli et al., J. 5 Clin. Chem., 35: 1826 (1989); Landegren et al, Science, 241:1077 (1988); Van Brunt, Biotechnology, 8:291 (1990); Wu and Wallace, Gene, 4:560 (1989); Barringer et al, Gene, 89: 117 (1990); and Sooknanan and Malek, Biotechnology, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Nucleic acids, e.g., those in Table 1, for use as probes, e.g., in vitro amplification methods, for use as gene probes, or as inhibitor components are typically synthesized chemically according to the solid phase phosphoramidite triester method described by Beaucage et al, Tetrahedron Letts., 22: 1859-1862 (1981), e.g., using an automated synthesizer, as described in Needham VanDevanter et al, Nucleic Acids Res., 12:6159 (1984). Purification of polynucleotides, where necessary, is typically performed by either native acrylamide gel electrophoresis or by anion exchange HPLC as described in Pearson et al, J. Chrom., 255: 137-149 (1983). The sequence of the synthetic polynucleotides can be verified using the chemical degradation method of Maxam and Gilbert (1980) in Grossman and Moldave (eds.) Academic Press, New York, Methods in Enzymology, 65:499.

An alternative means for determining the level of transcription of a nucleic acid/gene (e.g., target gene) is in situ hybridization. In situ hybridization assays are well-known and are generally described in Angerer et al., *Methods Enzymol,* 152: 649. In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are optionally labeled with radioisotopes or fluorescent reporters.

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used; such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Therapeutic Methods

The present disclosure provides methods of treating cancers, particularly breast cancers, which are responsive to antiprogestins or which can be induced to be responsive to antiprogestins, e.g., by administering a demethylating agent. The methods comprise administering a therapeutically effective amount of a pharmaceutical composition comprising an antiprogestin and optionally a demethylating agent.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the disclosure, which include prophylactic treatment, in general comprise administration of a therapeutically effective amount of the agent herein, such as a compound of the formulae herein to a subject (e.g., animal, human) in need thereof, including a mammal, particularly a human. Such treatment will be suitably administered to subjects, particularly humans, suffering from, having, susceptible to, or at risk for a cancer progression or metastasis or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agent herein may be also used in the treatment of any other disorders in which transcriptional activity may be implicated.

In one embodiment, the disclosure provides a method of monitoring treatment progress. The method includes the step of determining a level of diagnostic marker (Marker) (e.g., a marker indicative of cancer progression or regression) or diagnostic measurement (e.g., screen, assay) in a subject suffering from or susceptible to a disorder or symptoms thereof associated with cancer, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status.

Kits

The disclosure provides kits for the treatment of cancers, especially breast cancers, which are responsive to antiprogestins or which may be induced to be responsive to antiprogestins by co-administering a demethylating agent. In one embodiment, the kit includes a therapeutic or prophylactic composition containing an effective amount of an agent of the invention (e.g., antiprogestin) in unit dosage form. In some embodiments, the kit further comprises an effective amount of a demethylating agent. Further, the kit of the invention may comprise a sterile container which contains a therapeutic or prophylactic compounds; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the disclosure is provided together with instructions for administering it to a subject of the invention. The instructions will generally include information about the use of the composition for the treatment of cancer, or breast cancer. The instructions may be printed directly on the container (when present), or as a label applied to the container, or as a separate sheet, pamphlet, card, or folder supplied in or with the container.

Combination Therapies for the Treatment of Cancers

Compositions and methods of the disclosure may be used in combination with any conventional therapy known in the art for treating cancer, and especially breast cancer. In one embodiment, a composition of the disclosure (e.g., a composition comprising an antiprogestin) may be used in combination with any other hormone therapy, e.g., antiestrogen agent or any other known anti-cancer agent. Combination therapies may include the administration or co-administration of standard antiestrogen therapies (also referred to as selective estrogen receptor modulators or SERMs), including administering of antiestrogens such as tamoxifen (NOLVADEX), toremifene (FARESTON), raloxifene (EVISTA), or fulvestrant. Antiestrogen anticancer treatments are well-known in the art, such as, for example, in Clarke et al., Oncogene (2003), Vol. 22, pp. 7316-7339, which is incorporated by reference. Without being bound by theory, SERMs block the effects of estrogen in the breast tissue. SERMs work by sitting in the estrogen receptors in breast cells, thereby blocking the binding of estrogen itself to the receptor. Without estrogen bound to the cell, the cell does not receive estrogen's signals to grow and multiply, thereby reducing the growth of a cancerous cell. This type of therapy may be administered in combination with any of the therapies described herein.

Recombinant Polypeptide Expression

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow. The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The present invention is described by reference to the following Examples, which are offered by way of illustration and are not intended to limit the invention in any manner. Standard techniques well known in the art or the techniques specifically described below were utilized.

Example 1: Antiprogestins as Possible Therapeutic Agents for Breast Cancer Patients Showing a High Expression of Progesterone Receptor Isoform A Near 75% of breast cancer patients express progesterone (PR) and estrogen (ER) receptors and are potential candidates to receive an endocrine therapy. Most of the endocrine treatments available have been designed to target ER and there is not much information about PR as a therapeutic target for breast cancer treatment. Progestins appear to be associated with the induction and maintenance of the neoplastic phenotype in the mammary gland. Moreover, different antiprogestins including ZK98299, ZK230211, and RU-486 proved to exert excellent therapeutic effects in murine mammary carcinomas which express an increased PR-isoform A/PR-isoform B ratio (PR-A/PR-B).

It has been demonstrated that metastatic murine mammary carcinomas expressing an increased PR-A/PR-B ratio, as determined by Western Blot (WB), are inhibited by antiprogestins. In contrast, the constitutive resistant tumors, or those which have acquired antiprogestin resistance by selective pressure, show a higher ratio of PR-B/PR-A. However, by immunohistochemistry (IHC), all were classified as PR positive. This Example hypothesizes that the levels of PR isoforms in breast cancer could define subgroups of patients that may differentially respond to antiprogestin therapy. The Example postulates that patients with high PR-A levels should be those that respond to an antiprogestin treatment.

Thus the main goal of this Example was to identify the breast cancer patients that may benefit from an antiprogestin therapy, and included the specific aims of: (a) to perform primary cultures from breast cancer samples obtained at surgery, and to evaluate in each case the ability of RU-486 to inhibit cell proliferation; (b) to determine the ratio of PR-A/PR-B of each tumor sample and (c) to correlate the inhibitory effect observed in vitro, with the expression of PR-A and PR-B. This will allow the identification of the group of patients who may benefit from an antiprogestin therapy.

Materials and Methods.

Tumor Samples.

The samples were obtained at surgery from patients diagnosed with breast cancer at the Magdalena V. de Martinez Hospital from General Pacheco and at the Rivadavia Hospital of Buenos Aires after signing the informed consent (n=70; median age 55 year). Protocols were approved by the Institutional Ethical Review Board. Whenever possible, one piece of the sample was kept in dry ice immediately after surgery and another piece was kept in culture medium and transported to IBYME.

Primary Cultures.

Tumor samples were processed by mechanical and enzymatic degradation and epithelial cells were purified by differential sedimentation techniques (7). The epithelial cells were cultured with DMEM/F12 medium plus 10% fetal calf serum (FCS). Once the cultures were overcrowded, they were subcultured and equal numbers of cells were seeded in 24 well plates. After attachment, cells were incubated with growth medium in the presence of vehicle or 10-8 M RU-486 (Sigma, St. Louis, Mo.). OH-Tamoxifen was also used as a control. After one week of treatment, the cells were trypsinized and the total number of cells in each well was counted or alternatively, they were fixed to evaluate the Ki67 (proliferation marker) expression by IHC. In several cases in which there were carcinoma associated fibroblasts intermingled with the epithelial cells, a double staining of Ki67 and cytokeratin (CK) was performed to consider the proliferating cells among the total number of epithelial cells (CK+). An inhibitory index was calculated for each tumor.

Western Blot.

Fifty micrograms of extracted protein was run on 8% SDS polyacrylamide gels and nitrocellulose membranes were probed with PgR 1294 (Dako, Carpinteria Calif.), Ab7 (Neomarkers, Fremont, Calif.) or C-19 (Santa Cruz Biotec, Santa Cruz, Calif.). Band intensities were measured densitometrically using AlphaEaseFC software (Alpha Innotech, San Leandro Calif.).

Results

Figure 2B:
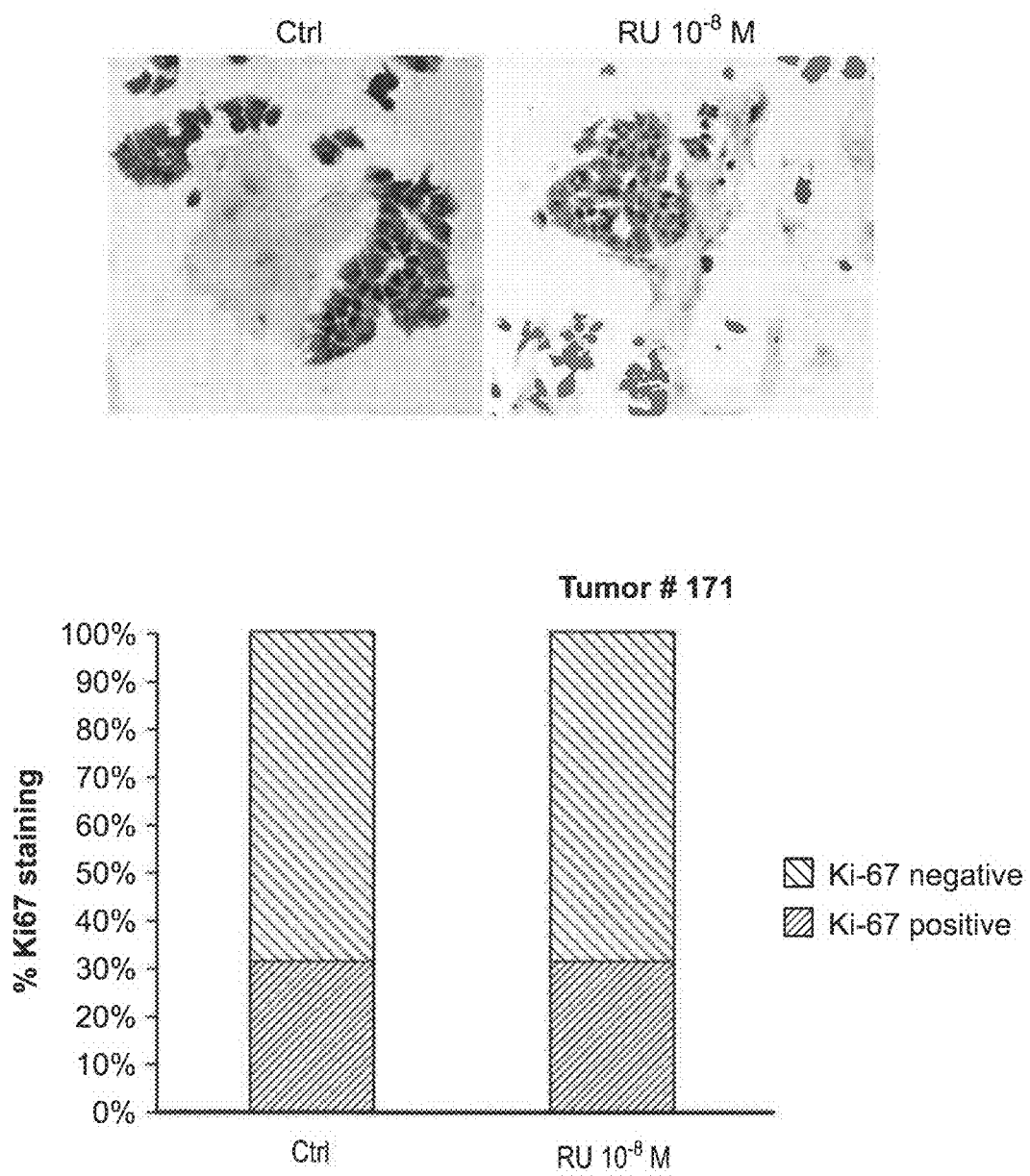

Seventy tumors were processed for primary cultures and WB. Only 11.4% of the tumor samples succeeded in tissue culture and were subcultured to evaluate cell proliferation. In 3 out of 8 cases, treatment with RU-486 or with Tamoxifen induced a significant decrease in the number of cells as compared to the controls (p<0.05). In 2 other cases the decrease did not reach statistical significance. In these 5 patients PR-A expression was higher than PR-B (WB). The three PR negative tumors showed no in vitro responsiveness. Two representative cases are shown in FIGS. 2A and 2B. Case #137 represents an ER+ and PR+ (IHC) invasive ductal carcinoma which shows high PR-A/PR-B (WB) and a decrease in cell proliferation in RU-486-treated cells (p<005; FIG. 2A). In contrast, case #171 represents a PR− (IHC; WB) invasive ductal carcinoma showing similar levels of Ki67+ cells in RU-486-treated or untreated cells (FIG. 2B). The levels of PR-B (115 kDa) and PR-A (94 kDa) expression observed in WB can be appreciated in FIG. 3A. Similar results were obtained using 3 different antibodies (not shown). The PgR 1294 antibody recognizes both isoforms in IHC studies, and as shown in FIG. 4, an intense specific nuclear staining was observed in PR+ samples.

Conclusions

The effect of antiprogestins in vitro could be evaluated in 11.4% of the tumors studied. An inhibitory effect of RU-486 on cell proliferation was observed in samples which showed high levels of PR-A expression. The results suggest that antiprogestins might be an alternative therapy to treat breast carcinomas expressing high levels of PR-A.

REFERENCES FOR EXAMPLE 1

1. Beral V 2003 Breast cancer and hormone-replacement therapy in the Million Women Study. *Lancet* 362 419-427.
2. Lanari C, Molinolo A A & Pasqualini C D 1986 Induction of mammary adenocarcinomas by medroxyprogesterone acetate in BALB/c female mice. *Cancer Lett.* 33 215-223.
3. Lydon et al., 1999, Cancer Res. 1:59(17)4276-84.
4. Lanari C, Lamb C, Fabris V, Helguero L, Soldati R, Bottino M, Giulianelli S, Cerliani J, Wargon V & Molinolo A 2009 The MPA mouse breast cancer model: evidence for a role of progesterone receptors in breast cancer. *Endocr. Relat. Cancer.*
5. Helguero et al., 2003, Breast Cancer Res Treat 79(3):379-90.
6. Wargon et al., 2009, Breast Cancer Res Treat: 116(3): 449-60.
7. Pandis et al., 1992, Genes Chromosomes Cancer, 5(1): 14-20.

Example 2: Hypermethylation of the Progesterone Receptor a in Constitutive Antiprogestin Resistant Mouse Mammary Carcinomas Introduction Two-thirds of breast cancers express estrogen receptor (ER) and progesterone receptor (PR) at the time of diagnosis [1]. Most tumors initially respond to endocrine therapy, but many will eventually develop resistance (acquired hormone resistance). However, some tumors fail to respond to endocrine treatment from the beginning (constitutive resistance) despite expressing hormone receptors [2].

Progesterone receptor exists as two isoforms, PRA and PRB, which are transcribed from a single gene under the control of distinct promoters [3, 4]. Both isoforms bind progestins and directly activate the expression of genes that contain progesterone response elements in their promoters.

Alternatively, the PRs can cooperate with other transcription factors to induce gene transcription. However, there is increasing evidence that the two isoforms have different functions in vivo [5-8].

The inventors previously developed a model of breast cancer in which the administration of medroxyprogesterone acetate (MPA) to female BALB/c mice induces mammary ductal carcinomas [9, 10]. The main features of this tumor model have recently been reviewed [11]. Although these tumors were all originally MPA dependent, some MPA-independent metastatic tumors capable of growing in untreated mice, which retained high levels of ER and PR expression, were obtained by syngeneic transplantation [11]. While most of the MPA independent tumors regressed in response to antiprogestins (antiprogestin responsive), some of them did not and were designated as constitutive antiprogestin-resistant tumors. From the MPA independent tumors that regressed with antiprogestins, by selective pressure, we were also able to generate variants with acquired antiprogestin resistance. The inventors recently reported that PRA is down regulated in both, constitutive and acquired antiprogestin-resistant tumors [12, 13]. Interestingly, the tumors with acquired resistance reverted to the antiprogestin-responsive phenotype following estrogen or tamoxifen treatment or by successive transplantations in untreated mice. Furthermore, in all cases, the reacquisition of antiprogestin responsiveness could be correlated with an increase in PRA expression [13].

It has been shown that one mechanism for the loss of gene expression in oncogenesis is the aberrant methylation of CpG islands in the 5' regulatory region and first exon of target genes [14]. CpG islands are regions of DNA with several CpG sites, in which a cytosine residue located 5' of guanine residue is methylated. At least, three types of DNA methyltransferases (Dnmt) exist in mammals: Dnmt1 is a maintenance methylase, while Dnmt3a and Dnmt3b are de novo methylases [15, 16]. Compared to normal cells, cancer cells show a drastic change in DNA methylation, generally exhibiting global DNA hypomethylation as well as region-specific hypermethylation [17]. A correlation between the over expression of Dnmts and hypermethylation in breast cancer cell lines has been demonstrated [18]. 5-aza-2'-deoxycytidine (5azadC) is a well-known demethylating agent that is activated in vivo and readily incorporated into DNA during replication. As a result of the methyltransferase reaction, the Dnmt becomes covalently linked to DNA, rendering it unable to maintain its methylase activity [15]. Treatment of ERx-negative cells with 5azadC leads to reactivation of functional ERx expression [15, 16, and 19].

Methylation of the CpG islands located in the ER and PR genes has been reported in a significant fraction of ER- and PR-negative primary breast cancers and breast cancer cell lines [20-26]. However, no studies in which the methylation status of steroid receptor genes was evaluated in tumors with acquired resistance have been done. The main goal of this study was 15 to evaluate whether DNA methylation could explain PRA silencing in tumors with acquired or constitutive antiprogestin resistance in our experimental model. This Example demonstrates that PRA is silenced by DNA methylation in constitutive antiprogestin-resistant carcinomas and, 5azadC treatment restores PRA expression and antiprogestin RU-486 responsiveness in vitro and in vivo. This suggests that different epigenetic mechanisms are involved in constitutive antiprogestin resistance and in acquired antiprogestin resistance. In addition, these studies reinforce a pivotal role for PRA mediating antiprogestin's inhibitory effect, highlighting the differential roles of PRA and PRB.

Materials and Methods

Animals.

Two-month-old virgin female BALB/c mice (IBYME Animal Facility) were used. Animal care and manipulation protocols were in agreement with institutional guidelines and the Guide for the Care and Use of Laboratory Animals [27].

Tumors.

Mammary carcinomas from the MPA breast cancer model were used: C4-HI, C4-HIR, and C4-2-HI are all MPA-independent variants from the C4 family; 59-2-HI, 59-2-HIR, and 59-HI are variants from the 59 family of tumors; C4-HI and 59-2-HI are antiprogestin responsive tumors [13, 28]; C4-HIR and 59-2-HIR are their respective antiprogestin-resistant variants [13]; and C4-2-HI and 59-HI are constitutive-resistant variants [12]. Tumors were named before learning their antiprogestin responsiveness. All these tumor variants express ER and PR evaluated by binding, western blotting, and immunohistochemistry assays [11]. However, low levels of PRA were detected in antiprogestin-resistant tumors [12, 13]. Tumors were transplanted by subcutaneous (s.c.) injection into the inguinal flank of BALB/c mice.

Reagents.

The 5azadC, MPA, and RU-486 (mifepristone) were purchased from Sigma-Aldrich (St. Louis, Mich.), and ZK 230211 was a kind gift from Bayer Schering Pharma AG, Berlin.

Methylation-Specific PCR (MSP).

Genomic DNA was extracted from tumors, and 1 μg DNA was subjected to sodium bisulfite conversion as described by Frommer et al. [29] with brief modifications. Sodium bisulfite-modified DNA (150 ng) was used as the template in each PCR reaction. The PCR mixture contained PCR buffer, 1.5 mM MgCl2, 200 μM dNTPs, 0.2 μM of each primer, and 1 unit Platinum Taq Polymerase (Invitrogen, Carlsbad, Calif.). In order to amplify the unmethylated (UM) and methylated (M) CpG sites, the primers listed in Table 1 (see below) were used. These primers were designed using Methyl Primer Express Software 1.0 from Applied Biosystems (Foster City, Calif.) and the sequence of the promoter and the first exon of PR (http://www.ensembl.org/Mus_musculus/index.html) [30]. The PCR conditions and the annealing temperatures are indicated in Table 1. In order to obtain DNA from normal lymphocytes to be used in control experiments, axillary and inguinal lymph nodes from 6 BALB/c mice were excised and processed as the tumor samples. The lymphocyte DNA was treated with sodium bisulfite (UM control) or was hypermethylated with SssI methyltransferase (New England Biolabs, Beverly, Mass.), and subsequently treated with sodium bisulfite (M control). PCR products were visualized in a 2% agarose gel.

Cloning and Sequencing of MSP Products.

The PCR products (UM and M) obtained using the PR4 primer pair from three responsive (C4-HI, 59-2-HI), three constitutive (C4-2-HI, 25 59-HI), and three acquired antiprogestin-resistant (C4-HIR, 59-2-HIR) tumors from each tumor family were cloned into pCR2.1-TOPO (Invitrogen). This PR4 product was chosen because it had the highest levels of CpG islands. The plasmids were transformed into chemically competent E. coli TOP10 (Invitrogen). The bacteria were plated on LB agar plates containing 100 μg/ml of ampicillin and 40 μl/plate of 40 mg/ml X-gal (Promega, Madison, Wis.). Ten white 30 colonies from each group were analyzed by colony PCR using PR4 primer pair to confirm their positivity. The fragments were sequenced by Macrogen Inc. (Korea) using the 3730XL DNA Sequencer. Sequences were finally analyzed using EMBLE-EBI software (http:// www.ebi.ac.uk). The percentage of methylation was calculated for each of the three samples from each tumor, and the mean±SEM was calculated for each tumor.

Primary Cultures and Co-Cultures

Culture Media.

DMEM/F12 (Dulbecco's modified Eagle's medium: Ham's F12, 1:1, without phenol red, Sigma Chem. Co. St Louis Mo., USA); 100 U/ml penicillin; and 100 µg/ml streptomycin with 10% fetal calf serum (FCS; Life Technologies Inc., Gaithersburg, Md., USA). Steroid-stripped FCS was prepared as described previously [31], and it was used in proliferation assays to avoid the interference with endogenous hormones.

Primary Cultures.

Epithelial cells and carcinoma-associated fibroblasts were separated by differential sedimentation [32] and plated with 10% FCS. Carcinoma-associated fibroblasts were allowed to attach for 0.5 h and the epithelial cells for 24-48 h. The medium was replaced by fresh medium with 10% FCS; thereafter, it was changed every 2-3 days.

Co-Cultures.

Trypsinized cells were resuspended and equal amounts of epithelial cells and carcinoma-associated fibroblasts were seeded with 10% FCS that was replaced after attachment by 1% steroid-stripped FCS. As previously demonstrated in these experimental conditions, both cell types are in quiescence, and they only grow in co-cultures [32]. The same amount of epithelial cells or carcinoma-associated fibroblasts or double the amount of purified cells was used for comparison.

Cell Proliferation.

(3H)-thymidine-uptake was used as an indirect method to evaluate cell proliferation [32]. In brief, cells were seeded into 96-well microplates. After attachment (24 h), the cells were incubated for 24 h with 1% steroid-stripped FCS and then for 48 h with the experimental solutions to be tested in 1% chFCS. Fifty percent of the medium was replaced with fresh medium every 24 h. The cells were incubated with 0.4 µCi of 3H-thymidine (specific activity: 20 Ci/mmol) for 24 h, trypsinized, and harvested in a cell harvester. In experiments in which 5azadC was used, the experiments were carried out using proliferating cells (presence of 10% FCS) to guarantee the effect of the demethylating agent. Three different experiments were made using octuplicates, and the means and standard deviations of one representative experiment of the other three are shown. The results are expressed as the proliferation index (cpm 30 experimental group/cpm control; mean±SEM) [33].

Treatment of Epithelial Cells with 5azadC In Vitro.

C4-2-HI and 59-HI epithelial cells from primary cell cultures were allowed to attach for 24 h. The medium was replaced with fresh medium with 10% FCS, and 5azadC was added for 96 h. The medium was refreshed daily. Cells were processed for western blot or immunofluorescence to evaluate PR expression.

In Vivo Treatment with RU-486 and 5azadC.

C4-2-HI, 59-HI, and C4-HIR tumors were transplanted s.c nearby the mammary gland 4th in syngenic mice, and measured every 2 days (length and width). Treatments were initiated when the tumors were palpable. The antiprogestin RU-486 (mifepristone) was inoculated s.c at a dose of 12 mg/kg/day. The mice were inoculated intraperitoneally (i.p.) with 0.75 mg/kg 5azadC (for C4-2-HI and C4-HIR tumors) or 1 mg/kg 5azadC (for 59-HI tumors) every other day. All the experiments were repeated twice using five mice per group. The animals were euthanized after 13 days of treatment, and tumor samples were removed and frozen at −80° C. or fixed in 10% formaldehyde.

Western Blots.

Cytosolic or nuclear extracts were processed for western blots as described previously [12]. The cells were lysed using Mammalian Protein Extraction Reagent (Pierce, Rockford, Ill.) according the manufacturer's instructions. The western blot membranes were incubated with antibodies against PR (C-19, Santa Cruz Biotech, CA, or Ab-7, Neomarkers, Lab Vision Corp, Fremont, Calif.), PRB (Ab-6, Neomarkers), ERKs (SC-94, Santa Cruz Biotech), E-Cad (610182, BD), Actin (1-19, Santa Cruz Biotech), DnmtI, Dnmt3a and Dnmt3b (H-300, H-295, and H-230, respectively, Santa Cruz Biotech), RARβ (SC-14028, Santa Cruz Biotech), PTEN Ab32199, Abcam), p16 (SC-1207, Santa Cruz Biotech), Rb (SC-50, Santa Cruz Biotech), or glucocorticoid receptors (GRs) (SC-1004, Santa Cruz Biotech) overnight at 4° C., at a concentration of 2 µg/ml in PBST (0.8% NaCl, 0.02% KCl, 0.144% Na2PO4, 0.024% KH2PO4, pH 7.4, 0.1% Tween 20). The band intensities from 3 to 4 different tumor samples indifferent western blots were quantified using Image Quant software.

Immunofluorescence.

Frozen sections or cells grown in chamber slides, fixed in 70% ethanol for 1 h, were incubated with antibodies recognizing Dnmt1, Dnmt3a, Dnmt3b, PRA (Ab-7), RPB (Ab-6), or GR, in blocking buffer at a 1:200 dilution overnight at 4° C. They were then incubated with a FITC conjugated anti-rabbit (FI-1000, Vector Laboratories Burlingame, Calif.; 1:100 dilution) secondary antibody for 1 h at room temperature. Nuclei were stained with propidium iodide (PI, Sigma). The slides were mounted using Vectashield (Vector Laboratories). Stained cells were analyzed using a Nikon Eclipse E800 Laser Confocal Microscope and EZ-C1 2.20 software. Cell staining was quantified using Image Quant software.

Immunohistochemistry.

Sections of formalin-fixed, paraffin-embedded tissue were processed as previously described [28] and stained with the PRA-specific antibody (C-19) using the avidin-biotin-peroxidase complex technique (Vectastain Elite ABC kit; Vector), as described previously [28].

Morphological Studies.

H&E stained sections of livers, spleens, and kidneys from the 5azadC-treated mice (1 mg/kg or 0.75 mg/kg/every other day; n=5) were studied by an expert mouse pathologist. The percentage of tumor stoma versus tumor parenchyma was quantified with the ImageJ software in treated and untreated tumors. The stromal area in relation to the total tumor area was calculated in five representative fields of each sample, using 400× magnification, in three different tumor samples of each group, and the mean±SEM was calculated. Mitotic and apoptotic indices were counted in 10 and 15 high-power fields (HPFs), respectively, of each section, using 1000× magnification, and expressed as the mean±SEM of the percentage of the ratios between the total number of events (mitosis or apoptosis) and the total cell number per HPF. Mitotic figures were identified morphologically by the condensed "hairy" aspect of the chromosomes. Morphological identification of apoptosis was performed according to criteria previously reported, which correlated with the deoxynucleotidyl transferase mediated dUTP-biotin nick end labeling (TUNEL) method [28].

Statistical Analysis.

Data were analyzed using ANOVA and the Tukey multiple post t test (for multiple samples) or the Student's t test to compare the mean±SD using Graph Prism 4.0 software.

Tumor growth curves were studied using regression analysis and slopes compared using analysis of variance followed by parallelism analysis.

Results

Carcinomas with Acquired Resistance Regain their Hormone Responsiveness and the PRA/PRB Ratio when Cultured on Plastic.

Previously the inventors reported on several MPA independent variants that were generated from MPA-induced mammary carcinomas. The two tumor families used herein are depicted in FIG. 7. C4-HD tumor gave rise to C4-HI, which responds to antiprogestin treatment, and to C4-2-HI, which showed constitutive hormone resistance Similarly, 59-HD gave rise to 59-HI, a constitutive-resistant tumor, and to 59-2-HI, an antiprogestin-responsive variant [8]. From both of the antiprogestin-responsive tumors, we developed variants with acquired resistance (C4-HIR and 59-2-HIR) by selective pressure using RU-486 [13] (FIGS. 7, 8a). We have recently reported an inverse PRA/PRB ratio in responsive tumors (C4-HI, 59-2-HI) as compared with the resistant variants, with PRA being higher than PRB [13].

We were interested in evaluating whether carcinoma-associated fibroblasts contributed to the resistant phenotype; so, we first evaluated hormone responsiveness in purified epithelial cells from the three different tumor types. As expected, MPA induced a strong proliferative effect in C4-HI cells ($P<0.001$), which was abolished by RU-486 or ZK 230211 ($P<0.001$), whereas no differences were observed in C4-2-HI cells. However, unexpectedly, a proliferative effect was observed in the acquired resistant C4-HIR cells treated with MPA ($P<0.001$), which was abolished by RU-486 or ZK 230211 ($P<0.001$; FIG. 7a), indicating that acquired antiprogestin resistance but not constitutive resistance is reversed by in vitro culturing. Similar results were obtained with the 59 family of tumors (not shown).

The expression level of PRA and PRB in purified tumor cells from the three tumors growing on plastic was analyzed using western blot (FIG. 7b) and immunofluorescence (FIG. 7c). The PR isoform ratio in C4-HIR cells became similar to that of the responsive tumors (FIG. 7b, c), whereas the PR isoform pattern did not change in the constitutive antiprogestin-resistant tumors (FIG. 7c). These results suggest that different mechanisms regulate PRA silencing in tumors with constitutive and acquired antiprogestin resistance.

The Incubation of Epithelial Tumor Cells with Carcinoma-Associated Fibroblasts does not Modify their Hormone Responsiveness.

In order to investigate whether carcinoma associated fibroblasts could be participating in the acquired antiprogestin-resistant phenotype, purified epithelial cells from the antiprogestin-responsive tumor C4-HI or from the acquired antiprogestin-resistant tumor C4-HIR were co-cultured with equal amounts of their own carcinoma-associated fibroblasts or with those from the other tumor, as described previously [32]. In both cases, MPA stimulated, and RU-486 inhibited co-culture cell proliferation, suggesting that the presence of carcinoma-associated fibroblasts does not change the hormone responsiveness.

PRA Expression is Silenced by Methylation Only in Constitutive Antiprogestin-Resistant Tumors.

In order to investigate the mechanisms involved in PRA silencing, we carried out methylation analyses of the PRA promoter using the same tumors studied above. Different CpG sites were analyzed with four different pairs of primers (SEQ ID NOS 4-19, respectively, in order of appearance) (Table 1):

TABLE 1

Sequence of primers selected for PCR methylation studies with their annealing temperatures and PCR conditions

| Primers | Sequence | Annealing T (° C.) |
|---|---|---|
| PR1 F M | 5'GGGCGGGTTTTTTTAGAGC 3' | 57 |
| PR1 R M | 5'CTCGTTCTCCTACAACGACA 3' | 58 |
| PR1 F UM | 5'TTTTGGGTGGGTTTTTTTAGAGT 3' | 58 |
| PR1 R UM | 5'TACTCATTCTCCTACAACAACAA 3' | 58 |
| PR2 F M | 5'ATTTTATCGTTATCGGGATAGCGC 3' | 62 |
| PR2 R M | 5'ATAAATATAAAATCGCAAAACCCG 3' | 57 |
| PR2 F UM | 5'TATTTTATTGTTATTGGGATAGTGT 3' | 56 |
| PR2 R UM | 5'AATAAATATAAAATCACAAAACCCA 3' | 54 |
| PR3 F M | 5'GAAGAAATACGAAAAAAAGTTTTTC 3' | 56 |
| PR3 R M | 5'ATAAATATAAAATCGCAAAACCCG 3' | 57 |
| PR3 F UM | 5'AGAAGAAATATGAAAAAAAGTTTTTT 3' | 54 |
| PR3 R UM | 5'AATAAATATAAAATCACAAAACCCA 3' | 54 |
| PR4 F M | 5'GTTTTTTATACGTTTGGCGTTTC 3' | 58 |
| PR4 R M | 5'CACGTCGAACAACGACTACT 3' | 58 |
| PR4 F UM | 5'AGGTTTTTTATATGTTTGGTGTTTT 3' | 56 |

TABLE 1-continued

Sequence of primers selected for
PCR methylation studies with their
annealing temperatures and PCR conditions

| PR4 R UM | 5'CTCCACATCAAACAACAACTACT 3' | 59 |

| Denaturalization temperature and duration | Annealing T (° C.) | Extension temperature and duration | Final extension |
|---|---|---|---|
| 94° C.- 5 min | 94° C.- 35 cycles of 45 s | 45 s | 72° C.- 45 s | 72° C.- 10 min |

FIG. 9(a) shows a schematic of the PR promoter, with the locations of the CpG sites of both PR isoforms. As expected, only unmethylated CpG islands were observed in the two antiprogestin-responsive tumors (C4-HI and 59-2-HI; FIG. 9(b)). Hypermethylation of the PRA promoter was detected in the two constitutive antiprogestin-resistant tumors (C4-2-HI and 59-HI), whereas the PRA promoter in both tumors with acquired antiprogestin resistance (C4-HIR and 59-2-HIR) was unmethylated (FIG. 9(b)). Although we observe some methylated CpG islands using the PR1 pair of primers that are included in the PRB promoter, the density is not enough for these islands to qualify for a mechanism of gene silencing by promoter methylation (http://www.ensembl.org/Mus_musculus/index.html; [30]). In these experiments, DNA from normal lymphocytes treated with SssI methyltransferase was used as the methylated control, while untreated DNA was included as an unmethylated control (FIG. 9(c)).

The PCR products from the reactions using the PR4 primer pair and DNA from the antiprogestin-responsive tumors and the tumors with acquired and constitutive antiprogestin resistance were cloned and sequenced to analyze the degree of CpG island methylation. Whereas 100% of the CpG sites were unmethylated in the responsive and acquired resistant tumors (C4-HI, 59-2-HI, C4-HIR and 59-2-HIR), 89.9+2.2% of the CpG sites were methylated in C4-2-HI, and 88. 8±3.2% of the CpG sites in 59-HI constitutive-resistant tumors. A diagram illustrating the CpG sites that were methylated in one representative sample is shown in FIG. 3(d).

We conclude that methylation of CpG sites at the PRA promoter explains PRA silencing only in the constitutive antiprogestin-resistant tumors.

In Vitro Treatment with 5azadC Induces PRA Expression and RU-486 responsiveness in constitutive-resistant purified epithelial cells.

The strong correlation between PRA expression and the antiprogestin RU-486 responsiveness suggested that constitutive-resistant tumors might be re-sensitized to RU-486 treatment after the restoration of PRA expression. Therefore, we treated these tumors with a demethylating agent, and evaluated their PRA expression and antiprogestin responsiveness.

Primary cell cultures from the two constitutive-resistant tumors, C4-2-HI and 59-HI, were treated with 5azadC ($5 \times 10^{-7}$ and $5 \times 10^{-6}$ M, respectively) for 96 h. An increase in PRA expression ($P<0.001$) was observed using immunofluorescence and western blot in both tumor cells (FIG. 10(a)(b)). However, no significant changes were observed using the Ab-6 antibody, which only stains PRB (FIG. 19(a)).

In order to further investigate whether the restoration of PRA expression by 5azadC treatment could induce antiprogestin responsiveness, primary cultures of C4-2-HI and 59-HI cells were treated with 5azadC plus RU-486, and cell proliferation was evaluated using (3H)-thymidine incorporation. As observed in FIG. 4c, the proliferation of cells treated with 5 µM 5azadC and 100 nM RU-486 was inhibited ($P<0.001$), whereas treatment with 5azadC or RU-486 alone did not alter cell proliferation.

In vivo 5azadC treatment induces PRA expression and RU-486 responsiveness in constitutive antiprogestin-resistant tumors.

In order to investigate whether this restoration of PRA expression and RU-486 responsiveness could be achieved in vivo, mice carrying palpable constitutive-resistant tumors, C4-2-HI and 59-HI, were treated with vehicle, 5azadC, RU-486, or 5azadC in combination with RU-486. Interestingly, as observed in FIG. 5a, the combination of 5azadC and RU-486 significantly inhibited tumor growth in both cases. Morphological signs of tumor regression, including increased stromal tissue intermingled with the epithelial nests ($P<0.001$), increased apoptosis, and a decreased mitotic index, were observed in tumors treated with the combination of RU-486 and 5azadC (FIG. 11(b); Table 2). However, no significant differences were observed in tumors treated with RU-486 or 5azadC alone.

TABLE 2

Apoptotic and mitotic indices observed in tumors treated with the combination of RU-486 and 5azadC

| | 59-HT mean ± SEM | | C4-2-HT mean ± SEM | |
|---|---|---|---|---|
| | Control | 5azadC + RU-486 | Control | 5azadC + RU-486 |
| Apoptotic index | 1 ± 0.19 | 3.67 ± 0.09*** | 1 ± 0.22 | 3.31 ± 0.02*** |
| Mitotic index | 1 ± 0.069 | 0.49 ± 0.21* | 1 ± 0.08 | 0.38 ± 0.1* |

*$P < 0.05$ and
***$P < 0.001$ treated versus control

Figure 11A:
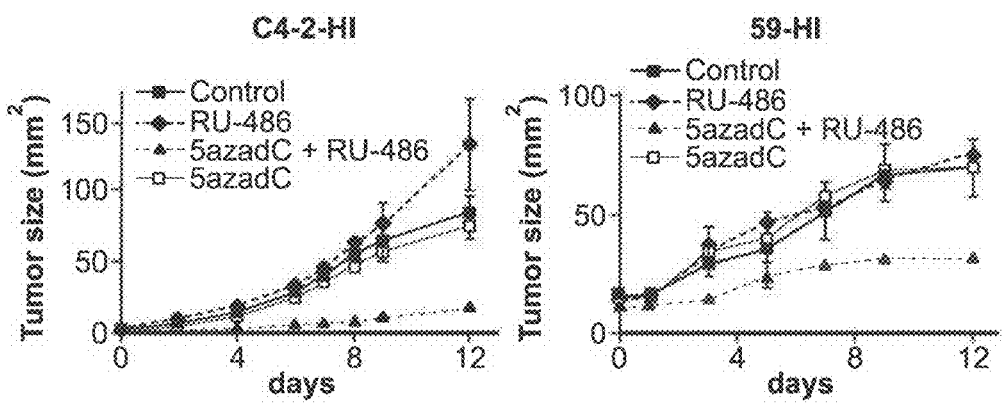
Figure 11B:
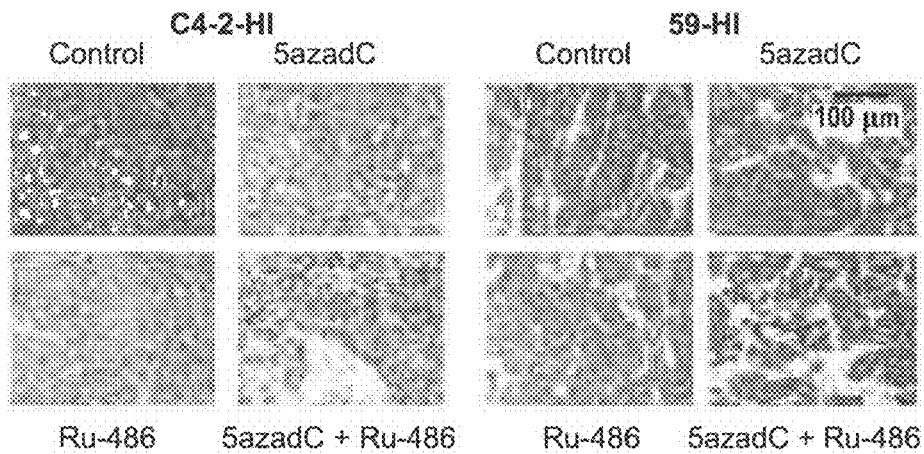
Figure 11C:
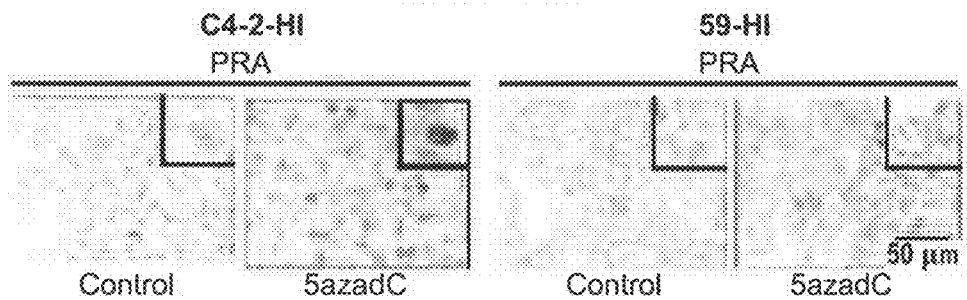
Figure 11D:
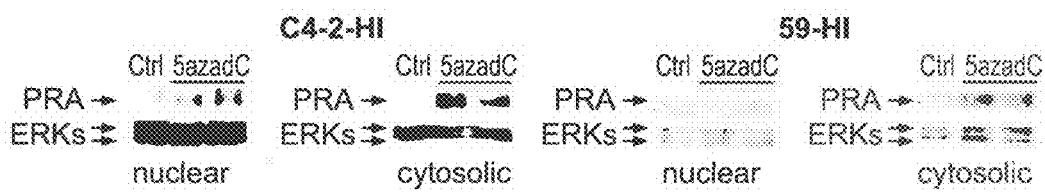

In addition, an increase in nuclear and cytoplasmic PRA staining was observed in 5azadC-treated C4-2-HI tumors compared with control tumors (FIG. 11(c)). Nuclear staining was heterogeneous and punctate. In 5azadC-treated 59-HI tumors, only cytoplasmic and perinuclear PRA staining was observed. It may be possible that in the absence of ligand, PRA accumulates in the cytoplasm. Western blots confirmed the increase in PRA expression in both C4-2-HI and 59-HI tumors (P<0.01). The PRB level, on the other hand, was not significantly modified by 5azadC treatment (not shown). Histological evaluation of liver, spleen, and kidney indicated no signs of toxicity due to 5azadC-treatment with the two doses used (0.75 and 1 mg/kg).

Furthermore, in order to test whether 5azadC treatment could modify the antiprogestin response of C4-HIR tumors, in which PRA is silenced by mechanisms other than PRA methylation, these tumors were similarly treated. As expected, no inhibition in tumor growth was observed in these 5azadC- and RU-486-treated mice (FIG. 12).

Constitutive Antiprogestin-Resistant Tumors Express High Levels of DNA methyltransferases.

DnmtI and Dnmt3a/b regulate CpG island methylation, and it has been proposed that 5azadC targets Dnmts [35, 36]. Therefore, we were interested in studying Dnmt expression in responsive and resistant antiprogestin tumors.

Figure 13A:
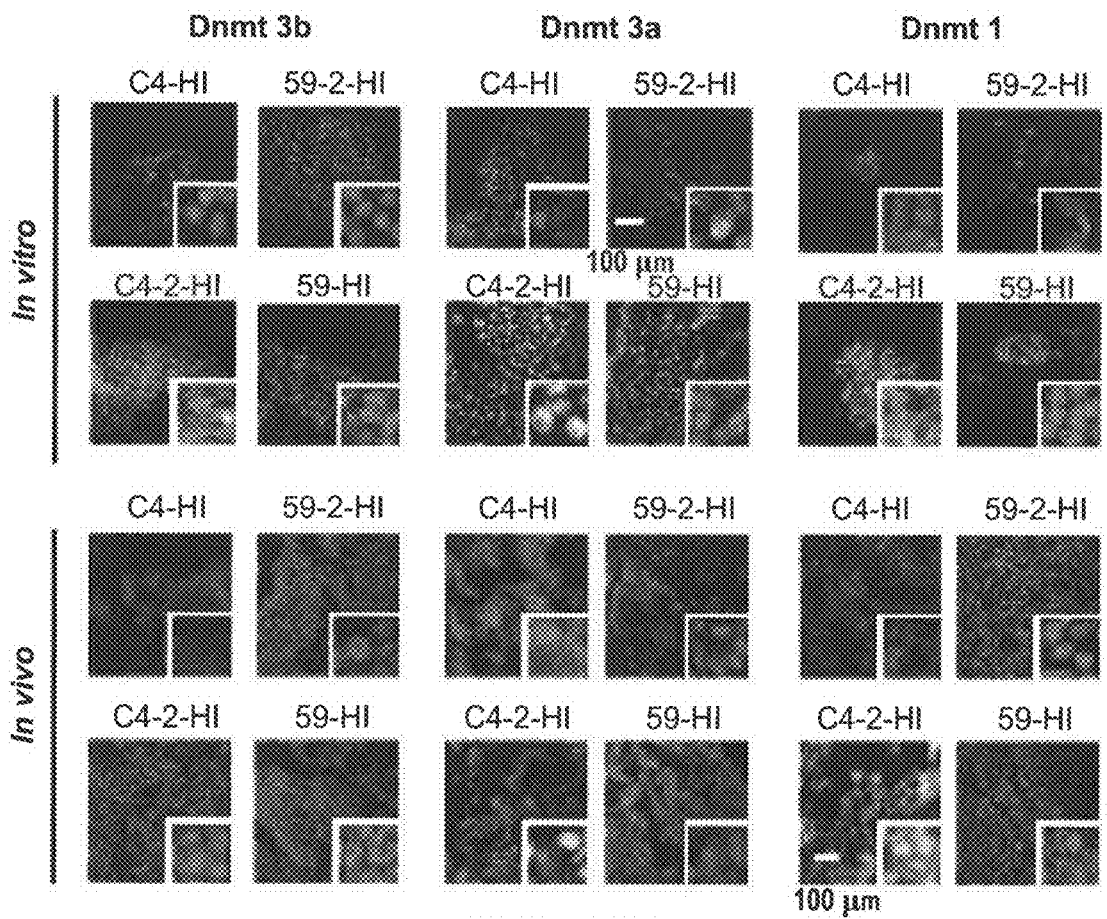
Figure 13B:
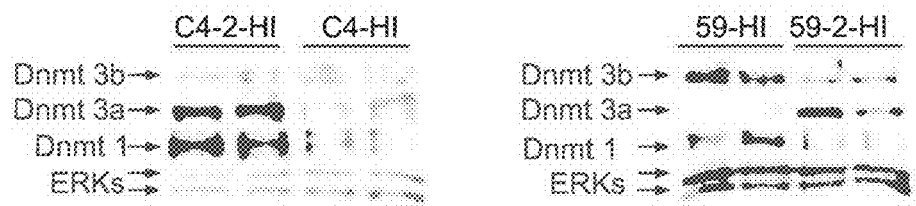
Figure 13C:
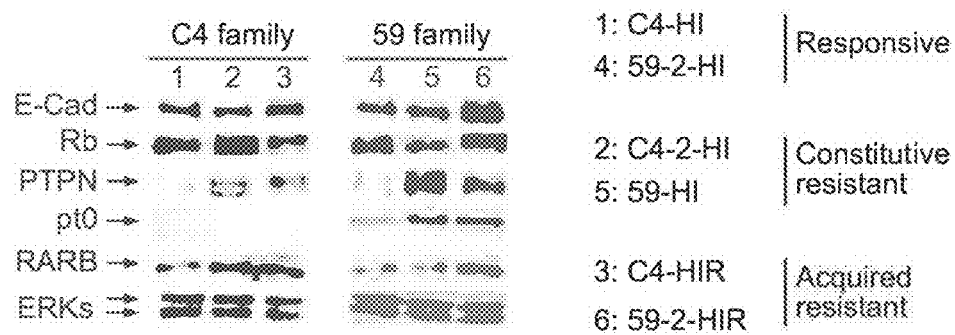

Immunofluorescence experiments demonstrated that C4-2-HI cells cultured on plastic expressed a higher level of the three Dnmts than the C4-HI cells (Dnmt3a/b, P<0.05; DnmtI: P<0.001), and that the 59-HI cells showed a higher level of Dnmt3b than the 59-2-HI cells (P<0.001; FIG. 13(a)). When tumor sections were used, similar results were obtained, although nuclear expression of DnmtI 3a was higher than in cells cultured in plastic, suggesting that tumor microenvironment may be regulating Dnmt activation (FIG. 13(a)). These studies were corroborated using western blots (FIG. 13(b)). These data suggest that increased levels of DnmtI and 3b are related to the increased PRA methylation in constitutive-resistant tumors. The greater 5azadC responsiveness of C4-2-HI compared with 59-HI (FIGS. 10(c), 11(a)) is consistent with the higher levels of the three Dnmts.

E-Cadherin, p16, PTEN, Rb, and RARβ are not Silenced in Constitutive Antiprogestin-Resistant Tumors.

The inventors were interested in investigating whether the increased Dnmts levels in constitutive-resistant tumors silences other genes that are usually regulated by methylation. Thus, the inventors compared the expression of E-cadherin, p16, Rb, PTEN and RARβ. As observed in FIG. 13(c), the expression of these proteins did not follow the same regulation pattern as PRA, demonstrating tumor-specific differences and indicating that silencing of PRA in constitutive-resistant tumors is a specific phenomenon.

Glucocorticoid Receptor Expression Decreases in Constitutive Antiprogestin-Resistant Tumors Treated with 5azadC.

Figure 14A:
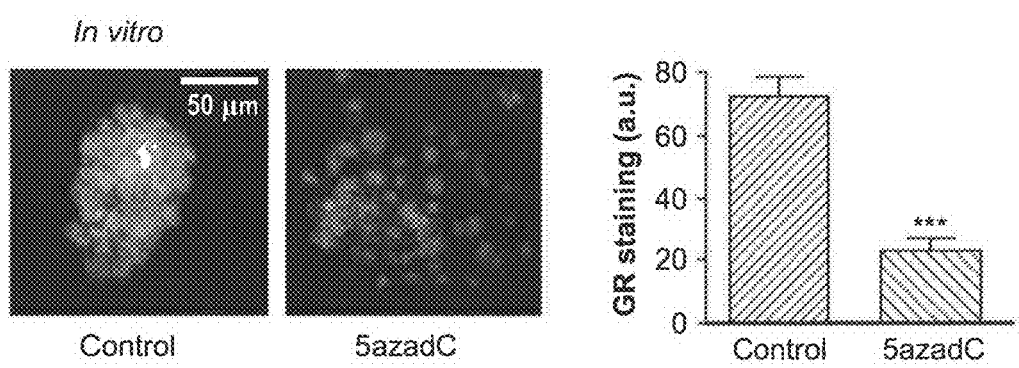
Figure 14B:
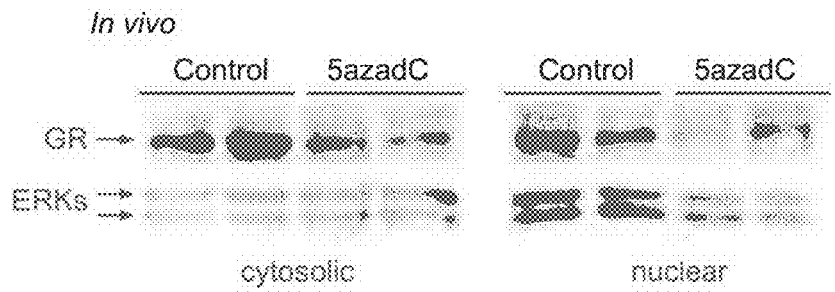

In order to investigate whether 5azadC treatment could be inducing GR expression, and to discard a possible effect of RU-486 mediated by GR, studied GR expression in C4-2-HI tumors treated with or without 5azadC in vitro and in vivo was studied. The expression of GR decreased in C4-2-HI cells treated with 5azadC (immunofluorescence; FIG. 14(a)) and in tumors from 5azadC-treated mice (western blots; FIG. 14(b)), ruling out a possible GR-mediated effect.

Discussion

In previous articles, the inventors have observed a correlation between PRA expression and antiprogestin responsiveness [12]: Antiprogestin-resistant mammary tumors show a lower expression level of PRA than do responsive tumors. Moreover, we have shown that the reacquisition of hormone sensitivity in tumors with acquired resistance was accompanied by the restoration of PRA expression [13]. In this study, it was clearly demonstrate that PRA expression is silenced in constitutive antiprogestin-resistant tumors by methylation of the PRA promoter. Treatment with a demethylating agent restores PRA expression and antiprogestin responsiveness only in the constitutive-resistant tumors. These tumors showed high expression levels of DnmtI and 3a/b, which may be responsible for the increased PRA methylation. The mechanism by which PRA is silenced in tumors with acquired antiprogestin resistance remains to be elucidated.

There exist very few studies regarding PR silencing in breast cancer. In ER- and PR negative breast cancers, it has been shown that the PR promoter is methylated in 39-46% of tumors [21] Similar findings have been reported by others [34, 35]. More recently, Vasilatos et al. [36] studied a series of genes, among them PRB and PRA, and have reported that CpG island methylation of PRA together with RARβ (M4), INK4x/ARF, and HIN-1 may predict non-BRCA1/2-associated mammary carcinogenesis and tumor progression. There are, however, no clinical or experimental studies suggesting that PR or ERx methylation is the possible epigenetic mechanism related to acquired hormone resistance. These studies here clearly demonstrate that different epigenetic mechanisms regulate constitutive and acquired resistance, with CpG methylation of hormone receptor genes being involved in the former.

Most of the studies in experimental models have focused on ERx methylation in MDAMB-231 cells, and PR, most specifically PRB, has been evaluated only as an ERx-regulated gene. In these cells, it has been demonstrated that both ER and PR are silenced by promoter methylation. Treatment with demethylating agents restored ERx and PRB expression, but not PRA expression [19]. The same group demonstrated that ERx was able to restore PR expression even if PR was still methylated, since the exogenous transfection of ERx was able to restore PRB expression [37]. However, a different picture has been reported in MCF-7-derived clones. In this system, it has been shown that disruption of ERx signaling alone induces PR methylation and that both re-expression of ERx and PR demethylation are necessary for PR re-expression [35]. Interestingly, MDA-MB-231 cells treated with demethylating agents in vitro acquired tamoxifen responsiveness [38]. In addition, MDA-MB-435 cells treated in vivo with a combination of Dnmt and HDAC (histone deacetylase) inhibitors showed an inhibition of tumor growth that was more evident in ovariectomized animals [39]. However, there appear to be no reports examining the in vivo effect of antiestrogens or tamoxifen in combination with demethylating agents.

A strength of this study is that PRA methylation for the first time was demonstrated in a mouse model using two different spontaneous constitutive-resistant tumors, and that in both cases antiprogestin responsiveness in vivo could be restored after PRA re-expression. This is important not only in the context of the experiments described herein, but, in addition; they support the hypothesis that high levels of PRA are predictive of antiprogestin responsiveness. Interestingly, although we have observed an increase in PRA expression in 5azadC treated tumors, in most cases, the expression level of PRB was still higher than the expression level of PRA. This might be because only some cells re-expressed PRA following treatment with 5azadC, as observed by immunohistochemistry. This heterogeneity may explain why the tumors only showed decreased growth and did not regress completely.

It has been proposed that impaired ER signaling may be enough to induce methylation of ER target genes, among them PR [35]. Since all of these tumors come from hormone-dependent tumors that express a high level of ERx, PRA, and PRB, it is possible that in the hormone-independent switch, these tumors suffered a disruption in ER signaling that, in turn, induced PRA methylation. This kind of mechanism has been recently shown in MCF-7 cells cultured in the presence of an ERx-specific siRNA [35]. However, no pattern was found here demonstrating that constitutive antiprogestin-resistant tumors had lower ERx levels than the responsive tumors.

Here, four different primer pairs were used to examine ERx promoter methylation without finding any clear differences between the methylation pattern of resistant and responsive tumors (unpublished data). Moreover, the inventors have evidence that PRB is still important for the growth of these tumors, as antisense oligonucleotides targeting PR inhibit cell proliferation (unpublished data). Another possibility is that the increase in the expression of the Dnmts observed in the constitutive-unresponsive tumors may be responsible for methylating several genes that favor MPA-independent tumor growth: among them PRA. In support of this hypothesis, all the constitutive-resistant tumors of this model grew faster in vivo and in vitro, showing a stromal-independent pattern of growth. However, when 5azadC was used alone, no significant inhibition of tumor growth was observed. The restitution of suppressor functions by 5azadC treatment should have induced an inhibitory effect per se. Instead, we only observed the inhibitory effect in the presence of RU-486. In contrast, the E-cadherin, p16, PTEN, Rb, and RARβ genes, all known to be regulated by DNA methylation, did not follow the same pattern of expression as PRA. Taken together, this suggests that these tumors exhibit specific PRA methylation.

There is compelling experimental and clinical evidence indicating that progestins play an important role in the induction and maintenance of the neoplastic phenotype in the mammary gland [40-48]; and thus, the PR may be a valid therapeutic target. In this regard, several studies have demonstrated therapeutic effects of antiprogestins either alone or together with antiestrogens in different experimental models [49-51].

RU-486 is a potent antiprogestin and an antiglucocorticoid [52]. The key role of PR in our experimental model has already been assessed since two antiprogestins with less antiglucocorticoid effects such as onapristone (ZK 98299) and ZK 230211 also induced tumor regression [13, 53]. Moreover, PR antisense oligonucleotides inhibited tumor growth both in vivo and in vitro [54]. However, the possibility that 5azadC treatment would be increasing GR receptors had to be discarded. Interestingly, a decrease in GR expression was observed in 5azadC-treated tumors both in vivo and in vitro, suggesting that the involvement of GR in RU-486-induced inhibitory effect is unlikely.

Demethylating agents have been approved for use in hematologic malignancies, and they are used as differentiating agents [55]. Moreover, it has been proposed that they may decrease the "stemness" of the tumors and increase their differentiation [56]. Our data, together with those of others, suggest that the Dnmt inhibitors may be used temporarily to restore the expression of therapeutic targets [16, 38, and 56], in this case PRA.

Carcinoma-associated fibroblasts are key players regulating HI tumor growth in this model [32]. Recently, it has also been shown that these cells are capable of regulating gene silencing in epithelial tumor cells [57]. The inventors were interested in investigating whether carcinoma-associated fibroblasts from tumors with acquired resistance could change the hormone responsiveness of the epithelial cells. Surprisingly, although the inventors did not find any differences between both types of fibroblasts, we observed that epithelial cells with acquired resistance growing on plastic reacquired their hormone responsiveness and PRA expression. This highlights the reversibility of PRA expression, which can be induced by growth on plastic, estrogen treatment [13], and the duration of the absence of the hormone [13], but not by 5azadC treatment in tumors with acquired resistance. This suggests the involvement of different epigenetic mechanisms in the regulation of PRA silencing in acquired antiprogestin resistance.

In summary, the inventors have demonstrated PRA silencing by promoter methylation in constitutive antiprogestin-resistant tumors, and that this increased methylation could be correlated with a high expression level of Dnmts1 and 3b. In vitro and in vivo treatment with a demethylating agent, which was unable to decrease tumor growth, was able to restore PRA expression and antiprogestin sensitivity. These results support a therapeutic role for Dnmt inhibitors in combination with endocrine therapy for those tumors with a high expression level of Dnmts. The correlation between PRA expression and antiprogestin responsiveness supports the use of antiprogestins in breast cancer which should be therapeutically exploited.

REFERENCES FOR EXAMPLE 2

1. Santen R J, Manni A, Harvey H, Redmond C (1990) Endocrine treatment of breast cancer in women. Endocr Rev 11:221-265.
2. Normanno N, Di Maio M, De Maio E, De Luca A, de Matteis A, Giordano A, Perrone F (2005) Mechanisms of endocrine resistance and novel therapeutic strategies in breast cancer. Endocr Relat Cancer 12:721-747.
3. Kastner P, Krust A, Turcotte B, Stropp U, Tora L, Gronemeyer H, Chambon P (1990) Two distinct estrogen-regulated promoters generate transcripts encoding the two functionally different human progesterone receptor forms A and B. EMBO J 9:1603-1614.
4. Kraus W L, Katzenellenbogen B S (1993) Regulation of progesterone receptor gene expression and growth in the rat uterus: modulation of estrogen actions by progesterone and sex steroid hormone antagonists. Endocrinology 132: 2371-2379.
5. Richer J K, Jacobsen B M, Manning N G, Abel M G, Wolf D M, Horwitz K B (2002) Differential gene regulation by the two progesterone receptor isoforms in human breast cancer cells. J Biol Chem 277:5209-5218.
6. Hopp T A, Weiss H L, Hilsenbeck S G, Cui Y, Allred D C, Horwitz K B, Fuqua S A (2004) Breast cancer patients with progesterone receptor P R-A-rich tumors have poorer disease free survival rates. Clin Cancer Res 10:2751-2760.
7. Long B J, Jelovac D, Handratta V, Thiantanawat A, MacPherson N, Ragaz J, Goloubeva O G, Brodie A M (2004) Therapeutic strategies using the aromatase inhibitor letrozole and tamoxifen in a breast cancer model. J Natl Cancer Inst 96:456-465

8. Macedo L F, Sabnis G J, Goloubeva O G, Brodie A (2008) Combination of anastrozole with fulvestrant in the intratumoral aromatase xenograft model. Cancer Res 68:3516-3522,
9. Lanari C, Molinolo A A, Pasqualini C D (1986) Induction of mammary adenocarcinomas by medroxyprogesterone acetate in BALB/c female mice. Cancer Lett 33:215-223.
10. Molinolo A A, Lanari C, Charreau E H, Sanjuan N, Pasqualini C D (1987) Mouse mammary tumors induced by medroxyprogesterone acetate: immunohistochemistry and hormonal receptors. J Natl Cancer Inst 79:1341-1350.
11. Lanari C, Lamb C A, Fabris V T, Helguero L A, Soldati R, Bottino M C, Giulianelli S, Cerliani J P, Wargon V, Molinolo A (2009) The MPA mouse breast cancer model: evidence for a role of progesterone receptors in breast cancer. Endocr Relat Cancer 16:333-350.
12. Helguero L A, Viegas M, Asaithamby A, Shyamala G, Lanari C, Molinolo A A (2003) Progesterone receptor expression in medroxyprogesterone acetate-induced murine mammary carcinomas and response to endocrine treatment. Breast Cancer Res Treat 79:379-390.
13. Wargon V, Helguero L A, Bolado J, Rojas P, Novaro V, Molinolo A, Lanari C (2009) Reversal of antiprogestin resistance and progesterone receptor isoform ratio in acquired resistant mammary carcinomas. Breast Cancer Res Treat 116:449-460.
14. Momparler R L, Bovenzi V (2000) DNA methylation and cancer. J Cell Physiol 183:145-154.
15. Palii S S, Van Emburgh B O, Sankpal U T, Brown K D, Robertson K D (2008) DNA methylation inhibitor 5-Aza-2 0-deoxycytidine induces reversible genome-wide DNA damage that is distinctly influenced by DNA methyltransferases 1 and 3B. Mol Cell Biol 28:752-771.
16. Brinkman J A, El Ashry D (2009) E R re-expression and re-sensitization to endocrine therapies in E R-negative breast cancers. J Mammary Gland Biol Neoplasia 14:67-78.
17. Jones P A, Baylin S B (2002) The fundamental role of epigenetic events in cancer. Nat 20 Rev Genet 3:415-428.
18. Roll J D, Rivenbark A G, Jones W D, Coleman W B (2008) DNMT3b over expression contributes to a hypermethylator phenotype in human breast cancer cell lines. Mol Cancer 7:15.
19. Ferguson A T, Lapidus R G, Baylin S B, Davidson N E (1995) Demethylation of the estrogen receptor gene in estrogen receptornegative breast cancer cells can reactivate estrogen receptor gene expression. Cancer Res 55:2279-2283.
20. Ferguson D J, Anderson T J (1981) Morphological evaluation of cell turnover in relation to the menstrual cycle in the "resting" human breast. Br J Cancer 44:177-181.
21. Lapidus R G, Ferguson A T, Ottaviano Y L, Parl F F, Smith H S, Weitzman S A, Baylin S B, Issa J P, Davidson N E (1996) Methylation of estrogen and progesterone receptor gene 5 0 CpG islands correlates with lack of estrogen and progesterone receptor gene expression in breast tumors. Clin Cancer Res 2:805-810.
22. Nass S J, Herman J G, Gabrielson E, Iversen P W, Parl F F, Davidson N E, Graff J R (2000) Aberrant methylation of the estrogen receptor and E-cadherin 5 0 CpG islands increases with malignant progression in human breast cancer. Cancer Res 60:4346-4348.
23. Bird A P (1986) CpG-rich islands and the function of DNA methylation. Nature 321:209-213.
24. Lapidus R G, Nass S J, Davidson N E (1998) The loss of estrogen and progesterone receptor gene expression in human breast cancer. J Mammary Gland Biol Neoplasia 3:85-94.
25. Ottaviano Y L, Issa J P, Parl F F, Smith H S, Baylin S B, Davidson N E (1994) Methylation of the estrogen receptor gene CpG island marks loss of estrogen receptor expression in human breast cancer cells. Cancer Res 54:2552-2555.
26. Yang X, Yan L, Davidson N E (2001) DNA methylation in breast cancer. Endocr Relat Cancer 8:115-127.
27. Institute of Laboratory Animal Resources CoLSNRC (1996) Guide for the care and use of laboratory animals. National Academy Press, Washington, D C.
28. Vanzulli S, Efeyan A, Benavides F, Helguero L, Peters G, Shen J, Conti C J, Lanari C, Molinolo A (2002) p21, p27 and p53 in estrogen and antiprogestin-induced tumor regression of experimental mouse mammary ductal carcinomas. Carcinogenesis 23:749-757.
29. Frommer M, McDonald L E, Millar D S, Collis C M, Watt F, Grigg G W, Molloy P L, Paul C L (1992) A genomic sequencing protocol that yields a positive display of 5-methylcytosine residues in individual DNA strands. Proc Natl Acad Sci USA 89:1827-1831.
30. Hagihara K, Wu-Peng X S, Funabashi T, Kato J, Pfaff D W (1994) Nucleic acid sequence and DNase hypersensitive sites of the 5 0 region of the mouse progesterone receptor gene. Biochem Biophys Res Commun 205:1093-1101.
31. Lanari C, Luthy I, Lamb C A, Fabris V, Pagano E, Helguero L A, Sanjuan N, Merani S, Molinolo A A (2001) Five novel hormoneresponsive cell lines derived from murine mammary ductal carcinomas: in vivo and in vitro effects of estrogens and progestins. Cancer Res 61:293-302.
32. Giulianelli S, Cerliani J P, Lamb C A, Fabris V T, Bottino M C, Gorostiaga M A, Novaro V, Gongora A, Baldi A, Molinolo A, Lanari C (2008) Carcinoma-associated fibroblasts activate progesterone receptors and induce hormone independent mammary tumor growth: A role for the FGF-2/FGFR-2 axis. Int J Cancer 123:2518-2531.
33. Lamb C, Simian M, Molinolo A, Pazos P, Lanari C (1999) Regulation of cell growth of a progestin-dependent murine mammary carcinoma in vitro: progesterone receptor involvement in serum or growth factor-induced cell proliferation. J Steroid Biochem Mol Biol 70:133-142.
34. Mirza S, Sharma G, Prasad C P, Parshad R, Srivastava A, Gupta S D, Ralhan R (2007) Promoter hypermethylation of TMS1, BRCA1, ERalpha and PRB in serum and tumor DNA of invasive ductal breast carcinoma patients. Life Sci 81:280-287.
35. Leu Y W, Yan P S, Fan M, Jin V X, Liu J C, Curran E M, Welshons W V, Wei S H, Davuluri R V, Plass C, Nephew K P, Huang T H (2004) Loss of estrogen receptor signaling triggers epigenetic silencing of downstream targets in breast cancer. Cancer Res 64:8184-8192.
36. Vasilatos S N, Broadwater G, Barry W T, Baker J C Jr, Lem S, Dietze E C, Bean G R, Bryson A D, Pilie P G, Goldenberg V, Skaar D, Paisie C, Torres-Hernandez A, Grant T L, Wilke L G, Ibarra-Drendall C, Ostrander J H, D'Amato N C, Zalles C, Jirtle R, Weaver V M, Seewaldt V L (2009) CpG island tumor suppressor promoter methylation in non-BRCA-associated early mammary carcinogenesis. Cancer Epidemiol Biomarkers Prev 18:901-914.

37. Ferguson A T, Lapidus R G, Davidson N E (1998) Demethylation of the progesterone receptor CpG island is not required for progesterone receptor gene expression. Oncogene 17:577-583.
38. Sharma D, Saxena N K, Davidson N E, Vertino P M (2006) Restoration of tamoxifen sensitivity in estrogen receptor-negative breast cancer cells: tamoxifen-bound reactivated E R recruits distinctive corepressor complexes. Cancer Res 66:6370-6378.
39. Fan J, Yin W J, Lu J S, Wang L, Wu J, Wu F Y, Di G H, Shen Z Z, Shao Z M (2008) E R alpha negative breast cancer cells restore response to endocrine therapy by combination treatment with both HDAC inhibitor and DNMT inhibitor. J Cancer Res Clin Oncol 134:883-890.
40. Pazos P, Lanari C, Meiss R, Charreau E H, Pasqualini C D (1992) Mammary carcinogenesis induced by N-methyl-N-nitrosourea (MNU) and medroxyprogesterone acetate (MPA) in BALB/c mice. Breast Cancer Res Treat 20:133-138.
41. Russo I H, Gimotty P, Dupuis M, Russo J (1989) Effect of medroxyprogesterone acetate on the response of the rat mammary gland to carcinogenesis. Br J Cancer 59:210-216.
42. Aldaz C M, Liao Q Y, Paladugu A, Rehm S, Wang H (1996) Allelotypic and cytogenetic characterization of chemically induced mouse mammary tumors: high frequency of chromosome loss of heterozygosity at advanced stages of progression. Mol Carcinog 17:126-133.
43. Horwitz K B, Tung L, Takimoto G S (1996) Novel mechanisms of antiprogestin action. Acta Oncol 35:129-140.
44. Hyder S M, Murthy L, Stancel G M (1998) Progestin regulation of vascular endothelial growth factor in human breast cancer cells. Cancer Res 58:392-395.
45. Goepfert T M, McCarthy M, Kittrell F S, Stephens C, Ullrich R L, Brinkley B R, Medina D (2000) Progesterone facilitates chromosome instability (aneuploidy) in p53 null normal mammary epithelial cells. FASEB J 14:2221-2229.
46. Lydon J P, Ge G, Kittrell F S, Medina D, O'Malley B W (1999) Murine mammary gland carcinogenesis is critically dependent on progesterone receptor function. Cancer Res 59:4276-4284.
47. Women's Health Initiative (2002) Risks and benefits of estrogen plus progestin in healthy postmenopausal women principal results From the Women's Health Initiative randomized controlled trial. JAMA 288:321-333.
48. Beral V (2003) Breast cancer and hormone-replacement therapy in the Million Women Study. Lancet 362:419-427.
49. Klijn J G, Setyono-Han B, Foekens J A (2000) Progesterone antagonists and progesterone receptor modulators in the treatment of breast cancer. Steroids 65:825-830.
50. Moore M R (2004) A rationale for inhibiting progesterone-related pathways to combat breast cancer. Curr Cancer Drug Targets 4:183-189.
51. Gaddy V T, Barrett J T, Delk J N, Kallab A M, Porter A G, Schoenlein P V (2004) Mifepristone induces growth arrest, caspase activation, and apoptosis of estrogen receptorexpressing, antiestrogen-resistant breast cancer cells. Clin Cancer Res 10:5215-5225.
52. Horwitz K B (1992) The molecular biology of RU486. Is there a role for antiprogestins in the treatment of breast cancer? Endocr Rev 13:146-163.
53. Montecchia M F, Lamb C, Molinolo A A, Luthy I A, Pazos P, Charreau E, Vanzulli S, Lanari C (1999) Progesterone receptor involvement in independent tumor growth in MPA induced murine mammary adenocarcinomas. J Steroid Biochem Mol Biol 68:11-21.
54. Lamb C A, Helguero L A, Giulianelli S, Soldati R, Vanzulli S I, Molinolo A, Lanari C (2005) Antisense oligonucleotides targeting the progesterone receptor inhibit hormone independent breast cancer growth in mice. Breast Cancer Res 7:R1111-R1121.
55. Lyko F, Brown R (2005) DNA methyltransferase inhibitors and the development of epigenetic cancer therapies. J Natl Cancer Inst 97:1498-1506.
56. O'Brien C S, Howell S J, Farnie G, Clarke R B (2009) Resistance to endocrine therapy: are breast cancer stem cells the culprits? J Mammary Gland Biol Neoplasia 14:45-54.
57. Lin H J, Zuo T, Lin C H, Kuo C T, Liyanarachchi S, Sun S, Shen R, Deatherage D E, Potter D, Asamoto L, Lin S, Yan P S, Cheng A L, Ostrowski M C, Huang T H (2008) Breast cancer-associated fibroblasts confer AKT1-mediated epigenetic silencing of Cystatin M in epithelial cells. Cancer Res 68:10257-10266.

Example 3: DNMT and HDAC Inhibitors Resensitize Resistant Tumors to Antiprogestin Therapy in a Mouse Breast Cancer Model The aim of this study was to investigate whether the co-treatment with DNA methyltransferase (DNMT) and histone deacetylase (HDAC) inhibitors would further enhance the responsiveness of antiprogestin-resistant mammary tumors to RU-486 (antiprogestin). This study investigated the expression of HDAC1 in constitutive resistant tumors from the MPA breast cancer model and whether treatment of these tumors with 5azadC and trichostatin A (TSA) restored RU-486 responsiveness better than 5azadC alone.

Introduction

As a follow up of the experiments shown in Example 2, in which the treatment of constitutive resistant tumors with a demethylating agent sensitized the tumors to the inhibitory effect of antiprogestins, the inventors wished to improve the effect by adding an HDAC inhibitor. It is known that gene expression may be silenced by the aberrant methylation of CpG islands 1 and by histone deacetylation 2 and that treatment with demethylating agents such as 5-aza-2'deoxycytidine (5azadC) and HDAC inhibitors, as Trichostatin A (TSA), may induce gene re-expression 3-5. In tamoxifen (TAM) resistant cells, MDA-MB-231 REα-, the expression of the receptor can be recovered with the combined treatment of TSA and 5azadC and cells became sensitive to TAM therapy 2. In MDA-66 and HE-5 cells (they came from MDA-MB-231) PR mRNA increases when cells are treated with TSA and 5azadC 5. The aim of this study was to investigate whether the co-treatment with DNA methyltransferase (DNMT) and histone deacetylase (HDAC) inhibitors would enhance even more the responsiveness to RU-486. For this purpose, the inventors investigated the expression of HDAC1 in constitutive resistant tumors from the MPA breast cancer model and whether treatment of these tumors with 5azadC and trichostatin A (TSA; HDAC inhibitor) restored RU-486 responsiveness better than 5azadC alone.

Animals

Two-month-old virgin female BALB/c mice (IBYME Animal Facility) were used. Animal care and manipulation protocols were in agreement with institutional guidelines and the Guide for the Care and Use of Laboratory Animals 6.

Tumors

Mammary carcinomas from the MPA breast cancer model were used: C4-HI, and C4-2-HI are MPA independent variants from the C4 family; 59-2-HI and 59-HI are variants from the 59 family of tumors; C4-HI and 59-2-HI are antiprogestin-responsive tumors 7,8; and C4-2-HI and 59-HI are constitutive-resistant variants (FIG. 16) 9. Tumors were named before learning their antiprogestin responsiveness. All these tumor variants express ER and PR evaluated by binding, western blotting, and immunohistochemistry assays. However, low levels of PRA were detected in antiprogestin-resistant tumors 7,9. Tumors were transplanted by subcutaneous (s.c.) injection into the inguinal flank of BALB/c mice.

Reagents

The 5azadC, TSA and RU-486 (mifepristone) were purchased from Sigma-Aldrich (St. Louis, Mich.).

In Vivo Treatment with RU-486 5azadC and TSA

C4-2-HI and 59-HI tumors were transplanted s.c nearby the mammary gland 4th in syngenic mice, and measured every 2 days (length and width). Treatments were initiated when the tumors were palpable. The antiprogestin RU-486 (mifepristone) was inoculated s.c at a dose of 12 mg/kg/day. The mice were inoculated intraperitoneally (i.p.) with 0.75 mg/kg 5azadC every other day and s.c. with 1 mg/kg TSA every other day. All the experiments were repeated twice using five mice per group. The animals were euthanized after 13 days of treatment, and tumor samples were removed and frozen at −80 C or fixed in 10% formaldehyde.

Western Blots

Cytosolic or nuclear extracts were processed for western blots as described previously 9. The western blot membranes were incubated with antibodies against PR (C-19, Santa Cruz Biotech, CA) ERKs (SC-94, Santa Cruz Biotech), HDAC1 (SC-7872 Santa Cruz Biotech) 5 overnight at 4 PC, at a concentration of 2 lg/ml in PBST (0.8% NaCl, 0.02% KCl, 0.144% Na2PO4, 0.024% KH2PO4, pH 7.4, 0.1% Tween 20). The band intensities from 3 to 4 different tumor samples in different western blots were quantified using Image Quant software.

Immunofluorescence

Cells grown in chamber slides, fixed in 70% ethanol for 1 h, were incubated with antibodies recognizing PRA (C-19), in blocking buffer at a 1:200 dilution overnight at 4° C. They were then incubated with a FITC conjugated anti-rabbit (F1-1000, Vector Laboratories Burlingame, Calif.; 1:100 dilution) secondary antibody for 1 h at room temperature. Nuclei were stained with propidium iodide (PI, Sigma). The slides were mounted using Vectashield (Vector Laboratories). Stained cells were analyzed using a Nikon Eclipse E800 Laser Confocal Microscope and EZ-C1 2.20 software. Cell staining was quantified using Image Quant software.

Immunohistochemistry

Sections of formalin-fixed, paraffin-embedded tissue were processed as previously described 8 and stained with the PRA-specific antibody (C-19) or HDAC1 antibody using the avidin-biotin-peroxidase complex technique (Vectastain Elite ABC kit; Vector), as described previously 8. Staining intensity was quantified as described previously 11.

Statistical Analysis:

Data were analyzed using ANOVA and the Tukey multiple post t test (for multiple samples) or the Student's t test to compare the mean±SD using Graph Prism 4.0 software. Tumor growth curves were studied using regression analysis and slopes compared using analysis of variance followed by parallelism analysis.

Results:

The constitutive resistant tumor 59-HI showed a higher expression of HDAC 1 as compared to the antiprogestin sensitive tumor 59-2-HI ($p<0.001$). Immunohistochemical studies showed nuclear staining. In the case of the C4 tumors, both the sensitive tumors and the resistant tumors showed high levels of expression (FIG. 17). These data suggested that these tumors are candidates for treatment with HDAC inhibitors.

The co-treatment of 5azadC, TSA and MIF induced a significant inhibitory effect that was even greater than the one induced by 5azadC plus MIF in 59-HI tumors ($p<0.01$; FIG. 18). The right panels of FIG. 18 show representative images of the tumors at the end of the experiment. The inventors then decided to explore whether the co-treatment of the Dnmt inhibitor and the HDAC inhibitor increased the expression of PR-A as compared with the monotreatments. As shown in FIG. 19, a high expression of PR-A expression was observed in tumors treated with both agents. At the bottom of the Figure, PR-A staining in mammary glands are shown as positive nuclear PR-A staining. Tumors showed nuclear and cytosolic staining.

Similar experiments were performed using C4-2-HI tumors. As shown in FIG. 20, the co-treatment with the Dnmt inhibitor together with the HDAC inhibitor improved MIF responsiveness. Representative images showing the tumors at the end of the experiment are shown in the right panels of FIG. 20, and as shown in FIG. 21 an increase in PR-A was observed in tumors with the combined treatments. The top panel shows an immunofluorescence performed using isolated cells from the tumor and the lower panel shows a representative western blot.

Conclusion

The study found for the first time that (a) constitutive resistant mammary carcinomas showed high levels of HDAC1 which might be responsible for histone acetylation within the methylated PRA promoter (see FIG. 17); and (b) the combined treatment of a demethylating agent and a HDAC inhibitor (i) increased PR expression and (ii) increased the effectiveness of the demethylating agent in restoring sensitivity of the carcinoma to antiprogestins, better than the demethylating agent alone. These conclusions are supported by the data shown in FIGS. 16-21. The results support the hypothesis that tumors with high levels of PRA are those which respond to antiprogestin treatment.

REFERENCES FOR EXAMPLE 3

(1) Lapidus R G, Ferguson A T, Ottaviano Y L et al. Methylation of estrogen and progesterone receptor gene 5' CpG islands correlates with lack of estrogen and progesterone receptor gene expression in breast tumors. Clin Cancer Res. 1996; 2:805-810.

(2) Sharma D, Saxena N K, Davidson N E, Vertino P M. Restoration of tamoxifen sensitivity in estrogen receptor-negative breast cancer cells: tamoxifen-bound reactivated E R recruits distinctive co-repressor complexes. Cancer Res. 2006; 66:6370-6378.

(3) Momparler R L. Epigenetic therapy of cancer with 5-aza-2'-deoxycytidine (decitabine). Semin Oncol. 2005; 32:443-451.

(4) Yan L, Yang X, Davidson N E. Role of DNA methylation and histone acetylation in steroid receptor expression in breast cancer. J Mammary Gland Biol Neoplasia. 2001; 6:183-192.

(5) Fleury L, Gerus M, Lavigne A C, Richard-Foy H, Bystricky K. Eliminating epigenetic barriers induces transient hormone-regulated gene expression in estrogen receptor negative breast cancer cells. Oncogene. 2008; 27:4075-4085.
(6) Institute of Laboratory Animal Resources CoLSNRC. Guide for the Care and Use of Laboratory Animals. Washington, D.C.: National Academy Press; 1996.
(7) Wargon V, Helguero L A, Bolado J et al. Reversal of antiprogestin resistance and progesterone receptor isoform ratio in acquired resistant mammary carcinomas. Breast Cancer Res Treat. 2009; 116:449-460.
(8) Vanzulli S, Efeyan A, Benavides F et al. p21, p27 and p53 in estrogen and antiprogestin induced tumor regression of experimental mouse mammary ductal carcinomas. Carcinogenesis. 2002; 23:749-757.
(9) Helguero L A, Viegas M, Asaithamby A et al. Progesterone receptor expression in medroxyprogesterone acetate-induced murine mammary carcinomas and response to endocrine treatment. Breast Cancer Res Treat. 2003; 79:379-390.
(10) Lanari C, Lamb C A, Fabris V T et al. The MPA mouse breast cancer model: evidence for a role of progesterone receptors in breast cancer. Endocr Relat Cancer. 2009; 16:333-350.
(11) Soldati R, Wargon V, Cerliani J P et al. Inhibition of mammary tumor growth by estrogens: is there a specific role for estrogen receptors alpha and beta? Breast Cancer Res Treat. 2009.

Example 4

Animals.

Two-month-old virgin nude mice (nu/nu, University of La Plata Animal Facility) and NOD/LtSz-scid/IL-2Rgamma null mice (The Jackson Lab, Bar Harbor, Me. and bred in IBYME Animal Facility) were used.

Cell Lines.

BH-6 cell line was developed from an invasive ductal breast carcinoma (1). IBH-6 cells express basal levels of hormone receptors, they are tumorigenic and in vivo express higher levels of PRB than PRA (2). Cells were transfected with human PRB, PRA (pSG5-PRB, pSG5-PRA, kindly provided by K. Horwitz) or with the empty vector (pSG5), together with a plasmid encoding the neomycin resistance gene pIRES-N1(3), using Lipofectamine transfection reagent (Invitrogen) following the manufacturer's instructions. Transfected and selected cells were cultured in medium supplemented with 400 mg/ml G418 (neomycin analogue, GIBCO). The expression of PRB and PRA were analyzed by western blot and immunofluorescence (using Ab7 and Ab6 antibodies from Thermo Fisher). T47D-YA or YB were kindly provided by K. Horwitz and cultured as previously described (4).

Xenograft Studies.

Transfected and selected cells were grown up to confluence, washed with PBS, detached with 0.25% trypsin, centrifuged at 1000 rpm for 10 min and resuspended in a final concentration of $10^6$ (IBH-6) or $5 \times 10^6$ (T47D) cells per 100 µl of culture medium. The cells were sc inoculated into the right flank of nu/nu (IBH-6) or NOD/LtSz-scid/IL-2Rgamma null (T47D-YA or -YB cells) female mice. Only in experiments involving T47D cells E2 silastic pellets (0.5 mg) were implanted sc into the back of the animals one week prior tumor cell inoculation and 70 µl of Matrigel were mixed with the cell suspension at the moment of injection. MFP (6 mg) silastic pellets were sc implanted when tumors reached 20-40 $mm^2$. For T47D cells, experiments were repeated inoculating both cell types (T47D-YA or -YB) simultaneously in the left or right flank of the mouse, respectively.

Western Blots.

Cytosolic or nuclear extracts were processed for western blots as described previously (5). The cells were lysed using Mammalian Protein Extraction Reagent (Pierce, Rockford, Ill.) according to the manufacturer's instructions. The western blot membranes were incubated with antibodies against PR (C-19, Santa Cruz Biotech, CA, or Ab-7, Thermo Fisher), ERK (SC-94, Santa Cruz), Cyclin D1 (SC-753, Santa Cruz), MYC (SC-764, Santa Cruz) overnight at 4° C., at a concentration of 2 µg/ml in PBS-Tween 20. The band intensities from 3-4 different samples in different western blots were quantified using Image Quant software.

Immunohistochemistry.

Sections of formalin-fixed, paraffin-embedded tissue were stained with PR (C-19), or Ki67 (Dako, M7248) antibodies using the avidin-biotin-peroxidase complex technique (Vectastain Elite ABC kit; Vector), as described previously (6). Positive cells were counted in 10 high-power fields (HPFs) of each section, using 1000× magnification, and expressed as the mean±SEM of the ratio between the number of positive events and the total cell number.

Breast Cancer Samples.

Following the previous experiments shown in PART 1, breast cancer samples obtained after surgery from the Hospital General Pacheco (IRB approved by Hospital and IBYME) were used. Whenever possible, part of the sample is immediately frozen to be used in Western blot studies, other part is fixed to be used in IHC studies and a similar part is kept in medium culture. Slices obtained using a chopper were cultured for 48 hs with DMEM/F12 without phenol red and 10% fetal cal serum with or without MFP 10 nM. Tumor slices were then fixed, paraffin embedded and processed for immunohistochemistry. Cell proliferation was evaluated using Ki67 as described above. The number of slices depends on the sample size.

Statistical Analysis.

Data were analyzed using ANOVA and the Tukey multiple post t test (for multiple samples) or the Student's t test to compare the mean±SEM using Graph Prism 4.0 software. Mann Whitney and $X^2$ testes were used to evaluate Ki67+ cells in treated or untreated slices.

Results

Manipulation of PRA Levels in a Human Breast Cancer Cell Line Drives Antiprogestin Responsiveness To further corroborate the findings in the MPA-induced murine breast cancer model, a human xenograft model using IBH-6 cells was used. IBH-6 is a human breast cancer cell line which exhibits higher PRB than PRA levels[30]. These cells were stably transfected with PRB (IBH-6-PRB), PRA (IBH-6-PRA) or the empty vector (IBH-6-pSG5). The in vivo growth of IBH-6-PRA tumors was inhibited by treatment with MFP (p<0.05; FIG. 22B) while control IBH-6-pSG5 tumors was stimulated by MFP (p<0.001; FIG. 21A, left). FIG. 22 shows antiprogestins inhibit the growth of human IBH-6 tumors overexpressing PRA. A) Left. IBH-6 cells stably transfected with the empty vector (pSG5) were inoculated in nude mice (n=5/group). When tumors were palpable, animals were treated with vehicle, MPA (20 mg depot) or MFP (10 mg/kg/day). The mean±SEM of tumor sizes was plotted. *p<0.001 treated vs. untreated animals at the end of the experiment. B) Right: Tumors originated from cells transfected with PRA or empty vector were processed for Western blot to analyze the expression of PR.As expected a high ratio of PR-A/PR-B is only observed in PR-A transfected cells. B) Left. CLONE 27 of IHB-6 PRA cells was inoculated in nude mice. When tumors reached a size of 25 $mm^2$ (arrow) animals were treated with MFP (6 mg pellet, n=5). *p<0.001 treated vs. untreated animals.

The expression of CCND1 and MYC was evaluated in control or MFP-treated tumors. Total ERK was used as a loading control. Quantification of CCND1 and MYC relative to ERK shows a decrease in MYC and CCND1 expression in MFP-treated IBH-6_PRA tumors. *p<0.05, p<0.01, *p<0.001.

As shown in FIG. 22A right, IBH-6-PRA xenografts express higher levels of PRA than PRB while control or IBH-6-PRB xenografts show the opposite ratio (FIG. 22A, right). A down regulation of two PR regulated genes, cyclin D1(7) (CCND1, p<0.05) and MYC (8) (p<0.01) expression was only observed in MFP-treated IBH-6-PRA tumors (FIG. 1B bottom). MFP significantly inhibited the expression of CCND1 (p<0.05) and MYC (p<0.01). Together, these results confirm in a human breast cancer model, that the inhibitory effect of MFP on tumor growth requires high PRA/PRB profiles. Furthermore, only in these tumors MFP inhibited two PR regulated proteins involved in the tumor turnover such as CCND1 and MYC.

A Quimeric Xenograft Assay Confirms that PRA but not PRB Determines Responsiveness to Antiprogestins in T47D Cells.

FIG. 23 shows the effect of MFP on xenografts of T47D cells over expressing PRA or PRB. A Left: Western blots of T47D-YA and T47D-YB cell lysates showing PRA or PRB expression. Right: Scheme showing experimental protocol. B. Cells were inoculated in the right and left sc flanks of the same NOD/SCID/IL2R null female mice (n=3/group) which had been previously implanted with a 0.5 mg E2 pellet. When tumors reached a size of 30-60 $mm^2$ MFP or control pellets were implanted sc at the back. Tumor size was measured and plotted. Only PRA expressing tumors reduced their size after treatment. *p<0.05, treated vs. untreated animals. C. Cytokeratin staining in control or MFP-treated tumors (72 hs). Few neoplastic cells (brown) were observed in MFP treated tumors overexpressing PRA. (200×). D. Representative IHC studies showing CCDN1 and MYC expression. A decrease in nuclear CCDN1 staining was observed in T47D-YA tumors while the opposite pattern was observed in -YB tumors (400×). T47D-YA and -YB cells overexpress only PRA or PRB respectively (FIG. 23A, left) providing a different model as compared with IBH-6 cells which express basal levels of both PR isoforms. T47D-YA and -YB were injected into the right or left flank, respectively, of the same immunocompromised mice in which silastic E2 pellets have been implanted sc one week before (FIG. 23A, right). When tumors were around 20-40 $mm^2$, a MFP pellet or an empty pellet were implanted sc on the back of the animals. Interestingly, while T47D-YA tumors reduced their size after MFP treatment, T47D-YB tumors kept growing and no significant differences were observed between control and MFP-treated T47D-YB tumors (FIG. 23B). T47-YA tumors treated with MFP showed morphological signs of tumor regression, epithelial nests immersed in between dense fibrotic tissue were observed. Few mitotic figures and a high degree of apoptosis were registered in treated tumors. Conversely, a high number of mitotic figures were observed in T47D-YB treated or untreated tumors and no significant changes in tumor morphology were observed after treatment. The growth of PRA tumors was slower as compared with T47D-YB tumors as previously reported (9). MFP induced tissue remodeling as observed in FIG. 23C associated with decreased levels of nuclear MYC or CCND1 expression. (FIG. 23D, top). Interestingly, an intense nuclear staining of these proteins was observed in MFP-treated mice carrying T47-YB tumors.

Correlation of PR-A Expression and Antiprogestin Responsiveness in Breast Cancers The data has been extended regarding the study of PR isoform expression in human breast cancer samples and the evaluation of antiprogestin responsiveness in tissue culture. For this purpose a variation of our original technique was performed and cultured slices were obtained using a chopper that were immersed in filters containing the different solutions: control: medium plus 10% fetal calf serum and experimental, the same medium plus 10 nM RU486. Slices were cultures for 48 hs and processed for immunohistochemistry and Ki67 was used as a proliferative marker. FIG. 19 shows MFP induces an inhibition of cell proliferation (evaluated as Ki67 staining) in a breast cancer sample with a high PRA/PRB ratio. Top left: a decrease in Ki67 index was observed in slices of tumors incubated with 10 nM MFP as compared to control samples. Right: raw data of Ki67 quantification in different slices. Bottom: H&E and the PR IHC evaluation of the breast cancer sample and the Ki67 images observed in the chopper slices. FIG. 23 shows MFP stimulated cell proliferation (evaluated as Ki67 staining) in a breast cancer sample with a PRA/PRB ratio lower than 1. The graph design is similar to FIG. 25. Seven samples were evaluated using this technique:

3 cases in which PRA/PRB was high, a significant inhibition of Ki67 was observed in treated tumors, an example is shown in FIG. 24.

1 PR negative case, no inhibition was observed 2 cases PRA/PRB lower than 1, no inhibition was observed. Moreover a significant stimulation was observed in MFP-treated tumors (this example is shown in FIG. 25)

1 case with PRA/PRB lower than 1, a significant inhibition was observed.

In Table 3 we summarize the data obtained using both techniques:

These results clearly indicate that MFP responsiveness correlates with higher levels of PRA than PRB.

In 6 cases in which the PRA/PRB ratio predicted responsiveness, an inhibitory effect was obtained. From 7 cases that would have not predicted a response, one of them showed an inhibitory effect.

TABLE 3

| | Culture (previous exp) | | Chopper | | total | |
|---|---|---|---|---|---|---|
| | nhibitory effect | o inhibitory effect | nhibitory effect | o inhibitory effect | nhibitory effect | o inhibitory effect |
| RA/PRB >1 | # | | | | | |
| RA/PRB <1 | | | | * | | |
| R negative | | | | | | |

2 more cases gave the same trend although ns are not included
*In one case a stimulatory effect was observed.

These results clearly indicate that MFP responsiveness correlates with higher levels of PRA than PRB.

PR isoforms are easily determined by western blots. However this is not a friendly technique for a routine hospital practice. Thus, there is a need to search for markers that will help to select the patients with high PR-A levels, those susceptible to an antiprogestin treatment.

BCL-XL is one of the proteins selected considering the literature on available data arrays. IHC the expression of this protein was evaluated and the intensity and number of stained cells in each sample was scored. Samples of patients showing twice levels of PR A than PR-B or the opposite relation were selected. FIG. 26 shows correlation of BCL-XL expression and PR-A expression. Left top. Positive correlation between BCL-XL expression by IHC and the PRA/PRB ratio. Right top: Only tumors showing PRA/PRB levels higher that 2 or the opposite ratio were included in this analysis. A significant difference in BCL-XL expression was observed in both groups. Bottom: A score was obtained considering the intensity of expression and the number of stained cells. A representative image of a low (left) intermediate (middle) or high (right pattern of BCL-XL expression is shown.

As shown in FIG. 26, a significant difference was observed between both groups suggesting that BCL-XL is a candidate protein to be used to select PRA overexpressing tumors. A representative image of high, medium or low expression is shown in FIG. 25, bottom. At the top left, a correlation between the PRA/PRB data and the BCL-XL score of all samples evaluated is observed.

These studies as a whole indicate that patients with high PRA/PRB ratios may be susceptible to an antiprogestin therapy. BCL-XL is one of the candidate markers can be used together with others to be tested as predictors of high PR-A levels in PR positive breast cancer samples.

REFERENCES FOR EXAMPLE 4

(1) Vazquez, S. M., Mladovan, A., Garbovesky, C., Baldi, A., and Luthy, I. A. "Three novel hormone-responsive cell lines derived from primary human breast carcinomas: functional characterization." J. Cell Physiol, 199: 460-469, 2004.
(2) Bruzzone, A., Vanzulli, S. I., Soldati, R., Giulianelli, S., Lanari, C., and Luthy, I. A. "Novel human breast cancer cell lines IBH-4, IBH-6, and IBH-7 growing in nude mice." J Cell Physiol, 219: 477-484, 2009.
(3) Hobbs, S., Jitrapakdee, S., and Wallace, J. C. "Development of a bicistronic vector driven by the human polypeptide chain elongation factor 1 alpha promoter for creation of stable mammalian cell lines that express very high levels of recombinant proteins." Biochem. Biophys. Res Commun., 252: 368-372, 1998.
(4) Jacobsen, B. M., Richer, J. K., Schittone, S. A., and Horwitz, K. B. "New Human Breast Cancer Cells to Study Progesterone Receptor Isoform Ratio Effects and Ligand-independent Gene Regulation." J. Biol. Chem., 277: 27793-27800, 2002.
(5) Helguero, L. A., Viegas, M., Asaithamby, A., Shyamala, G., Lanari, C., and Molinolo, A. A. "Progesterone receptor expression in medroxyprogesterone acetate-induced murine mammary carcinomas and response to endocrine treatment." Breast Cancer Res. Treat., 79: 379-390, 2003.
(6) Vanzulli, S., Efeyan, A., Benavides, F., Helguero, L., Peters, G., Shen, J., Conti, C. J., Lanari, C., and Molinolo, A. "p21, p27 and p53 in estrogen and antiprogestin-induced tumor regression of experimental mouse mammary ductal carcinomas." Carcinogenesis, 23: 749-757, 2002.
(7) Musgrove, E. A. and Sutherland, R. L. "Effects of the progestin antagonist RU 486 on T-47D breast cancer cell cycle kinetics and cell cycle regulatory genes." Biochem. Biophys. Res Commun., 195: 1184-1190, 1993.
(8) Musgrove, E. A., Lee, C. S., and Sutherland, R. L. "Progestins both stimulate and inhibit breast cancer cell cycle progression while increasing expression of transforming growth factor alpha, epidermal growth factor receptor, c-fos, and c-myc genes." Mol. Cell Biol., 11: 5032-5043, 1991.
(9) Sartorius, C. A., Shen, T., and Horwitz, K. B. "Progesterone receptors A and B differentially affect the growth of estrogen-dependent human breast tumor xenografts." Breast Cancer Res Treat, 79: 287-299, 2003.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

ADDITIONAL REFERENCES INCORPORATED HEREIN BY REFERENCE IN THEIR ENTIRETIES

Actis A M, Caruso S P & Levin E 1995 Opposite effect of a cAMP analogue on tumoral growth related to hormone dependence of a murine mammary tumor. Cancer Lett. 96 81-85.
Afhuppe W, Beekman J M, Otto C, Korr D, Hoffmann J, Fuhrmann U & Moller C 2010 In vitro characterization of Z K 230211-A type III progesterone receptor antagonist with enhanced antiproliferative properties. J Steroid Biochem. Mol. Biol. 119 45-55.
Afhuppe W, Sommer A, Muller J, Schwede W, Fuhrmann U & Moller C 2009 Global gene expression profiling of progesterone receptor modulators in T47D cells provides a new classification system. J Steroid Biochem. Mol. Biol. 113 105-115.
Arruvito L, Giulianelli S, Flores A C, Paladino N, Barboza M, Lanari C & Fainboim L 2008 N K cells expressing a progesterone receptor are susceptible to progesterone-induced apoptosis. J. Immunol. 180 5746-5753.
Attardi B J, Burgenson J, Hild S A & Reel J R 2004 In vitro antiprogestational/antiglucocorticoid activity and progestin and glucocorticoid receptor binding of the putative metabolites and synthetic derivatives of CDB-2914, CDB-4124, and mifepristone. J Steroid Biochem. Mol. Biol. 88 277-288.
Attardi B J, Burgenson J, Hild S A, Reel J R & Blye R P 2002 CDB-4124 and its putative monodemethylated metabolite, CDB-4453, are potent antiprogestins with reduced antiglucocorticoid activity: in vitro comparison to mifepristone and CDB-2914. *Mol. Cell Endocrinol.* 188 111-123.

Aupperlee M, Kariagina A, Osuch J & Haslam S Z 2005 Progestins and breast cancer. *Breast Dis.* 24 37-57.

Bakker G H, Setyono-Han B, Henkelman M S, de Jong F H, Lamberts S W, van der Schoot P & Klijn J G 1987 Comparison of the actions of the antiprogestin mifepristone (RU486), the progestin megestrol acetate, the LHRH analog buserelin, and ovariectomy in treatment of rat mammary tumors. *Cancer Treatment Reports* 71 1021-1027.

Bakker G H, Setyono-Han B, Portengen H, de Jong F H, Foekens J A & Klijn J G 1989 Endocrine and antitumor effects of combined treatment with an antiprogestin and antiestrogen or luteinizing hormone-releasing hormone agonist in female rats bearing mammary tumors. *Endocrinology* 125 1593-1598.

Bakker G H, Setyono-Han B, Portengen H, de Jong F H, Foekens J A & Klijn J G 1990 Treatment of breast cancer with different antiprogestins: preclinical and clinical studies. *J Steroid Biochem. Mol. Biol.* 37 789-794.

Bardon S, Vignon F, Chalbos D & Rochefort H 1985 RU486, a progestin and glucocorticoid antagonist, inhibits the growth of breast cancer cells via the progesterone receptor. *The Journal of Clinical Endocrinology and Metabolism* 60 692-697.

Beck C A, Weigel N L, Moyer M L, Nordeen S K & Edwards D P 1993 The progesterone antagonist RU486 acquires agonist activity upon stimulation of cAMP signaling pathways. *Proc. Natl. Acad. Sci. U.S.A.* 90 4441-4445.

Benagiano G, Bastianelli C & Farris M 2008 Selective progesterone receptor modulators 3: use in oncology, endocrinology and psychiatry. *xpert. Opin. Pharmacother.* 9 2487-2496.

Beral V 2003 Breast cancer and hormone-replacement therapy in the Million Women Study. *Lancet* 362 419-427.

Boonyaratanakornkit V & Edwards D P 2007 Receptor mechanisms mediating nongenomic actions of sex steroids. *Semin. Reprod. Med.* 25 139-153.

Bottino M C, Cerliani J P, Rojas P, Giulianelli S, Soldati R, Mondillo C, Gorostiaga M A, Pignataro O P, Calvo J C, Gutkind J S, et al. 2011 Classical membrane progesterone receptors in murine mammary carcinomas: agonistic effects of progestins and RU-486 mediating rapid nongenomic effects. *Breast Cancer Res. Treat.* 126 621-636.

Bowden R T, Hissom J R & Moore M R 1989 Growth stimulation of T47D human breast cancer cells by the anti-progestin RU486. *Endocrinology* 124 2642-2644.

Brodie A M, Wing L Y, Goss P, Dowsett M & Coombes R C 1986 Aromatase inhibitors and the treatment of breast cancer. *Journal of steroid biochemistry* 24 91-97.

Busia L, Faus H, Hoffmann J & Haendler B 2011 The antiprogestin Lonaprisan inhibits breast cancer cell proliferation by inducing p21 expression. *Mol. Cell Endocrinol.* 333 37-46.

Calaf G M 2006 Susceptibility of human breast epithelial cells in vitro to hormones and drugs. *Int J Oncol* 28 285-295.

Cerliani J P, Giulianelli S, Sahores A, Wargon V, Gongora A, Baldi A, Molinolo A, Lamb C E & Lanari C 2010 Mifepristone inhibits MPA- and FGF2-induced mammary tumor growth but not FGF2-induced mammary hyperplasia. *Medicina (B Aires)* 70 529-532.

Check J H, Dix E, Cohen R, Check D & Wilson C 2010 Efficacy of the progesterone receptor antagonist mifepristone for palliative therapy of patients with a variety of advanced cancer types. *Anticancer Res.* 30 623-628.

Chlebowski R T, Anderson G L, Gass M, Lane D S, Aragaki A K, Kuller L H, Manson J E, Stefanick M L, Ockene J, Sarto G E, et al. 2010 Estrogen plus progestin and breast cancer incidence and mortality in postmenopausal women. *JAMA* 304 1684-1692.

Chlebowski R T, Hendrix S L, Langer R D, Stefanick M L, Gass M, Lane D, Rodabough R J, Gilligan M A, Cyr M G, Thomson C A, et al. 2003 Influence of estrogen plus progestin on breast cancer and mammography in healthy postmenopausal women: the Women's Health Initiative Randomized Trial. *JAMA* 289 3243-3253.

Chwalisz K, Brenner R M, Fuhrmann U U, Hess-Stumpp H & Elger W 2000 Antiproliferative effects of progesterone antagonists and progesterone receptor modulators on the endometrium. *Steroids* 65 741-751.

Chwalisz K, Perez M C, Demanno D, Winkel C, Schubert G & Elger W 2005 Selective progesterone receptor modulator development and use in the treatment of leiomyomata and endometriosis. *Endocr. Rev.* 26 423-438.

Clemm D L, Sherman L, Boonyaratanakornkit V, Schrader W T, Weigel N L & Edwards D P 2000 Differential hormone-dependent phosphorylation of progesterone receptor A and B forms revealed by a phosphoserine site-specific monoclonal antibody. *Mol. Endocrinol.* 14 52-65.

Conneely O M, Jericevic B M & Lydon J P 2003 Progesterone receptors in mammary gland development and tumorigenesis. *J. Mammary. Gland. Biol. Neoplasia.* 8 205-214.

Conneely O M & Lydon J P 2000 Progesterone receptors in reproduction: functional impact of the A and B isoforms. *Steroids* 65 571-577.

Dauvois S, White R & Parker M G 1993 The antiestrogen ICI 182780 disrupts estrogen receptor nucleocytoplasmic shuttling. *J Cell Sci.* 106 (Pt 4) 1377-1388. DeMarzo A M, Beck C A, Onate S A & Edwards D P 1991 Dimerization of mammalian progesterone receptors occurs in the absence of DNA and is related to the release of the 90-kDa heat shock protein. *Proceedings of the National Academy of Sciences of the United States of America* 88 72-76.

Dran G, Luthy I A, Molinolo A A, Montecchia F, Charreau E H, Pasqualini C D & Lanari C 1995 Effect of medroxyprogesterone acetate (MPA) and serum factors on cell proliferation in primary cultures of an MPA-induced mammary adenocarcinoma. *Breast Cancer Research and Treatment* 35 173-186.

Dressing G E & Lange C A 2009 Integrated actions of progesterone receptor and cell cycle machinery regulate breast cancer cell proliferation. *Steroids* 74 573-576.

Edwards D P, Altmann M, DeMarzo A, Zhang Y, Weigel N L & Beck C A 1995 Progesterone receptor and the mechanism of action of progesterone antagonists. *J Steroid Biochem. Mol. Biol.* 53 449-458.

El Etreby M F, Liang Y, Johnson M H & Lewis R W 2000 Antitumor activity of mifepristone in the human LNCaP, LNCaP-C4, and LNCaP-C4-2 prostate cancer models in nude mice. *Prostate* 42 99-106.

El Etreby M F, Liang Y, Wrenn R W & Schoenlein P V 1998 Additive effect of mifepristone and tamoxifen on apoptotic pathways in MCF-7 human breast cancer cells. *Breast Cancer Res. Treat.* 51 149-168.

Engman M, Skoog L, Soderqvist G & Gemzell-Danielsson K 2008 The effect of mifepristone on breast cell proliferation in premenopausal women evaluated through fine needle aspiration cytology. *Hum. Reprod.* 23 2072-2079.

Evans R M 1988 The steroid and thyroid hormone receptor superfamily. *Science* 240 889-895.

Fjelldal R, Moe B T, Orbo A & Sager G 2010 MCF-7 cell apoptosis and cell cycle arrest: non-genomic effects of progesterone and mifepristone (RU-486). *Anticancer Res.* 30 4835-4840.

Fuhrmann U, Hess-Stumpp H, Cleve A, Neef G, Schwede W, Hoffmann J, Fritzemeier K H & Chwalisz K 2000 Synthesis and biological activity of a novel, highly potent progesterone receptor antagonist. *J Med. Chem.* 43 5010-5016.

Gaddy V T, Barrett J T, Delk J N, Kallab A M, Porter A G & Schoenlein P V 2004 Mifepristone induces growth arrest, caspase activation, and apoptosis of estrogen receptor expressing, antiestrogen-resistant breast cancer cells. *Clinical Cancer Research: an official journal of the American Association for Cancer Research* 10 5215-5225.

Gaillard R C, Riondel A, Muller A F, Herrmann W & Baulieu E E 1984 RU 486: a steroid with antiglucocorticosteroid activity that only disinhibits the human pituitary-adrenal system at a specific time of day. *Proc. Natl. Acad. Sci. U.S.A* 81 3879-3882.

Galac S, Kooistra H S, Dieleman S J, Cestnik V & Okkens A C 2004 Effects of aglepristone, a progesterone receptor antagonist, administered during the early luteal phase in non-pregnant bitches. *Theriogenology* 62 494-500.

Giulianelli S, Cerliani J P, Lamb C A, Fabris V T, Bottino M C, Gorostiaga M A, Novaro V, Gongora A, Baldi A, Molinolo A, et al. 2008 Carcinoma-associated fibroblasts activate progesterone receptors and induce hormone independent mammary tumor growth: A role for the FGF-2/FGFR-2 axis. *Int J Cancer* 123 2518-2531.

Goyeneche A A, Caron R W & Telleria C M 2007 Mifepristone inhibits ovarian cancer cell growth in vitro and in vivo. *Clin. Cancer Res.* 13 3370-3379.

Graham J D, Yager M L, Hill H D, Byth K, O'Neill G M & Clarke C L 2005 Altered progesterone receptor isoform expression remodels progestin responsiveness of breast cancer cells. *Mol. Endocrinol.* 19 2713-2735.

Graham J D, Yeates C, Balleine R L, Harvey S S, Milliken J S, Bilous A M & Clarke C L 1995 Characterization of progesterone receptor A and B expression in human breast cancer. *Cancer Res.* 55 5063-5068.

Grunberg S M, Weiss M H, Russell C A, Spitz I M, Ahmadi J, Sadun A & Sitruk-Ware R 2006 Long-term administration of mifepristone (RU486): clinical tolerance during extended treatment of meningioma. *Cancer Invest* 24 727-733.

Grunberg S M, Weiss M H, Spitz I M, Ahmadi J, Sadun A, Russell C A, Lucci L & Stevenson L L 1991 Treatment of unresectable meningiomas with the antiprogesterone agent mifepristone. *Journal of neurosurgery* 74 861-866.

Gruol D J, Zee M C, Trotter J & Bourgeois S 1994 Reversal of multidrug resistance by RU 486. *Cancer research* 54 3088-3091.

Hagan C R, Faivre E J & Lange C A 2009 Scaffolding actions of membrane-associated progesterone receptors. *Steroids* 74 568-572.

Han S J, Tsai S Y, Tsai M J & O'Malley B W 2007 Distinct temporal and spatial activities of RU486 on progesterone receptor function in reproductive organs of ovariectomized mice. *Endocrinology* 148 2471-2486.

Helguero L A, Viegas M, Asaithamby A, Shyamala G, Lanari C & Molinolo A A 2003 Progesterone receptor expression in medroxyprogesterone acetate-induced murine mammary carcinomas and response to endocrine treatment. *Breast Cancer Res. Treat.* 79 379-390.

Herrman W, Wyss R, Riondel A, Philibert D, Teutsch G, Sakiz E & Baulieu E E 1982 [Effects of an anti-progestin steroid in women: interruption of the menstrual cycle or early pregnancy (author's transl)]. *Contraception, fertilite, sexualite* 10 389-393.

Hild S A, Reel J R, Hoffman L H & Blye R P 2000 CDB-2914: anti-progestational/antiglucocorticoid profile and post-coital anti-fertility activity in rats and rabbits. *Hum. Reprod.* 15 822-829.

Hissom J R & Moore M R 1987 Progestin effects on growth in the human breast cancer cell line T-47D-possible therapeutic implications. *Biochem. Biophys. Res. Commun.* 145 706-711.

Hopp T A, Weiss H L, Hilsenbeck S G, Cui Y, Allred D C, Horwitz K B & Fuqua S A 2004 Breast cancer patients with progesterone receptor P R-A-rich tumors have poorer disease-free survival rates. *Clin. Cancer Res.* 10 2751-2760.

Horwitz K B 1987 The structure and function of progesterone receptors in breast cancer. *J. Steroid Biochem.* 27 447-457.

Horwitz K B 2008 The Year in Basic Science: update of estrogen plus progestin therapy for menopausal hormone replacement implicating stem cells in the increased breast cancer risk. *Mol. Endocrinol.* 22 2743-2750.

Horwitz K B, Koseki Y & McGuire W L 1978 Estrogen control of progesterone receptor in human breast cancer: role of estradiol and antiestrogen. *Endocrinology* 103 1742-1751.

Horwitz K B & McGuire W L 1975 Predicting response to endocrine therapy in human breast cancer: a hypothesis. *Science* 189 726-727.

Horwitz K B, Mockus M B & Lessey B A 1982 Variant T47D human breast cancer cells with high progesterone-receptor levels despite estrogen and antiestrogen resistance. *Cell* 28 633-642.

Hyder S M, Liang Y, Wu J & Welbern V 2009 Regulation of thrombospondin-1 by natural and synthetic progestins in human breast cancer cells. *Endocr. Relat Cancer* 16 809-817.

Hyder S M, Murthy L & Stancel G M 1998 Progestin regulation of vascular endothelial growth factor in human breast cancer cells. *Cancer Res.* 58 392-395.

Jackson T A, Richer J K, Bain D L, Takimoto G S, Tung L & Horwitz K B 1997 The partial agonist activity of antagonist-occupied steroid receptors is controlled by a novel hinge domain-binding coactivator L7/SPA and the corepressors N-CoR or SMRT. *Molecular endocrinology* 11 693-705.

Jacobsen B M, Richer J K, Schittone S A & Horwitz K B 2002 New Human Breast Cancer Cells to Study Progesterone Receptor Isoform Ratio Effects and Ligand-independent Gene Regulation. *J. Biol. Chem.* 277 27793-27800.

Jemal A, Bray F, Center M M, Ferlay J, Ward E & Forman D 2011 Global cancer statistics. *CA Cancer J Clin.* 61 69-90.

Jeng M H, Langan-Fahey S M & Jordan V C 1993 Estrogenic actions of RU486 in hormone-responsive MCF-7 human breast cancer cells. *Endocrinology* 132 2622-2630.

Jordan V C 1990 Long-term adjuvant tamoxifen therapy for breast cancer. *Breast cancer research and treatment* 15 125-136.

Jordan V C 2008 The 38th David A. Karnofsky lecture: the paradoxical actions of estrogen in breast cancer—survival or death? *J Clin. Oncol* 26 3073-3082.

Kastner P, Krust A, Turcotte B, Stropp U, Tora L, Gronemeyer H & Chambon P 1990 Two distinct estrogen-regulated promoters generate transcripts encoding the two functionally different human progesterone receptor forms A and B. *EMBO J.* 9 1603-1614.

Keydar I, Chen L, Karby S, Weiss F R, Delarea J, Radu M, Chaitcik S & Brenner H J 1979 Establishment and characterization of a cell line of human breast carcinoma origin. *Eur. J. Cancer* 15 659-670.

Klijn J G, de Jong F H, Bakker G H, Lamberts S W, Rodenburg C J & Alexieva-Figusch J 1989 Antiprogestins, a new form of endocrine therapy for human breast cancer. *Cancer Res.* 49 2851-2856.

Klijn J G, Setyono-Han B & Foekens J A 2000 Progesterone antagonists and progesterone receptor modulators in the treatment of breast cancer. *Steroids* 65 825-830.

Klijn J G, Setyono-Han B, Sander H J, Lamberts S W, de Jong F H, Deckers G H & Foekens J A 1994 Pre-clinical and clinical treatment of breast cancer with antiprogestins. *Hum Reprod* 9 Suppl 1 181-189.

Kloosterboer H J, Deckers G H, Schoonen W G, Hanssen R G, Rose U M, Verbost P M, Hsiu J G, Williams R F & Hodgen G D 2000 Preclinical experience with two selective progesterone receptor modulators on breast and endometrium. *Steroids* 65 733-740.

Kordon E, Lanari C, Meiss R, Charreau E & Pasqualini C D 1990 Hormone dependence of a mouse mammary tumor line induced in vivo by medroxyprogesterone acetate. *Breast Cancer Res. Treat.* 17 33-43.

Lamb C, Simian M, Molinolo A, Pazos P & Lanari C 1999 Regulation of cell growth of a progestin-dependent murine mammary carcinoma in vitro: progesterone receptor involvement in serum or growth factor-induced cell proliferation. *J Steroid Biochem Mol Biol* 70 133-142.

Lamb C A, Helguero L A, Giulianelli S, Soldati R, Vanzulli S I, Molinolo A & Lanari C 2005 Antisense oligonucleotides targeting the progesterone receptor inhibit hormone independent breast cancer growth in mice. *Breast Cancer Res.* 7 R1111-R1121.

Lanari C, Kordon E, Molinolo A, Pasqualini C D & Charreau E H 1989 Mammary adencarcinomas induced by medroxyprogesterone acetate: hormone dependence and EGF receptors of BALB/c in vivo sublines. *Int. J. Cancer* 43 845-850.

Lanari C, Lamb C, Fabris V, Helguero L, Soldati R, Bottino M, Giulianelli S, Cerliani J, Wargon V & Molinolo A 2009 The MPA mouse breast cancer model: evidence for a role of progesterone receptors in breast cancer. *Endocr. Relat Cancer.*

Lanari C, Molinolo A A & Pasqualini C D 1986 Induction of mammary adenocarcinomas by medroxyprogesterone acetate in BALB/c female mice. *Cancer Lett.* 33 215-223.

Lange C A, Sartorius C A, Abdel-Hafiz H, Spillman M A, Horwitz K B & Jacobsen B M 2008 Progesterone receptor action: translating studies in breast cancer models to clinical insights. *Adv. Exp. Med. Biol.* 630 94-111.

Lecureur V, Fardel O & Guillouzo A 1994 The antiprogestatin drug RU 486 potentiates doxorubicin cytotoxicity in multidrug resistant cells through inhibition of P-glycoprotein function. *FEBS Lett.* 355 187-191.

Leonhardt S A, Boonyaratanakornkit V & Edwards D P 2003 Progesterone receptor transcription and non-transcription signaling mechanisms. *Steroids* 68 761-770.

Li M, Spitzer E, Zschiesche W, Binas B, Parczyk K & Grosse R 1995 Antiprogestins inhibit growth and stimulate differentiation in the normal mammary gland. *J Cell Physiol* 164 1-8.

Li X & O'Malley B W 2003 Unfolding the action of progesterone receptors. *J Biol. Chem.* 278 39261-39264.

Liang Y, Besch-Williford C, Brekken R A & Hyder S M 2007 Progestin-dependent progression of human breast tumor xenografts: a novel model for evaluating antitumor therapeutics. *Cancer Res.* 67 9929-9936.

Liang Y, Wu J, Stancel G M & Hyder S M 2005 p53-dependent inhibition of progestin induced VEGF expression in human breast cancer cells. *J Steroid Biochem. Mol. Biol.* 93 173-182.

Lydon J P, DeMayo F J, Funk C R, Mani S K, Hughes A R, Montgomery C A, Jr., Shyamala G, Conneely O M & O'Malley B W 1995 Mice lacking progesterone receptor exhibit pleiotropic reproductive abnormalities. *Genes Dev.* 9 2266-2278.

McGuire W L 1975 Endocrine therapy of breast cancer. *Annu. Rev. Med.* 26 353-363. Meyer M E, Pornon A, Ji J W, Bocquel M T, Chambon P & Gronemeyer H 1990 Agonistic and antagonistic activities of RU486 on the functions of the human progesterone receptor. *EMBO J.* 15 9 3923-3932.

Michna H, Schneider M, Nishino Y, el Etreby M F & McGuire W L 1990 Progesteroneantagonists block the growth of experimental mammary tumors in G0/G1. *Breast Cancer Res. Treat.* 17 155-156.

Michna H, Schneider M R, Nishino Y & el Etreby M F 1989 Antitumor activity of the antiprogestins Z K 98.299 and R U 38.486 in hormone dependent rat and mouse mammary tumors: mechanistic studies. *Breast Cancer Res. Treat.* 14 275-288.

Molinolo A A, Lanari C, Charreau E H, Sanjuan N & Pasqualini C D 1987 Mouse mammary tumors induced by medroxyprogesterone acetate: immunohistochemistry and hormonal receptors. *J. Natl. Cancer Inst.* 79 1341-1350.

Montecchia M F, Lamb C, Molinolo A A, Luthy I A, Pazos P, Charreau E, Vanzulli S Lanari C 1999 Progesterone receptor involvement in independent tumor growth in MPA-induced murine mammary adenocarcinomas. *J. Steroid Biochem. Mol. Biol.* 68 11-21.

Moore M R 2004 A rationale for inhibiting progesterone-related pathways to combat breast cancer. *Current cancer drug targets* 4 183-189.

Mulac-Jericevic B, Lydon J P, DeMayo F J & Conneely O M 2003 Defective mammary gland morphogenesis in mice lacking the progesterone receptor B isoform. *Proc. Natl. Acad. Sci. U.S.A* 100 9744-9749.

Muphung W, Rungsipipat A & Chatdarong K 2009 Effects of the anti-progestin 5 aglepristone on the uterine tissue of cats administered medroxyprogesterone acetate. *Reprod. Domest. Anim* 44 Suppl 2 204-207.

Murphy L C, Alkhalaf M, Dotzlaw H, Coutts A & Haddad-Alkhalaf B 1994 Regulation of gene expression in T-47D human breast cancer cells by progestins and antiprogestins. *Hum. Reprod.* 9 Suppl 1 174-180.

Murphy L C & Dotzlaw H 1989 Endogenous growth factor expression in T-47D, human breast cancer cells, associated with reduced sensitivity to antiproliferative effects of progestins and antiestrogens. *Cancer Res.* 49 599-604.

Nishino T, Ishibashi K, Hirtreiter C & Nishino Y 2009 Potentiation of the antitumor effect of tamoxifen by combination with the antiprogestin onapristone. *J Steroid Biochem. Mol. Biol.* 116 187-190.

Perrault D, Eisenhauer E A, Pritchard K I, Panasci L, Norris B, Vandenberg T & Fisher B 1996 Phase II study of the progesterone antagonist mifepristone in patients with untreated metastatic breast carcinoma: a National Cancer Institute of Canada Clinical Trials Group study. *J. Clin. Oncol.* 14 2709-2712.

Petz L N & Nardulli A M 2000 Sp1 binding sites and an estrogen response element halfsite are involved in regulation of the human progesterone receptor A promoter. *Mol. Endocrinol.* 14 972-985.

Petz L N, Ziegler Y S, Loven M A & Nardulli A M 2002 Estrogen receptor alpha and activating protein-1 mediate estrogen responsiveness of the progesterone receptor gene in MCF-25 7 breast cancer cells. *Endocrinology* 143 4583-4591.

Polisca A, Scotti L, Orlandi R, Brecchia G, Maranesi M, Zerani M & Boiti C 2010 Aglepristone (RU534) administration to non-pregnant bitches in the mid-luteal phase induces early luteal regression. *Theriogenology* 74 672-681.

Poole A J, Li Y, Kim Y, Lin S C, Lee W H & Lee E Y 2006 Prevention of Brca1-mediated mammary tumorigenesis in mice by a progesterone antagonist. *Science* 314 1467-1470.

Prat A, Parker J S, Karginova O, Fan C, Livasy C, Herschkowitz J I, He X & Perou C M 2010 Phenotypic and molecular characterization of the claudin-low intrinsic subtype of breast cancer. Breast cancer research: *BCR* 12 R68.

Richer J K, Jacobsen B M, Manning N G, Abel M G, Wolf D M & Horwitz K B 2002 5 Differential gene regulation by the two progesterone receptor isoforms in human breast cancer cells. *J. Biol. Chem.* 277 5209-5218.

Richert M M, Schwertfeger K L, Ryder J W & Anderson S M 2000 An atlas of mouse mammary gland development. *J Mammary Gland Biol Neoplasia* 5 227-241.

Rivas M A, Carnevale R P, Proietti C J, Rosemblit C, Beguelin W, Salatino M, Charreau E H, Frahm I, Sapia S, Brouckaert P, et al. 2008 TNF alpha acting on TNFR1 promotes breast cancer growth via p42/P44 MAPK, JNK, Akt and NF-kappa B-dependent pathways. *Exp. Cell Res.* 314 509-529.

Robertson J F, Willsher P C, Winterbottom L, Blamey R W & Thorpe S 1999 Onapristone, a progesterone receptor antagonist, as first-line therapy in primary breast cancer. *Eur. J. Cancer* 35 214-218.

Romieu G, Maudelonde T, Ulmann A, Pujol H, Grenier J, Cavalie G, Khalaf S & Rochefort H 1987 The antiprogestin RU486 in advanced breast cancer: preliminary clinical trial. *Bull. Cancer* 74 455-461.

Santen R, Cavalieri E, Rogan E, Russo J, Guttenplan J, Ingle J & Yue W 2009 Estrogen mediation of breast tumor formation involves estrogen receptor-dependent, as well as independent, genotoxic effects. *Annals of the New York Academy of Sciences* 1155 132-140.

Sartorius C A, Groshong S D, Miller L A, Powell R L, Tung L, Takimoto G S & Horwitz K B 1994 New T47D breast cancer cell lines for the independent study of progesterone B- and A receptors: only antiprogestin-occupied B-receptors are switched to transcriptional agonists by cAMP. *Cancer Res.* 54 3868-3877.

Sartorius C A, Tung L, Takimoto G S & Horwitz K B 1993 Antagonist-occupied human progesterone receptors bound to DNA are functionally switched to transcriptional agonists by cAMP. *J. Biol. Chem.* 268 9262-9266.

Schneider M R, Michna H, Nishino Y, Neef G & el Etreby M F 1990 Tumor-inhibiting potential of Z K 112.993, a new progesterone antagonist, in hormone-sensitive, experimental rodent and human mammary tumors. *Anticancer research* 10 683-687.

Schneider W, Ramachandran C, Satyaswaroop P G & Shyamala G 1991 Murine progesterone receptor exists predominantly as the 83-kilodalton 'A' form. *The Journal of steroid biochemistry and molecular biology* 38 285-291.

Schultz J R, Petz L N & Nardulli A M 2003 Estrogen receptor alpha and Sp1 regulate progesterone receptor gene expression. *Mol. Cell Endocrinol.* 201 165-175.

Sheridan P L, Krett N L, Gordon J A & Horwitz K B 1988 Human progesterone receptor transformation and nuclear down-regulation are independent of phosphorylation. *Mol. Endocrinol.* 2 1329-1342.

Shyamala G, Yang X, Silberstein G, Barcellos-Hoff M H & Dale E 1998 Transgenic mice carrying an imbalance in the native ratio of A to B forms of progesterone receptor exhibit developmental abnormalities in mammary glands. *Proc Natl Acad Sci USA* 95 696-701.

Simian M, Molinolo A & Lanari C 2006 Involvement of matrix metalloproteinase activity in hormone-induced mammary tumor regression. *Am J Pathol* 168 270-279.

Skafar D F 1991 Differences in the binding mechanism of RU486 and progesterone to the progesterone receptor. *Biochemistry* 30 10829-10832.

Skildum A, Faivre E & Lange C A 2005 Progesterone receptors induce cell cycle progression via activation of mitogen-activated protein kinases. *Mol. Endocrinol.* 19 327-339.

Spitz I M, Grunberg S M, Chabbert-Buffet N, Lindenberg T, Gelber H & Sitruk-Ware R 2005 Management of patients receiving long-term treatment with mifepristone. *Fertil. Steril.* 84 1719-1726.

Ulmann A & Dubois C 1988 Anti-progesterones in obstetrics, ectopic pregnancies and gynaecological malignancy. *Baillieres Clin. Obstet. Gynaecol.* 2 631-638.

Vanzulli S, Efeyan A, Benavides F, Helguero L, Peters G, Shen J, Conti C J, Lanari C & Molinolo A 2002 p21, p27 and p53 in estrogen and antiprogestin-induced tumor regression of experimental mouse mammary ductal carcinomas. *Carcinogenesis* 23 749-757.

Vanzulli S I, Soldati R, Meiss R, Colombo L, Molinolo A A & Lanari C 2005 Estrogen or antiprogestin treatment induces complete regression of pulmonary and axillary metastases in an experimental model of breast cancer progression. *Carcinogenesis* 26 1055-1063.

Vasilatos S N, Broadwater G, Barry W T, Baker J C, Jr., Lem S, Dietze E C, Bean G R, Bryson A D, Pilie P G, Goldenberg V, et al. 2009 CpG island tumor suppressor promoter methylation in non-BRCA-associated early mammary carcinogenesis. *Cancer Epidemiol. Biomarkers Prev.* 18 901-914.

Vignon F, Bardon S, Chalbos D & Rochefort H 1983 Antiestrogenic effect of R5020, a synthetic progestin in human breast cancer cells in culture. *J Clin. Endocrinol. Metab* 56 1124-1130.

Wargon V, Fernandez S V, Goin M, Giulianelli S, Russo J & Lanari C 2010 Hypermethylation of the progesterone receptor A in constitutive antiprogestin-resistant mouse mammary carcinomas. *Breast Cancer Res. Treat.*

Wargon V, Helguero L A, Bolado J, Rojas P, Novaro V, Molinolo A & Lanari C 2008 Reversal of antiprogestin resistance and progesterone receptor isoform ratio in acquired resistant mammary carcinomas. *Breast Cancer Res. Treat.*

Women's Health I 2002 Risks and benefits of estrogen plus progestin in healthy postmenopausal women: principal results From the Women's Health Initiative randomized controlled trial. *JAMA* 288 321-333.

Yoshida S, Ohara N, Xu Q, Chen W, Wang J, Nakabayashi K, Sasaki H, Morikawa A & Maruo T 2010 Cell-type specific actions of progesterone receptor modulators in the regulation of uterine leiomyoma growth. *Semin. Reprod. Med.* 28 260-273.

What is claimed is:

1. A method of treating a human subject having luminal breast cancer that is constitutively resistant to an antiprogestin, comprising adjusting said luminal breast cancer to possess a molar amount of progesterone receptor isoform A (PR-A) that it is greater than that of isoform B (PR-B) by administering an effective amount of a demethylating agent and an HDAC inhibitor, and administering a therapeutically effective amount of the antiprogestin, thereby treating the breast cancer.

2. The method of claim 1, wherein, the antiprogestin is a Type I, Type II, or Type III antiprogestin.

3. The method of claim 1, wherein the antiprogestin is onapristone, mifepristone (RU-486), lonaprisan, aglepristone (Ru-534), Org31710, Org31806, CDB-2914, or telapristone (CDB-4124).

4. The method of claim 1, further comprising co-administering an additional anticancer agent.

5. The method of claim 1, wherein the molar amounts of PR-A and PR-B are adjusted prior to the step of administering the antiprogestin.

6. The method of claim 1, wherein the step of increasing the molar amount of PR-A so that it is greater than that of PR-B further comprises administering a therapeutically effective amount of a nucleic acid molecule of SEQ ID NO: 3 or a nucleic acid having at least 85% sequence identify therewith and encoding a protein having the activity of PR-A.

7. The method of claim 1, wherein the step of increasing the molar ratio of PR-A so that it is greater than that of PR-B further comprises administering a therapeutically effective amount of an inhibitory nucleic acid of PR-B expression, wherein the inhibitory nucleic acid hybridizes to SEQ ID NO: 2 or a nucleic acid having at least 85% sequence identity to SEQ ID NO: 2.

8. The method of claim 1, wherein the demethylating agent is 5azadC, azacytidine (aza) or zebularine.

9. The method of claim 1, wherein the HDAC inhibitor is selected from the group consisting of TSA (trichostatin A), Vorinostat, Romidespin, Panobiostat (LBH589), Valproic acid, Belinostat (PXD101), Mocetinostat (MGCD0103), PCI-24781, Entinostat (MS-275), SB939, 5 Resminostat (4SC-201), CUDC-101, AR-42, CHR-2845, CHR-3996, 4SC-202, sulforaphane, and Givinostat (ITF2357), or any combination thereof.

10. A method of restoring the sensitivity of luminal breast cancer in a human that is constitutively resistant to an antiprogestin comprising increasing the molar amount of PR-A to PR-B in the luminal carcinoma by administering an effective amount of a demethylating agent and an effective amount of an HDAC inhibitor.

11. The method of claim 10, wherein the demethylating agent is 5azadC, azacytidine (aza) or zebularine.

12. The method of claim 10, wherein the HDAC inhibitor is selected from the group consisting of TSA (trichostatin A), Vorinostat, Romidespin, Panobiostat (LBH589), Valproic acid, Belinostat (PXD101), Mocetinostat (MGCD0103), PCI-24781, Entinostat (MS-275), SB939, 5 Resminostat (4SC-201), CUDC-101, AR-42, CHR-2845, CHR-3996, 4SC-202, sulforaphane, and Givinostat (ITF2357), or any combination thereof.

13. A method of treating a constitutive antiprogestin-resistant luminal breast cancer in a human comprising increasing the molar amount of PR-A to PR-B ratio in the luminal breast cancer and administering a therapeutically effective amount of an antiprogestin, thereby treating the luminal cancer, wherein increasing the molar amount of PR-A to PR-B is carried out by administering an effective amount of a demethylating agent and an effective amount of an HDAC inhibitor.

14. The method of claim 13, wherein said administered antiprogestin is onapristone, Mifepristone (RU-486), lonaprisan, aglepristone (Ru-534), Org31710, Org31806, CDB-2914, or telapristone (CDB-4124).

15. The method of claim 13, wherein the demethylating agent is 5azadC, azacytidine (aza) or zebularine.

16. The method of claim 13, wherein the HDAC inhibitor is selected from the group consisting of TSA (trichostatin A), Vorinostat, Romidespin, Panobiostat (LBH589), Valproic acid, Belinostat (PXD101), Mocetinostat (MGCD0103), PCI-24781, Entinostat (MS-275), SB939, 5 Resminostat (4SC-201), CUDC-101, AR-42, CHR-2845, CHR-3996, 4SC-202, sulforaphane, and Givinostat (ITF2357), or any combination thereof.

* * * * *

SEQUENCE LISTING

<160> NUMBER OF SEQ ID NOS: 19

<210> SEQ ID NO 1
<211> LENGTH: 3014
<212> TYPE: DNA
<213> ORGANISM: Homo sapiens
<220> FEATURE:
<221> NAME/KEY: misc_feature
<222> LOCATION: (1)..(3014)
<223> OTHER INFORMATION: Full-Length hPR cDNA, ACCESSION   M15716

<400> SEQUENCE: 1

```
ctgaccagcg ccgccctccc ccgccccga cccaggaggt ggagatccct ccggtccagc      60
cacattcaac acccactttc tcctccctct gcccctatat tcccgaaacc ccctcctcct     120
tcccttttcc ctcctccctg gagacggggg aggagaaaag gggagtccag tcgtcatgac     180
tgagctgaag gcaaagggtc cccgggctcc ccacgtggcg ggcggcccgc cctcccccga     240
ggtcggatcc ccactgctgt gtcgcccagc cgcaggtccg ttccggggga gccagacctc     300
ggacaccttg cctgaagttt cggccatacc tatctccctg gacgggctac tcttccctcg     360
gccctgccag ggacaggacc cctccgacga aaagacgcag gaccagcagt cgctgtcgga     420
cgtggagggc gcatattcca gagctgaagc tacaaggggt gctggaggca gcagttctag     480 tccccccagaa aaggacagcg gactgctgga cagtgtcttg gacactctgt tggcgccctc     540
aggtcccggg cagagccaac ccagccctcc cgcctgcgag gtcaccagct cttggtgcct     600
gtttggcccc gaacttcccg aagatccacc ggctgccccc gccacccagc gggtgttgtc     660
cccgctcatg agccggtccg ggtgcaaggt tggagacagc tccgggacgg cagctgccca     720
taaagtgctg ccccggggcc tgtcaccagc ccggcagctg ctgctcccgg cctctgagag     780
ccctcactgg tccggggccc cagtgaagcc gtctccgcag gccgctgcgg tggaggttga     840
ggaggaggat ggctctgagt ccgaggagtc tgcgggtccg cttctgaagg gcaaacctcg     900
ggctctgggt ggcgcggcgg ctggaggagg agccgcggct gtcccgccgg gggcggcagc     960
aggaggcgtc gccctggtcc ccaaggaaga ttcccgcttc tcagcgccca gggtcgccct    1020
ggtggagcag gacgcgccga tggcgcccgg gcgctccccg ctgccacca cggtgatgga    1080 tttcatccac gtgcctatcc tgcctctcaa tcacgcctta ttggcagccc gcactcggca    1140
gctgctggaa gacgaaagtt acgacggcgg ggccggggct gccagcgcct ttgccccgcc    1200
gcggagttca ccctgtgcct cgtccacccc ggtgctgtca ggcgacttcc ccgactgcgc    1260
gtacccgccc gacgccgagc ccaaggacga cgcgtaccct ctctatagcg acttccagcc    1320
gcccgctcta aagataaagg aggaggagga aggcgcggag gcctccgcgc gctcccgcg    1380 ttcctaccct gtggccggtg ccaacccgc agccttccg gatttcccgt tggggccacc    1440 gccccgctg ccgccgcgag cgaccccatc cagacccggg gaagcggcgg tgacggccgc    1500
acccgccagt gcctcagtct cgtctgcgtc ctcctcgggg tcgaccctgg agtgcatcct    1560
gtacaaagcg gagggcgcgc cgcccagca gggcccgttc gcgccgccgc cctgcaaggc    1620
gccgggcgcg agcggctgcc tgctccccgcg ggacggcctg ccctccacct ccgcctctgc    1680
```

```
cgccgccgcc ggggcggccc ccgcgctcta ccctgcactc ggcctcaacg ggctcccgca    1740
gctcggctac caggccgccg tgctcaagga gggcctgccg caggtctacc cgccctatct    1800
caactacctg aggccggatt cagaagccag ccagagccca caatacagct tcgagtcatt    1860
acctcagaag atttgtttaa tctgtgggga tgaagcatca ggctgtcatt atggtgtcct    1920
tacctgtggg agctgtaagg tcttctttaa gagggcaatg gaagggcagc acaactactt    1980
atgtgctgga gaaatgact gcatcgttga taaaatccgc agaaaaaact gcccagcatg    2040
tcgccttaga aagtgctgtc aggctggcat ggtccttgga ggtcgaaaat ttaaaaagtt    2100
caataaagtc agagttgtga gagcactgga tgctgttgct ctcccacagc cagtgggcgt    2160
tccaaatgaa agccaagccc taagccagag attcactttt tcaccaggtc aagacataca    2220
gttgattcca ccactgatca acctgttaat gagcattgaa ccagatgtga tctatgcagg    2280
acatgacaac acaaaacctg acacctccag ttctttgctg acaagtctta atcaactagg    2340
cgagaggcaa cttctttcag tagtcaagtg gtctaaatca ttgccaggtt ttcgaaactt    2400
acatattgat gaccagataa ctctcattca gtattcttgg atgagcttaa tggtgtttgg    2460
tctaggatgg agatcctaca aacacgtcag tgggcagatg ctgtattttg cacctgatct    2520
aatactaaat gaacagcgga tgaaagaatc atcattctat tcattatgcc ttaccatgtg    2580
gcagatccca caggagtttg tcaagcttca agttagccaa gaagagttcc tctgtatgaa    2640
agtattgtta cttcttaata caattccttt ggaagggcta cgaagtcaaa cccagtttga    2700
ggagatgagg tcaagctaca ttagagagct catcaaggca attggtttga ggcaaaaagg    2760
agttgtgtcg agctcacagc gtttctatca acttacaaaa cttcttgata acttgcatga    2820
tcttgtcaaa caacttcatc tgtactgctt gaatacattt atccagtccc gggcactgag    2880
tgttgaattt ccagaaatga tgtctgaagt tattgctgca caattaccca agatattggc    2940
agggatggtg aaaccccttc tctttcataa aaagtgaatg tcatcttttt cttttaaaga    3000
attaaatttt gtgg                                                      3014
```

<210> SEQ ID NO 2  
<211> LENGTH: 2802  
<212> TYPE: DNA  
<213> ORGANISM: Homo sapiens  
<220> FEATURE:  
<221> NAME/KEY: misc_feature  
<222> LOCATION: (1)..(2802)  
<223> OTHER INFORMATION: hPR cDNA Isoform B

<400> SEQUENCE: 2

```
atgactgagc tgaaggcaaa gggtccccgg gctccccacg tggcgggcgg cccgcccctcc     60 cccgaggtcg gatccccact gctgtgtcgc ccagccgcag gtccgttccc ggggagccag    120
acctcggaca ccttgcctga gtttcggcc ataccctatct ccctggacgg gctactcttc    180
cctcggccct gccagggaca ggaccccctcc gacgaaagga cgcaggacca gcagtcgctg    240
tcggacgtgg agggcgcata ttccagagct gaagctacaa ggggtgctgg aggcagcagt    300
tctagtcccc cagaaaagga cagcggactg ctggacagtg tcttggacac tctgttggcg    360
ccctcaggtc ccgggcagag ccaacccagc cctcccgcct gcaggtcac cagctcttgg    420 tgcctgtttg gccccgaact tcccgaagat ccaccggctg ccccgccac ccagcgggtg    480 ttgtcccgc tcatgagccg gtccgggtgc aaggttggag acagtccgg acgcagct      540 gcccataaag tgctgccccg gggcctgtca ccagcccggc agctgctgct cccggcctct    600
```

```
gagagccctc actggtccgg ggccccagtg aagccgtctc cgcaggccgc tgcggtggag    660
gttgaggagg aggatggctc tgagtccgag gagtctgcgg gtccgcttct gaagggcaaa    720
cctcgggctc tgggtggcgc ggcggctgga ggaggagccg cggctgtccc gccggggggcg    780 gcagcaggag gcgtcgccct ggtcgccccaag gaagattccc gcttctcagc gcccagggtc    840
gccctggtgg agcaggacgc gccgatggcg cccgggcgct cccgctggc caccacggtg      900 atggatttca tccacgtgcc tatcctgcct ctcaatcacg ccttattggc agcccgcact      960
cggcagctgc tggaagacga aagttacgac ggcgggggccg gggctgccag cgcctttgcc    1020
ccgccgcgga gttcaccctg tgcctcgtcc accccggtcg ctgtaggcga cttccccgac    1080
tgcgcgtacc cgcccgacgc cgagcccaag gacgacgcgt accctctcta tagcgacttc    1140
cagccgcccg ctctaaagat aaaggaggag gaggaaggcg cggaggcctc cgcgcgctcc    1200
ccgcgttcct accttgtggc cggtgccaac cccgcagcct tcccggattt cccgttgggg    1260
ccaccgcccc cgctgccgcc gcgagcgacc ccatccagac ccggggaagc ggcggtgacg    1320
gccgcacccg ccagtgcctc agtctcgtct gcgtcctcct cggggtcgac cctggagtgc    1380
atcctgtaca aagcggaggg cgcgccgccc cagcagggcc cgttcgcgcc gccgccctgc    1440
aaggcgccgg gcgcgagcgg ctgcctgctc cgcgggacg gcctgccctc cacctccgcc    1500
tctgccgccg ccgccggggc ggccccgcg ctctaccctg cactcggcct caacgggctc    1560
ccgcagctcg gctaccaggc cgccgtgctc aaggagggcc tgccgcaggt ctacccgccc    1620
tatctcaact acctgaggcc ggattcagaa gccagccaga gcccacaata cagcttcgag    1680
tcattacctc agaagatttg tttaatctgt ggggatgaag catcaggctg tcattatggt    1740
gtccttacct gtgggagctg taaggtcttc tttaagaggg caatggaagg gcagcacaac    1800
tacttatgtg ctggaagaaa tgactgcatc gttgataaaa tccgcagaaa aaactgccca    1860
gcatgtcgcc ttagaaagtg ctgtcaggct ggcatggtcc ttggaggtcg aaaatttaaa    1920
aagttcaata aagtcagagt tgtgagagca ctggatgctg ttgctctccc acagccagtg    1980
ggcgttccaa atgaaagcca agccctaagc cagagattca cttttttcacc aggtcaagac    2040 atacagttga ttccaccact gatcaacctg ttaatgagca ttgaaccaga tgtgatctat    2100
gcaggacatg acaacacaaa acctgacacc tccagttctt tgctgacaag tcttaatcaa    2160
ctaggcgaga ggcaacttct ttcagtagtc aagtggtcta aatcattgcc aggttttcga    2220
aacttacata ttgatgacca gataactctc attcagtatt cttggatgag cttaatggtg    2280
tttggtctag gatggagatc ctacaaacac gtcagtgggc agatgctgta ttttgcacct    2340
gatctaatac taaatgaaca gcggatgaaa gaatcatcat tctattcatt atgccttacc    2400
atgtggcaga tcccacagga gtttgtcaag cttcaagtta gccaagaaga gttcctctgt    2460
atgaaagtat tgttacttct taatacaatt cctttggaag ggctacgaag tcaaacccag    2520
tttgaggaga tgaggtcaag ctacattaga gagctcatca aggcaattgg tttgaggcaa    2580
aaaggagttg tgtcgagctc acagcgtttc tatcaactta caaaacttct tgataacttg    2640
catgatcttg tcaaacaact tcatctgtac tgcttgaata catttatcca gtcccgggca    2700
ctgagtgttg aatttccaga aatgatgtct gaagttattg ctgcacaatt acccaagata    2760
ttggcaggga tggtgaaacc ccttctcttt cataaaaagt ga                       2802
```

<210> SEQ ID NO 3
<211> LENGTH: 2310
<212> TYPE: DNA
<213> ORGANISM: Homo sapiens
<220> FEATURE:
<221> NAME/KEY: misc_feature
<222> LOCATION: (1)..(2310)
<223> OTHER INFORMATION: hPR Isoform A cDNA

<400> SEQUENCE: 3

| | | | | | |
|---|---|---|---|---|---|
| atgagccggt | ccgggtgcaa | ggttggagac | agctccggga | cggcagctgc | ccataaagtg | 60 |
| ctgccccggg | gcctgtcacc | agcccggcag | ctgctgctcc | cggcctctga | gagccctcac | 120 |
| tggtccgggg | ccccagtgaa | gccgtctccg | caggccgctg | cggtggaggt | tgaggaggag | 180 |
| gatggctctg | agtccgagga | gtctgcgggt | ccgcttctga | agggcaaacc | tcgggctctg | 240 |
| ggtgcgcgcg | cggctggagg | aggagccgcg | gctgtcccgc | cggggcggc | agcaggaggc | 300 |
| gtcgccctgg | tccccaagga | agattcccgc | ttctcagcgc | ccagggtcgc | cctggtggag | 360 |
| caggacgcgc | cgatgcgcc | cgggcgctcc | ccgctggcca | ccacggtgat | ggatttcatc | 420 |
| cacgtgccta | tcctgcctct | caatcacgcc | ttattggcag | cccgcactcg | gcagctgctg | 480 |
| gaagacgaaa | gttacgacgg | cggggccggg | gctgccagcg | cctttgcccc | gccgcggagt | 540 |
| tcaccctgtg | cctcgtccac | cccggtcgct | gtaggcgact | tccccgactg | cgcgtacccg | 600 |
| cccgacgccg | agcccaagga | cgacgcgtac | cctctctata | gcgacttcca | gccgcccgct | 660 |
| ctaaagataa | aggaggagga | ggaaggcgcg | gaggcctccg | cgcgctcccc | gcgttcctac | 720 |
| cttgtggccg | gtgccaaccc | cgcagccttc | ccggatttcc | cgttggggcc | accgccccg | 780 |
| ctgccgccgc | gagcgacccc | atccagaccc | ggggaagcgg | cggtgacggc | cgcacccgcc | 840 |
| agtgcctcag | tctcgtctgc | gtcctcctcg | gggtcgaccc | tggagtgcat | cctgtacaaa | 900 |
| gcggagggcg | cgccgcccca | gcagggcccg | ttcgcgccgc | cgcccgcaa | ggcgccgggc | 960 |
| gcgagcggct | gcctgctccc | gcgggacggc | ctgccctcca | cctccgcctc | tgccgccgcc | 1020 |
| gccggggcgg | ccccgcgct | ctaccctgca | ctcggcctca | cgggctccc | gcagctcggc | 1080 |
| taccaggccg | ccgtgctcaa | ggagggcctg | ccgcaggtct | acccgcccta | tctcaactac | 1140 |
| ctgaggccgg | attcagaagc | cagccagagc | ccacaataca | gcttcgagtc | attacctcag | 1200 |
| aagatttgtt | taatctgtgg | ggatgaagca | tcaggctgtc | attatggtgt | ccttacctgt | 1260 |
| gggagctgta | aggtcttctt | taagagggca | atggaagggc | agcacaacta | cttatgtgct | 1320 |
| ggaagaaatg | actgcatcgt | tgataaaatc | cgcagaaaaa | actgcccagc | atgtcgcctt | 1380 |
| agaaagtgct | gtcaggctgg | catggtcctt | ggaggtcgaa | aatttaaaaa | gttcaataaa | 1440 |
| gtcagagttg | tgagagcact | ggatgctgtt | gctctcccac | agccagtggg | cgttccaaat | 1500 |
| gaaagccaag | ccctaagcca | gagattcact | ttttcaccag | gtcaagacat | acagttgatt | 1560 |
| ccaccactga | tcaacctgtt | aatgagcatt | gaaccagatg | tgatctatgc | aggacatgac | 1620 |
| aacacaaaac | ctgacacctc | cagttctttg | ctgacaagtc | ttaatcaact | aggcgagagg | 1680 |
| caacttcttt | cagtagtcaa | gtggtctaaa | tcattgccag | gttttcgaaa | cttacatatt | 1740 |
| gatgaccaga | taactctcat | tcagtattct | tggatgagct | aatggtgtt | tggtctagga | 1800 |
| tggagatcct | acaaacacgt | cagtgggcag | atgctgtatt | ttgcacctga | tctaatacta | 1860 |
| aatgaacagc | ggatgaaaga | atcatcattc | tattcattat | gccttaccat | gtggcagatc | 1920 |
| ccacaggagt | ttgtcaagct | tcaagttagc | caagaagagt | tcctctgtat | gaaagtattg | 1980 |
| ttacttctta | atacaattcc | tttggaaggg | ctacgaagtc | aaacccagtt | tgaggagatg | 2040 |
| aggtcaagct | acattagaga | gctcatcaag | gcaattggtt | tgaggcaaaa | aggagttgtg | 2100 |
| tcgagctcac | agcgtttcta | tcaacttaca | aaacttcttg | ataacttgca | tgatcttgtc | 2160 |

```
aaacaacttc atctgtactg cttgaataca tttatccagt cccgggcact gagtgttgaa    2220
tttccagaaa tgatgtctga agttattgct gcacaattac ccaagatatt ggcagggatg    2280
gtgaaacccc ttctctttca taaaaagtga                                     2310
```

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gggcgggttt ttttagagc                                                   19
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
ctcgttctcc tacaacgaca                                                  20
```

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ttttgggtgg gttttttag agt                                               23
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tactcattct cctacaacaa caa                                              23
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
attttatcgt tatcgggata gcgc                                             24
```

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
ataaatataa aatcgcaaaa cccg                                          24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tattttattg ttattgggat agtgt                                         25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aataaatata aaatcacaaa accca                                         25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaagaaatac gaaaaaaagt ttttc                                         25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ataaatataa aatcgcaaaa cccg                                          24

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agaagaaata tgaaaaaaag tttttt                                        26

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 15
aataaatata aaatcacaaa accca                                          25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16 gtttttata cgtttggcgt ttc                                             23

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cacgtcgaac aacgactact                                                20

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18 aggttttta tatgtttggt gtttt                                           25

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctccacatca aacaacaact act                                            23
```